(12) United States Patent
Keay et al.

(10) Patent No.: US 8,404,655 B2
(45) Date of Patent: Mar. 26, 2013

(54) INHIBITION OF PALMITOYL ACYL TRANSFERASE EXPRESSION AND/OR ACTIVITY FOR THE REGULATION OF ANTIPROLIFERATIVE FACTOR ACTIVITY

(75) Inventors: Susan K. Keay, Ellicott City, MD (US); David Zacharias, Palm Coast, FL (US); Sonia L. Planey, St. Augustine, FL (US)

(73) Assignees: University of Florida Research Foundation, Inc., Gainesville, FL (US); University of Maryland, Baltimore, MD (US); The United States of America as represented by the Department of Veterans Affairs, Washington, DC (US)

( * ) Notice: Subject to any disclaimer, the term of this patent is extended or adjusted under 35 U.S.C. 154(b) by 393 days.

(21) Appl. No.: 12/600,571

(22) PCT Filed: May 16, 2008

(86) PCT No.: PCT/US2008/063860
§ 371 (c)(1),
(2), (4) Date: Apr. 14, 2010

(87) PCT Pub. No.: WO2008/144485
PCT Pub. Date: Nov. 27, 2008

(65) Prior Publication Data
US 2010/0190684 A1 Jul. 29, 2010

Related U.S. Application Data

(60) Provisional application No. 61/012,676, filed on Dec. 10, 2007, provisional application No. 60/938,874, filed on May 18, 2007.

(51) Int. Cl.
*A61K 31/70* (2006.01)
*C07H 21/04* (2006.01)
(52) U.S. Cl. .......................................... 514/44; 536/24.5
(58) Field of Classification Search ........................ None
See application file for complete search history.

(56) References Cited

U.S. PATENT DOCUMENTS

| | | |
|---|---|---|
| 2002/0016443 A1 | 2/2002 | Keay et al. |
| 2004/0161476 A1* | 8/2004 | Hahn et al. .................... 424/679 |
| 2005/0096263 A1 | 5/2005 | Keay et al. |

FOREIGN PATENT DOCUMENTS

WO    WO-2008/014484 A1    1/2008

OTHER PUBLICATIONS

Ducker et al. Oncogene 2004, vol. 23, pp. 9230-9237.*
Ducker et al. Molecular Cancer Therapeutics 2006, vol. 5, pp. 1647-1659.*
International Search Report issued Nov. 24, 2009 during the prosecution of International Application No. PCT/US2008/063860.
Conrads et al., "CKAP4/p63 Is a Receptor for the Frizzled-8 Protein-related Antiproliferative Factor from Interstitial Cystitis Patients"; Dec. 8, 2006 The Journal of Biological Chemistry, 281, 37836-37843.
Keay et al., "An antiproliferative factor from interstitial cystitis patients is a frizzled 8 protein-related sialoglycopeptide", Proc Natl Acad Sci U S A. Aug. 10, 2004; 101(32): 11803-11808.
International Search Report issued Dec. 9, 2008 during prosecution of International Application No. PCT/US2008/063860.

* cited by examiner

*Primary Examiner* — Tracy Vivlemore
(74) *Attorney, Agent, or Firm* — Fulbright & Jaworski, LLP

(57) ABSTRACT

The invention generally concerns inhibition of a molecule that has a role in post-translational modification of a receptor for antiproliferative factor (APF) of bladder epithelial cells, thereby modulating the APF. In particular, inhibition of DHHC2 activity and/or ZDHHC2 expression results in modulation of APF receptor activity, and in specific aspects such modulation is therapeutic and/or preventative for a bladder condition, such as interstitial cystitis. In addition, inhibition of CKAP4 palmitoylation in certain cases also decreases its activity as a tPA receptor on smooth muscle cells or surfactant A on type II pneumocytes, and/or generally inhibits its function as a cell membrane receptor, cell chaperone molecule, and/or membrane trafficking agent.

6 Claims, 12 Drawing Sheets

FIG. 1

A  HeLa

B  NB

A

B

INHIBITION OF PALMITOYL ACYL TRANSFERASE EXPRESSION AND/OR ACTIVITY FOR THE REGULATION OF ANTIPROLIFERATIVE FACTOR ACTIVITY

This application claims priority to U.S. Provisional Patent Application Ser. No. 60/938,874, filed May 18, 2007, and U.S. Provisional Patent Application Ser. No. 61/012,676, filed Dec. 10, 2007, both of which applications are incorporated by reference herein in their entirety.

STATEMENT REGARDING FEDERALLY SPONSORED RESEARCH OR DEVELOPMENT

This invention was made with government support under Grant No. DK-52596 awarded by the National Institutes of Health. The government has certain rights in the invention.

FIELD OF THE INVENTION

The present invention concerns at least the fields of molecular biology, cellular biology, and medicine. In particular, the field concerns modulating antiproliferative factor by affecting posttranslational modification of its receptor, wherein modulation relates to bladder conditions such as interstitial cystitis, in certain cases.

BACKGROUND OF THE INVENTION

Antiproliferative factor (APF) is a sialoglycopeptide inhibitor of bladder epithelial cell proliferation that is at least secreted specifically by bladder epithelial cells from patients with interstitial cystitis (IC) (Keay et al., 2004; Keay et al., 2000) a disorder commonly associated with denudation or thinning of the bladder epithelium (Skoluda et al., 1974; Matthews et al., 2001; Held et al., 1990). APF was discovered to be the active factor in urine from IC patients that reversibly inhibited the growth of bladder epithelial cells in vitro (Keay et al., 2000; Keay et al., 1996). The specificity of APF for urine from IC patients (vs. normal controls or patients with a variety of other urogenital disorders (Keay et al., 2001)) indicates that in certain aspects it is useful as a diagnostic marker for IC and that it may play an important role in the pathogenesis of this disorder.

APF is the first naturally occurring, low molecular weight negative growth regulator to have been identified and completely characterized. The peptide sequence of APF is identical to residues 541-549 of the 6th transmembrane domain of Frizzled 8, a Wnt ligand receptor. The glycosyl moiety of APF comprises sialic acid α-2,3 linked to galactose β1-3-N-acetylgalactosamine, which is α-O-linked to the N-terminal threonine residue of the nonapeptide 1.

APF has been shown to profoundly inhibit the proliferation of both normal bladder epithelial cells and bladder carcinoma cells in vitro (Keay et al., 2004; Keay et al., 2000; Keay et al., 1996). Furthermore, APF can induce multiple changes in the pattern of cellular gene expression including decreased production of heparin-binding epidermal growth factor-like growth factor (HB-EGF) and increased production of E-cadherin, resulting in a more differentiated bladder epithelial cell phenotype (Keay et al., 2000; Keay et al., 2003). APF was also recently determined to decrease tight junction protein (zonula occludens-1 and occludin) production and increase paracellular permeability of normal bladder epithelial cell monolayers similar to changes seen in cells from patients with IC in vitro (Zhang et al., 2005).

The potency of APF ($EC_{50}$ in the picomolar range), its varied effects on bladder epithelial cell protein expression and proliferation, and the requirement for a hexosamine-galactose disaccharide linked in a specific alpha configuration to the backbone peptide for activity (Keay et al., 2004; Keay et al., 2000; Zhang et al., 2005), all indicate that APF's effects are mediated by binding to and activating a receptor, for example. Microarray analysis indicated that there may be a role for specific transcription factors, such as AP-1, SP-1 and TCF/LEF-1, in abnormal gene expression in cells explanted from IC patients or following APF treatment of normal cells; this provides additional evidence for involvement of a receptor (Keay et al., 2003). Conrads et al. (2006) show that CKAP4/p63 is a receptor for the frizzled-8-protein-related antiproliferative factor from interstitial cystitis patients. Modulation of an APF receptor is useful for therapy/prevention of the effects of APF on the bladder epithelium.

SUMMARY OF THE INVENTION

The present invention is directed to systems, methods, and/or compositions that relate to antiproliferative factor (APF) activity. In specific aspects, the present invention concerns inhibiting the APF receptor, such as its enzymatic or other modification, for example, for the treatment of a bladder disorder, such as interstitial cystitis, for example.

In particular aspects of the invention, there are methods that affect the activity and/or function of an APF molecule by affecting the activity and/or intracellular distribution of a receptor for APF. In certain cases, the activity and/or function of an APF molecule is affected by affecting one or more post-translational modifications of a receptor for APF. In specific cases, affecting the activity and/or function of an APF molecule by affecting a post-translational modification of an APF receptor results in the improvement of at least one symptom of a bladder condition in an individual, and in certain cases the bladder condition is interstitial cystitis, for example.

In specific cases, post-translational modification of APF receptor is inhibited in an individual, such as by providing to the individual an agent that inhibits post-translational modification. The agent may comprise a nucleic acid; amino acid, such as a protein; small molecule; or mixture thereof, for example. In certain cases, the agent may comprise an antibody or inhibitory RNA, such as an siRNA, for example. The siRNA may be targeted against any part of a target mRNA, including a 5' leader, exon, intron, splice junction, or 3' UTR, for example, and in specific cases the target mRNA encodes an enzyme that post-translationally modifies the APF receptor. In some cases, there is a DNA construct for a dominant negative mutant PAT and/or the dominant negative mutant palmitoyl acyl transferases (PATs) itself.

Any post-translational modification of the APF receptor may be inhibited, such as, for example, palmitoylation, acetylation, alkylation, phosphorylation, farnesylation, methylation, biotinylation, glutamylation, glycylation, glycosylation, isoprenylation, lipoylation, phosphopantetheinylation, sulfation, selenation, nitrosylation, prenylation, C-terminal amidation, or a combination thereof. In specific cases, palmitoylation of an APF receptor is inhibited. Protein palmitoylation is the post-translational addition of the 16-carbon fatty acid, palmitate, to specific cysteine residues by a labile thioester linkage. Palmitoylation is mediated by a family of at least 23 PATs characterized by an AspHisHisCys (DHHC; SEQ ID NO:58) motif. Many palmitoylated proteins have been identified. Thus, in specific embodiments, APF receptor activity is modulated by inhibiting enzymatic addition of a palmitoyl group to the receptor.

In certain embodiments, the present invention affects binding of APF to its receptor, although in other embodiments the present invention affects availability of APF for its receptor. For example, decreased DHHC2 palmitoylation may not affect APF-receptor binding in some embodiments but may merely decrease cell membrane incorporation of the receptor, rendering it inaccessible for extracellular APF.

In specific embodiments of the invention, the APF receptor comprises CKAP4/p63, and in specific cases the APF receptor is present on bladder epithelial cells. In further specific embodiments, the receptor is palmitoylated by a PAT characterized by a DHHC motif, such as the cellular enzyme DHHC2, for example. In particular, embodiments inhibitory of ZDHHC2 or DHHC2 may be employed, such as antibodies to DHHC2 and/or siRNA knockdown of ZDHHC2, which results in cellular resistance to APF's antiproliferative effects, in specific cases.

In particular cases, inhibition of post-translational modification of an APF receptor ameliorates at least one symptom of a bladder condition, and in even further particular cases the bladder condition is interstitial cystitis (IC). Currently there are only two FDA-approved treatments for IC, oral Elmiron and intravesical DMSO, both of which help fewer than 50% of IC patients symptomatically. Because inhibition of cellular proliferation contributes to bladder epithelial thinning and ulceration seen in IC, in specific embodiments, in particular cases inhibition of zdhhc2 synthesis and/or activity is useful therapy for at least IC.

In certain embodiments of the invention, there is a method of modulating activity of antiproliferative factor in an individual, comprising delivering to the individual a therapeutically effective amount of an agent that modulates the activity of an APF receptor. In specific cases, the agent is further defined as an agent that inhibits post-translational modification of the APF receptor. In particular aspects, the agent inhibits palmitoylation of the APF receptor. In additional particular aspects, the agent inhibits a palmitoyl acyl transferase, such as DHHC2, or the gene that encodes it, ZDHHC2 for example.

In some embodiments, the agent is a nucleic acid, protein, small molecule, or a mixture thereof. In specific embodiments, the nucleic acid comprises siRNA. In additional aspects, the delivering step improves at least one symptom of a bladder condition. In certain cases the bladder condition is interstitial cystitis, and in particular embodiments the individual is further provided an additional interstitial cystitis therapy.

In another embodiment of the invention, there is a composition comprising an agent that inhibits post-translational modification of an APF receptor; and a pharmaceutically acceptable excipient. In certain embodiments, the composition is further defined as a nucleic acid, a polypeptide, a small molecule, or a mixture thereof. In some aspects, the composition is further defined as an inhibitory RNA, such as further defined as siRNA. In additional aspects, the composition further comprises an agent for treatment of a bladder condition, such as an agent for treatment of interstitial cystitis.

In an additional embodiment of the invention, there is a kit comprising one or more agents of the invention, wherein the agent is housed in a suitable container. The kit may further comprising an agent for treatment of a bladder condition, such as an agent for treatment of interstitial cystitis, in certain aspects of the invention.

In some embodiments of the invention, an inhibitor of CKAP4/p63 palmitoylation is employed for a use other than treatment of a bladder condition, for example, inhibition of tPA activity in smooth muscle or surfactant A activity in type II pneumocytes. Thus, in some embodiments of the invention, an individual is provided an inhibitor of CKAP4/p63 palmitoylation for the inhibition of tPA activity in smooth muscle, for example. In another embodiment of the invention, an individual is provided an inhibitor of CKAP4/p63 palmitoylation for inhibition of surfactant A activity in type II pneumocytes, for example. In additional embodiments, inhibition of APF activity is employed for stimulation of cell growth.

In additional embodiments of the invention, there is inhibition of palmitoylation of CKAP4/p63 for inhibition of molecules other than APF, given that it is an endogenous receptor for molecules other than APF. In specific embodiments, palmitoylation regulates the availability of CKAP4/p63 as a cell surface receptor for ligands other than APF.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

DETAILED DESCRIPTION OF THE INVENTION

Figure 1:
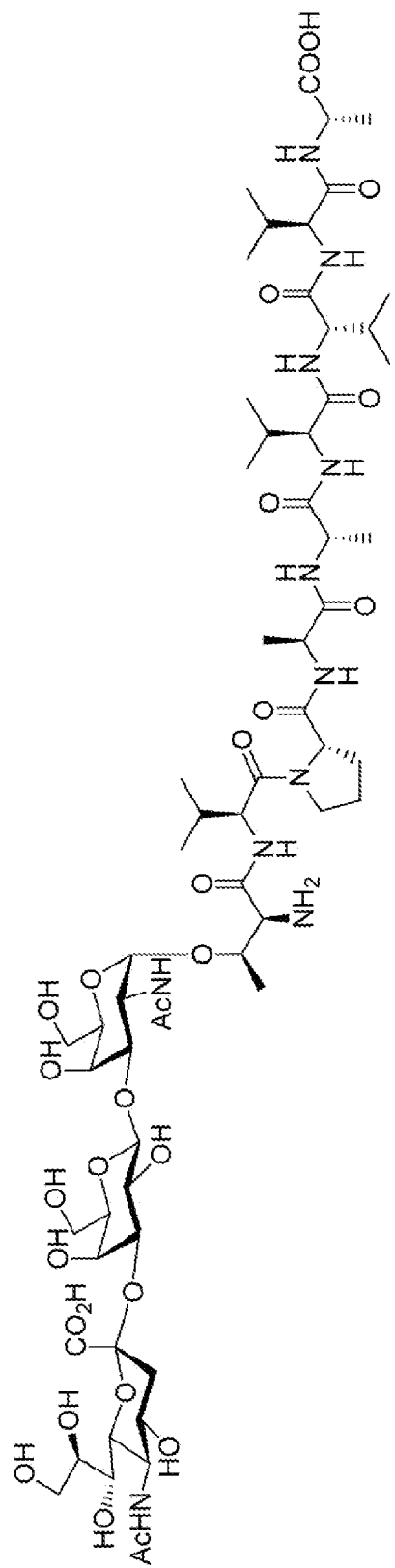
FIG. 1 illustrates an exemplary APF molecule.

The present invention incorporates by reference herein in their entirety U.S. patent application Ser. No. 10/882,586, filed Jul. 1, 2004; U.S. Provisional Patent Application Ser. No. 60/833,828, filed Jul. 27, 2006; U.S. patent application Ser. No. 11/743,865, filed May 3, 2007; and U.S. patent application Ser. No. 11/955,755, filed Dec. 13, 2007.

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

I. Definitions

The term "antiproliferative factor" as used herein refers to a molecule comprised of one or more sugar moieties and/or a hydrophobic moiety, wherein the molecule is characterized by the ability to inhibit cell proliferation. In specific embodiments, the inhibiting activity comprises inhibiting epithelial cell proliferation, such as bladder epithelial cell proliferation. In further specific embodiments, the hydrophobic moiety is a peptide. In specific embodiments, the hydrophobic nature facilitates nonspecific association with a membrane, or specific or nonspecific interaction with a hydrophobic pocket of a membrane receptor or cytoplasmic receptor, for example. The membrane may be any kind of membrane, although in particular aspects of the invention it is a plasma membrane. In further specific embodiments, the peptide is hydrophobic in part and comprises enough hydrophobicity to facilitate association of APF with a membrane.

The term "bladder disorder" as used herein refers to an abnormal condition of the urinary bladder, such as one in a mammal, including a human.

The term "palmitoylation" as used herein refers to the post-translational addition of the 16-carbon fatty acid, palmitate, to specific cysteine residues by a labile thioester linkage. In certain aspects, palmitoylation is reversible.

The term "urinary bladder" as used herein refers to a distensible membranous sac that serves for the temporary retention of the urine of an individual. Normally it resides in the pelvis in front of the rectum, and it receives the urine from the two ureters, discharging it at intervals into the urethra through an orifice closed by a sphincter. The organ is lined with transitional epithelium.

II. Embodiments of the Invention

Palmitoylation is the posttranslational addition of the 16-carbon palmitate group to specific cysteine residues of proteins (Smotrys and Linder, 2004) via a labile thioester bond. Unlike other forms of lipidation, such as myristoylation and prenylation, palmitoylation is reversible which allows for dynamic regulation of protein-membrane interactions, trafficking between membrane compartments (Zacharias et al., 2002; Wedegaertner and Bourne, 1994; Moran et al., 2001; Jones et al., 1997), and synaptic plasticity (el-Husseini and Bredt, 2002). For many years it was believed that palmitoylation occurred primarily by autocatalytic mechanisms (Bano et al., 1998; Bizzozero et al., 1987); however, the recent discovery of a family of palmitoyl acyl transferase (PAT) enzymes that catalyze protein palmitoylation has reversed this notion, expanding the complexity of the mechanisms by which palmitoylation is regulated (Lobo et al., 2002; Roth et al., 2002; Fukata et al., 2004; Linder and Deschenes, 2007).

PATs are encoded by the ZDHHC gene family and are characterized by an Asp-His-His-Cys motif (DHHC) within a cysteine-rich domain (CRD). The DHHC and CRD domains are essential for palmitoyl acyl transferase activity (Roth et al., 2002; Fukata et al., 2004). Twenty-three genes encoding proteins with DHHC-CRD domains have been identified in mouse and human databases (Fukata et al., 2004). Of these, at least six have been shown to be associated with human disease: DHHC8 with schizophrenia (mukai et al., 2004); DHHC17/HIP14 with Huntington's disease (Yanai et al., 2006); DHHC15 and DHHC9 with X-linked mental retardation (Mansouri et al., 2005; Raymond et al., 2007); and DHHC2 and DHHC11 with cancer (Oyama et al., 2000; Yamamoto et al., 2007). In many of these examples, the absence of PAT expression and subsequent failure to palmitoylate target substrates is the underlying problem.

Although now recognized as a PAT, DHHC2 was previously known as ream for reduced expression associated with metastasis. As the name suggests, this gene was first identified because its expression level was consistently and significantly reduced in clonal murine colorectal adenocarcinoma cell lines with high metastatic potential, but not in clonal lines derived from the same tumor that did not metastasize (Oyama et al., 2000; Tsuruo et al., 1983). It was concluded that ream expression is inversely related to the metastatic potential of a cell, leading to speculation that this gene normally suppresses one or more of the processes by which cancer cells escape from blood vessels, invade into and proliferate in a target organ, and induce angiogenesis and form metastatic foci.

Human ZDHHC2 maps to a region of chromosome 8 (p21.3-22) that is frequently deleted in many types of cancer, including colorectal (Fujiwara et al., 1993; Fujiwara et al., 1994; Ichii et al., 1993) hepatocellular carcinoma (Fujiwara et al., 1994; Emi et al., 1993), non-small cell lung (Fujiwara et al., 1993; Ohata et al., 1993), and cancers of the breast (Yaremko et al., 1996; Anbazhagan et al., 1998), urinary bladder (Knowles et al., 1993), and prostate (Bova et al., 1993). Loss of heterozygosity on chromosomal band 8p22 has been shown to be a common event in some epithelial tumors, pointing toward the likelihood that the region harbors potential tumor suppressor genes (Fujiwara et al., 1993; Ichii et al., 1993; Emi et al., 1993; Ohata et al., 1993)

Because DHHC2 has no other known signaling properties beyond palmitoylation, knowledge of its target substrates in a cancer cell line could yield significant clues about its role in metastasis and tumor suppression. A novel, proteomic method called PICA was utilized to identify the target substrates of DHHC2 in HeLa cells, a cervical adenocarcinoma cell line. It was determined that cytoskeletal associated protein 4 (CKAP4, also known as p63, ERGIC-63, and CLIMP-63) is a principle, physiologically important substrate of DHHC2 (Zhang et al., 2008).

CKAP4 is a reversibly palmitoylated, type II transmembrane protein that has been shown to anchor rough ER to microtubules in epithelial cells (ie, COS and HeLa) (Schweizer et al., 1995; Schweizer et al., 1993; Schweizer et al., 1994; Schweizer et al., 1993; Vedrenne and Hauri, 2006). This function requires a direct interaction between the cytoplasmic N-terminal tail of the protein to microtubules and is regulated by phosphorylation of three critical serine residues (Klopfenstein et al., 1998). More recently, CKAP4 has been identified as a functional cell surface receptor for antiproliferative factor (APF) (Conrads et al., 2006), a low molecular weight, Frizzled-8 protein-related sialoglycopeptide secreted from bladder epithelial cells in patients suffering from the chronic, painful bladder disorder, interstitial cystitis (IC) (Keay et al., 2000; Keay et al., 2004). APF profoundly inhibits normal bladder epithelial cell growth (Keay et al., 2000; Keay et al., 2004; Keay et al., 1996). APF also inhibits the proliferation of bladder carcinoma cells and HeLa cells in vitro with an IC50 of ~1 nM (Conrads et al., 2006; Keay et al., 2004; Keay et al., 2006). Binding of APF to CKAP4 results in internalization and subsequent nuclear localization, inhibition of cellular proliferation, and altered transcription of at least 13 genes known to be involved in the regulation of proliferation and tumorigenesis (including E-cadherin, vimentin, cyclin D1, p53 and ZO-1) (Conrads et al., 2006; Keay et al., 2003; Kim et al., 2007).

In the present invention, the effects of reduced CKAP4 palmitoylation on APF-mediated signaling were identified by silencing the expression of DHHC2 with targeted siRNA. The data show that DHHC2-mediated palmitoylation of CKAP4 is a critical event regulating APF-stimulated changes in cellular proliferation and gene expression, as well as APF-independent changes in cellular migration.

III. Receptor for Antiproliferative Factor (APF)

The present invention relates to modulation of a receptor for antiproliferative factor (APF), such as a receptor for an antiproliferative factor from bladder epithelial cells. In particular, the receptor comprises CKAP4/p63. The receptor may endogenously reside in a membrane of at least one type of cell, including an epithelial cell, such as, for example, a bladder cell, although in particular embodiments, there is a soluble form of the receptor.

As its receptor, APF may directly or indirectly bind CKAP4/p63. An exemplary CKAP4/p63 polypeptide is provided in SEQ ID NO:4 (National Center for Biotechnology Information GenBank® database's GenBank® Accession number AAH94824). An exemplary CKAP4/p63 polynucleotide is provided in SEQ ID NO:5 (GenBank® Accession number BC082972). Another exemplary CKAP4 polypeptide is provided in SEQ ID NO:6 (GenBank® Accession number NP_006816) and another exemplary CKAP4 polynucleotide is provided in SEQ ID NO:7 (GenBank® Accession number NM_006825). All GenBank® sequences are incorporated by reference herein in their entirety.

In some aspects, the receptor is modulated in its nucleic acid form (for example, by site-directed mutagenesis to generate a modified protein), although in other embodiments the receptor is modulated in its polypeptide form.

IV. Palmitoyl Acyl Transferases (PATs)

In a particular aspect of the invention, a palmitoyl acyl transferase is modulated, such as inhibited, so that the palmitoylation of APF receptor is affected, for example, thereby rendering the receptor unable to bind APF (or unable to traffic to and incorporate into the cell membrane, rendering it inaccessible for binding to extracellular APF, for example). Although any PAT may be targeted to affect APF receptor, in a specific embodiment, zinc finger, DHHC domain containing 2 (ZDHHC2 or DHHC2) is targeted. An exemplary nucleotide sequence for ZDHHC2 is comprised in SEQ ID NO:1 (National Center for Biotechnology Information's GenBank® database, Accession No. NM_016353). An exemplary amino acid sequence for DHHC2 is comprised in SEQ ID NO:2 (GenBank® database, Accession No. NP_057437.1).

Additional PATs that may be targeted in methods and compositions of the invention include DHHC1 (NP_037436.1; SEQ ID NO:10), which may be encoded by SEQ ID NO:11 (NM_013304); DHHC3 (NP_057682.1; SEQ ID NO:12), which may be encoded by SEQ ID NO:13 (NM_016598); DHHC4 (NP_060576.1; SEQ ID NO:14), which may be encoded by SEQ ID NO:15 (NM_018106.2); DHHC5 (NP_056272.2; SEQ ID NO:16), which may be encoded by SEQ ID NO:17 (NM_015457.2); DHHC6 (NP_071939.1; SEQ ID NO:18), which may be encoded by SEQ ID NO:19 (NM_022494.1); DHHC7 (NP_060210.1; SEQ ID NO:20), which may be encoded by SEQ ID NO:21 (NM_017740.1); DHHC8 (NP_037505.1; SEQ ID NO:22), which may be encoded by SEQ ID NO:23 (NM_013373.2); DHHC9 (NP_057116.2; SEQ ID NO:24), which may be encoded by SEQ ID NO:25 (NM_016032.2); DHHC11 (NP_079062.1; SEQ ID NO:26), which may be encoded by SEQ ID NO:27 (NM_024786.1); DHHC12 (NP_116188.2; SEQ ID NO:28), which may be encoded by SEQ ID NO:29 (NM_032799.4); DHHC13 (NP_061901.2; SEQ ID NO:30), which may be encoded by SEQ ID NO:31 (NM_019028.2); DHHC14 (NP_714968.1; SEQ ID NO:32), which may be encoded by SEQ ID NO:33 (NM_153746.1); DHHC15 (NP_659406.1; SEQ ID NO:34), which may be encoded by SEQ ID NO:35 (NM_144969); DHHC16 (NP_115703.2; SEQ ID NO:36), which may be encoded by SEQ ID NO:37 (NM_032327.2); DHHC17 (NP_056151.1; SEQ ID NO:38), which may be encoded by SEQ ID NO:39 (NM_015336.1); DHHC18 (NP_115659.1; SEQ ID NO:40), which may be encoded by SEQ ID NO:41 (NM_032283); DHHC19 (NP_653238.1; SEQ ID NO:42), which may be encoded by SEQ ID NO:43 (NM_144637.2); DHHC20 (NP_694983.2; SEQ ID NO:44), which may be encoded by SEQ ID NO:45 (NM_153251.2); DHHC21 (NP_848661.1; SEQ ID NO:46), which may be encoded by SEQ ID NO:47 (NM_178566.2);

DHHC22 (NP_777636.1; SEQ ID NO:48), which may be encoded by SEQ ID NO:49 (NM_174976.1); DHHC23 (NP_775841.2; SEQ ID NO:50), which may be encoded by SEQ ID NO:51 (NM_173570.2); and DHHC24 (NP_997223.1; SEQ ID NO:52), which may be encoded by SEQ ID NO:53 (NM_207340.1).

The PATs activity and/or expression may be targeted, and in specific cases the PATs are targeted by a nucleic acid, such as a siRNA; an amino acid, such as a protein, including an antibody; a small molecule; and/or a mixture thereof. The PATs may be targeted as polypeptides and/or as nucleic acids. The siRNA that targets the PAT may target any region of the PAT polynucleotide, but in specific embodiments, it targets the 5' untranslated region, an exon, an intron, the 3' untranslated region, or a combination thereof. In specific embodiment, there is a nucleic acid molecule, such as a RNA, that comprises a sequence complementary to any of the substrate sequences provided herein for modulation.

In some embodiments, there is a RNA molecule that down-regulates expression of a PAT gene, for example via RNA interference (RNAi), including dsRNA, siRNA, or shRNA. In some embodiments, the molecule 10, 11, 12, 13, 14, 15, 16, 17, 18, 19, 20, 21, 22, 23, 24, 25, 26, 27, or 28 or more nucleotides in length. In specific embodiments, the RNA molecule comprises nucleotide sequence having sufficient complementary to an RNA of a PAT gene. In specific embodiments, the complementarity is at least 70%, 75%, 80%, 85%, 90%, 95%, 97%, 99%, or 100% complementarity between the RNA and the target sequence.

In some embodiments, there is a method of inhibiting expression of a PAT comprising administering to a subject an effective amount of a short interfering ribonucleic acid (siRNA) comprising a sense RNA strand and an antisense RNA strand, wherein the sense and the antisense RNA strands form an RNA duplex, and wherein the sense RNA strand comprises a nucleotide sequence identical to a target sequence of about 10 to about 28 contiguous nucleotides in PAT mRNA. Methods and compositions analogous to those employed in the art may be utilized, as described in U.S. Pat. No. 6,818,447; U.S. Pat. No. 7,345,027; U.S. Pat. No. 7,022,828; and U.S. Pat. No. 6,617,438, all of which are incorporated by reference herein in their entirety.

V. Aantiproliferative Factor (APF)

The present invention encompasses compositions and methods associated with modulating a receptor for antiproliferative factor (APF). APF comprises a glycopeptide that at least inhibits proliferation of bladder epithelial cells, skin fibroblasts, and other epithelial cells including prostate cells, and in some embodiments it is generated by bladder epithelial cells, such as those associated with interstitial cystitis. In particular embodiments, the compound is present in the urine of individuals having interstitial cystitis. In other embodiments, the compound is generated or biosynthesized by tissues and cells other than urinary bladder tissue and cells. In one aspect of the invention, the compound is considered a toxin, a negative growth factor, or both.

APF was identified because of its ability to inhibit the growth of cells that line the bladder wall, in specific embodiments by altering the production of several proteins by these cells, such as specific growth factors and cell adhesion proteins. Not to be bound by any theory, in further embodiments APF causes interstitial cystitis in which the bladder lining is generally thin and/or ulcerated.

Thus, as used herein the term "APF" refers to a class of compounds wherein the structure in FIG. 1 is merely the prototypical APF and other related compositions are encompassed as a ligand for the receptor of the invention. Although in particular aspects of the invention APF comprises the structure provided in FIG. 1, this is merely one embodiment of a ligand for the receptor that is modulated for the invention. A skilled artisan recognizes that the structure in FIG. 1 may bind a receptor of the invention, although in some embodiments a similar but non-identical structure of APF binds the receptor of the invention; the binding of the similar but non-identical structure of APF may be in addition to or instead of the binding of the structure in FIG. 1 to the receptor. APF compositions that may be affected by modulating the receptor herein include both isolated natural APF, synthetic versions thereof, derivatives thereof, or a mixture thereof.

Thus, in specific embodiments, APF compositions comprise about one to about six sugar residues and a peptide of about two to about fifteen amino acid residues, wherein the peptide-linked to one of the sugar moieties at a linking amino acid, wherein the linking amino acid comprises a heteroatom that serves as the linking portion of the linking amino acid. More specifically, the linking amino acid comprises a serine, a threonine, or a cysteine. In other specific embodiments, the compositions of the present invention comprises two or three sugar residues and nine amino acids and the linking amino acid is a threonine or serine.

In one specific aspect of the invention, APF is an acidic, heat stable sialoglycopeptide comprising 9 amino acid residues (such as, for example, TVPAAVVVA, SEQ ID NO:6; SVPAAVVVA, SEQ ID NO:7; TVPAAVVLA, SEQ ID NO:8; or SLPAAVVVA, SEQ ID NO:9) covalently linked through the N-terminal threonine, serine, or cysteine, for example, to an N-acetylgalactosamine or N-acetylglucosamine residue that is linked via an α- or β-configuration to galactose, and sialylated on the galactose moiety via 2,3 linkage. The anomeric configuration of the glycosyl bond is alpha in particular embodiments, although it may be beta in alternative embodiments.

In one particular aspect of the invention, an APF composition may comprise in part a hydrophobic moiety, such as a peptide, for example one including SEQ ID NO:6, SEQ ID NO:7, SEQ ID NO:8, SEQ ID NO:9; or a lipid. The peptide may comprise at least part of a transmembrane domain, and in particular embodiments it comprises part of frizzled 8, such as a transmembrane domain of frizzled 8. In specific embodiments, the peptide is hydrophobic.

The glycoprotein comprising a galactose covalently linked to an N-acetylglucosamine or an N-acetylgalactosamine covalently linked to a peptide of SEQ ID NO:6 or variants thereof is provided herein. The term "variants thereof" includes peptidomimetics of various types (Ahn et al., 2002). The peptides may comprise any suitable amino acids, such as L-amino acids, D-amino acids, N-methylated amino acids, or a combination thereof, as well as peptidomimetic compounds such as unnatural amino acids or other "peptide-like" organic constructs that mimic the specific structural elements of a linear, cyclic, or branched peptide that correspond to active peptides. The sugar moieties may be natural, synthetic, carbohydratemimetic, or a mixture thereof may be used in a composition. Glycopeptidomimetic compounds where the sugars are carbohydratemimetic moieties or the peptide components are peptidomimetic moieties, or a combination of the two, are encompassed in the invention. In specific embodiments, the sugars of the present invention include amino sugars.

In a particular aspect of the invention, the APF has a molecular mass of 1482.8 and comprises nine amino acids and three sugar moieties in the following order: (a) Sialic acid-galactose-N-acetylgalactosamine-threonine-valine-proline-alanine-alanine-valine-valine-valine-alanine; or (b) Sialic acid-galactose-Nacetylglucosamine-threonine-valine-proline-alanine-alanine-valine-valine-valine-alanine; or (c) Sialic acid-galactose-N-acetylglucosamine-serine-leucine-proline-alanine-alanine-valine-valine-valine-alanine. The composition may be further defined as having one or more of the following: the sialic acid in (a) is linked to galactose via a 2,3 linkage; the sialic acid in (b) is linked to galactose via a 2,3 linkage; the sialic acid in (c) is linked to galactose via a 2,3 linkage; the galactose in (a) is linked to the N-acetylgalactosamine via a 1,3 linkage; the galactose in (b) is linked to the N-acetylglucosamine via a 1,4 linkage; the galactose in (c) is linked to the N-acetylglucosamine via a 1,4 linkage; the N-acetylglucosamine is linked to serine via an O linkage in an alpha configuration; or the N-acetylgalactosamine is linked to threonine or serine via an O linkage in an alpha configuration.

Certain APF compounds related to the present invention comprise a threonine, a serine, or a cysteine at the N-terminus or any functional equivalent. Non-limiting examples of functional equivalents include a synthetic derivative having a primary or secondary or tertiary alcohol, an ester, a carboxylic acid, an ether, a thiol, a thiolate, or any functional group enabling for covalent linkage with a sugar molecule, provided the molecule retains biological function.

Other functionalities contemplated in "derivatives" of the present invention include isomers of any of the sugars or amino acids, whether positional, structural, or stereoisomers. Other substituents known to those skilled in the chemical arts may be present, so long as the biological function of the molecule is retained, in specific embodiments of the invention.

VI. siRNAs

The present invention provides an interfering RNA that silences (e.g., partially or completely inhibits) expression of a gene of interest (i.e., a PAT gene). An interfering RNA can be provided in several forms. For example, an interfering RNA can be provided as one or more isolated small-interfering RNA (siRNA) duplexes, longer double-stranded RNA (dsRNA), or as siRNA or dsRNA transcribed from a transcriptional cassette in a DNA plasmid. The interfering RNA may also be chemically synthesized. The interfering RNA can be administered alone or co-administered (i.e., concurrently or consecutively) with conventional agents used to treat a bladder infection.

In one aspect, the interfering RNA is an siRNA molecule that is capable of silencing expression of a target sequence such as a PAT sequence. In some embodiments, the siRNA molecules are about 15 to 60 nucleotides in length. The synthesized or transcribed siRNA can have 3' overhangs of about 1-4 nucleotides, preferably of about 2-3 nucleotides, and 5' phosphate termini. In some embodiments, the siRNA lacks terminal phosphates.

In certain embodiments, the siRNA molecules of the present invention are chemically modified as described herein. In certain preferred embodiments, the siRNA molecules of the present invention comprise less than about 20% modified nucleotides. The modified siRNA molecule is notably less immunostimulatory than a corresponding unmodified siRNA sequence and retains full RNAi activity against the target sequence, in certain embodiments. Preferably, the modified siRNA contains at least one 2'OMe purine or pyrimidine nucleotide such as a 2'OMe-guanosine, 2'OMe-uridine, 2'OMe-adenosine, and/or 2'OMe-cytosine nucleotide.

The modified nucleotides can be present in one strand (i.e., sense or antisense) or both strands of the siRNA.

Importantly, siRNA molecules that are immunostimulatory can be modified to decrease their immunostimulatory properties without having a negative impact on RNAi activity. For example, an immunostimulatory siRNA can be modified by replacing one or more nucleotides in the sense and/or antisense strand with a modified nucleotide, thereby generating a modified siRNA with reduced immunostimulatory properties that is still capable of silencing expression of the target sequence. In preferred embodiments, one or more of the uridine and/or guanosine nucleotides are modified. Preferably, the modified nucleotide is a 2'OMe nucleotide such as a 2'OMe-guanosine, 2'OMe-uridine, and/or 2'OMe-adenosine nucleotide.

It is also preferred that the modified siRNA comprises less than about 20% modified nucleotides (e.g., less than about 20%, 19%, 18%, 17%, 16%, 15%, 14%, 13%, 12%, 11%, 10%, 9%, 8%, 7%, 6%, 5%, 4%, 3%, 2%, or 1% modified nucleotides) or between about 1%-20% modified nucleotides (e.g., between about 1%-20%, 2%-20%, 3%-20%, 4%-20%, 5%-20%, 6%-20%, 7%-20%, 8%-20%, 9%-20%, 10%-20%, 11%-20%, 12%-20%, 13%-20%, 14%-20%, 15-20%, 16%-20%, 17%-20%, 18%-20%, or 19%-20% modified nucleotides). However, when one or both strands of the siRNA are selectively modified at uridine and/or guanosine nucleotides, the resulting modified siRNA molecule can comprise less than about 25% modified nucleotides (e.g., less than about 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% modified nucleotides) or between about 1%-25% modified nucleotides (e.g., between about 1%-25%, 2%-25%, 3%-25%, 4%-25%, 5%-25%, 6%-25%, 7%-25%, 8%-25%, 9%-25%, 10%-25%, 11%-25%, 12%-25%, 13%-25%, 14%-25%, 15-25%, 16%-25%, 17%-25%, 18%-25%, 19%-25%, 20%-25%, 21%-25%, 22%-25%, 23%-25%, or 24%-25% modified nucleotides).

A. Selection of siRNA Sequences

Suitable siRNA sequences can be identified using any means known in the art. Typically, the methods described in Elbashir et al., Nature, 411:494-498 (2001) and Elbashir et al., EMBO J, 20:6877-6888 (2001) are combined with rational design rules set forth in Reynolds et al., Nature Biotech., 22(3):326-330 (2004), for example.

In some cases, the sequence within about 50 to about 100 nucleotides 3' of the AUG start codon of a transcript from the target gene of interest is scanned for dinucleotide sequences (e.g., AA, NA, CC, GG, or UU, wherein N=C, G, or U) (see, e.g., Elbashir et al., EMBO J. 20:6877-6888 (2001)). The nucleotides immediately 3' to the dinucleotide sequences are identified as potential siRNA target sequences. Typically, the 19, 21, 23, 25, 27, 29, 31, 33, 35, or more nucleotides immediately 3' to the dinucleotide sequences are identified as potential siRNA target sites. In some embodiments, the dinucleotide sequence is an AA or NA sequence and the 19 nucleotides immediately 3' to the AA or NA dinucleotide are identified as a potential siRNA target site. siRNA target sites are usually spaced at different positions along the length of the target gene. To further enhance silencing efficiency of the siRNA sequences, potential siRNA target sites may be analyzed to identify sites that do not contain regions of homology to other coding sequences, e.g., in the target cell or organism. For example, a suitable siRNA target site of about 21 base pairs typically will not have more than 16-17 contiguous base pairs of homology to coding sequences in the target cell or organism. If the siRNA sequences are to be expressed from an RNA Pol III promoter, siRNA target sequences lacking more than 4 contiguous A's or T's are selected.

Once a potential siRNA sequence has been identified, the sequence can be analyzed using a variety of criteria known in the art. For example, to enhance their silencing efficiency, the siRNA sequences may be analyzed by a rational design algorithm to identify sequences that have one or more of the following features: (1) G/C content of about 25% to about 60% G/C; (2) at least 3 A/Us at positions 15-19 of the sense strand; (3) no internal repeats; (4) an A at position 19 of the sense strand; (5) an A at position 3 of the sense strand; (6) a U at position 10 of the sense strand; (7) no G/C at position 19 of the sense strand; and (8) no G at position 13 of the sense strand. siRNA design tools that incorporate algorithms that assign suitable values of each of these features and are useful for selection of siRNA can be found on the world wide web. One of skill in the art will appreciate that sequences with one or more of the foregoing characteristics may be selected for further analysis and testing as potential siRNA sequences. siRNA sequences complementary to the siRNA target sites may also be designed.

Additionally, potential siRNA target sequences with one or more of the following criteria can often be eliminated as siRNA, in some embodiments: (1) sequences comprising a stretch of 4 or more of the same base in a row; (2) sequences comprising homopolymers of Gs (i.e., to reduce possible non-specific effects due to structural characteristics of these polymers; (3) sequences comprising triple base motifs (e.g., GGG, CCC, AAA, or TTT); (4) sequences comprising stretches of 7 or more G/Cs in a row; and (5) sequences comprising direct repeats of 4 or more bases within the candidates resulting in internal fold-back structures. However, one of skill in the art will appreciate that sequences with one or more of the foregoing characteristics may still be selected for further analysis and testing as potential siRNA sequences.

In some embodiments, potential siRNA target sequences may be further analyzed based on siRNA duplex asymmetry as described in, e.g., Khvorova et al., Cell, 115:209-216 (2003); and Schwarz et al., Cell, 115:199-208 (2003). In other embodiments, potential siRNA target sequences may be further analyzed based on secondary structure at the mRNA target site as described in, e.g., Luo et al., Biophys. Res. Commun., 318:303-310 (2004). For example, mRNA secondary structure can be modeled using the Mfold algorithm (available at Rensselaer bioinformatics web server on the world wide web, for example) to select siRNA sequences which favor accessibility at the mRNA target site where less secondary structure in the form of base-pairing and stem-loops is present.

Once a potential siRNA sequence has been identified, the sequence can be analyzed for the presence of any immunostimulatory properties, e.g., using an in vitro cytokine assay or an in vivo animal model. Motifs in the sense and/or antisense strand of the siRNA sequence such as GU-rich motifs can also provide an indication of whether the sequence may be immunostimulatory. Once an siRNA molecule is found to be immunostimulatory, it can then be modified to decrease its immunostimulatory properties as described herein. As a non-limiting example, an siRNA sequence can be contacted with a mammalian responder cell under conditions such that the cell produces a detectable immune response to determine whether the siRNA is an immunostimulatory or a non-immunostimulatory siRNA. The mammalian responder cell may be from a naive mammal (i.e., a mammal that has not previously been in contact with the gene product of the siRNA sequence). The mammalian responder cell may be, e.g., a peripheral blood mononuclear cell (PBMC), a macrophage, and the like. The detectable immune response may comprise production of a cytokine or growth factor such as, e.g., TNF-α, TNF-β, IFN-α, IFN-γ, IL-6, IL-12, or a combination thereof. An siRNA molecule identified as being immunostimulatory can then be modified to decrease its immunostimulatory properties by replacing at least one of the nucleotides on the sense and/or antisense strand with modified nucleotides. For example, less than about 20% of the nucleotides in the siRNA duplex can be replaced with modified nucleotides such as 2'OMe nucleotides. The modified siRNA can then be contacted with a mammalian responder cell as described above to confirm that its immunostimulatory properties have been reduced or abrogated.

Suitable in vitro assays for detecting an immune response include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., Radioimmunoassay Methods, E. and S. Livingstone, Edinburgh (1970)); the "Western blot" method of Gordon et al. (U.S. Pat. No. 4,452,901); immunoprecipitation of labeled ligand (Brown et al., J. Biol. Chem., 255:4980-4983 (1980)); enzyme-linked immunosorbent assays (ELISA) as described, for example, by Raines et al., J. Biol. Chem., 257:5154-5160 (1982); immunocytochemical techniques, including the use of fluorochromes (Brooks et al., Clin. Exp. Immunol., 39:477 (1980)); and neutralization of activity (Bowen-Pope et al., Proc. Natl. Acad. Sci. USA, 81:2396-2400 (1984)). In addition to the immunoassays described above, a number of other immunoassays are available, including those described in U.S. Pat. Nos. 3,817,827; 3,850,752; 3,901,654; 3,935,074; 3,984,533; 3,996,345; 4,034,074; and 4,098,876.

A non-limiting example of an in vivo model for detecting an immune response includes an in vivo mouse cytokine induction assay that can be performed as follows: (1) siRNA can be administered by standard intravenous injection in the lateral tail vein; (2) blood can be collected by cardiac puncture about 6 hours after administration and processed as plasma for cytokine analysis; and (3) cytokines can be quantified using sandwich ELISA kits according to the manufacturers' instructions (e.g., mouse and human IFN-.alpha. (PBL Biomedical; Piscataway, N.J.); human IL-6 and TNF-α (eBioscience; San Diego, Calif.); and mouse IL-6, TNF-.alpha., and IFN-γ. (BD Biosciences; San Diego, Calif.)).

Monoclonal antibodies that specifically bind cytokines and growth factors are commercially available from multiple sources and can be generated using methods known in the art (see, e.g., Kohler and Milstein, Nature, 256: 495-497 (1975); and Harlow and Lane, ANTIBODIES, A LABORATORY MANUAL, Cold Spring Harbor Publication, New York (1999)). Generation of monoclonal antibodies has been previously described and can be accomplished by any means known in the art (see, e.g., Buhring et al. in Hybridoma, Vol. 10, No. 1, pp. 77-78 (1991)). In some methods, the monoclonal antibody is labeled (e.g., with any composition detectable by spectroscopic, photochemical, biochemical, electrical, optical, chemical means, and the like) to facilitate detection.

B. Generating siRNA siRNA molecules can be provided in several forms including, e.g., as one or more isolated small-interfering RNA (siRNA) duplexes, as longer double-stranded RNA (dsRNA), or as siRNA or dsRNA transcribed from a transcriptional cassette in a DNA plasmid. The siRNA sequences may have overhangs (e.g., 3' or 5' overhangs as described in Elbashir et al., Genes Dev., 15:188 (2001) or Nykanen et al., Cell, 107: 309 (2001), or may lack overhangs (i.e., have blunt ends).

An RNA population can be used to provide long precursor RNAs, or long precursor RNAs that have substantial or complete identity to a selected target sequence can be used to make the siRNA. The RNAs can be isolated from cells or tissue, synthesized, and/or cloned according to methods well known to those of skill in the art. The RNA can be a mixed population (obtained from cells or tissue, transcribed from cDNA, subtracted, selected, etc.), or can represent a single target sequence. RNA can be naturally occurring (e.g., isolated from tissue or cell samples), synthesized in vitro (e.g., using T7 or SP6 polymerase and PCR products or a cloned cDNA), or chemically synthesized.

To form a long dsRNA, for synthetic RNAs, the complement is also transcribed in vitro and hybridized to form a dsRNA. If a naturally occurring RNA population is used, the RNA complements are also provided (e.g., to form dsRNA for digestion by *E. coli* RNAse III or Dicer), e.g., by transcribing cDNAs corresponding to the RNA population, or by using RNA polymerases. The precursor RNAs are then hybridized to form double stranded RNAs for digestion. The dsRNAs can be directly administered to a subject or can be digested in vitro prior to administration.

Alternatively, one or more DNA plasmids encoding one or more siRNA templates are used to provide siRNA. siRNA can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (see, Brummelkamp et al., Science, 296:550 (2002); Donze et al., Nucleic Acids Res., 30:e46 (2002); Paddison et al., Genes Dev., 16:948 (2002); Yu et al., Proc. Natl. Acad. Sci. USA, 99:6047 (2002); Lee et al., Nat. Biotech., 20:500 (2002); Miyagishi et al., Nat. Biotech., 20:497 (2002); Paul et al., Nat. Biotech., 20:505 (2002); and Sui et al., Proc. Natl. Acad. Sci. USA, 99:5515 (2002)). Typically, a transcriptional unit or cassette will contain an RNA transcript promoter sequence, such as an H1-RNA or a U6 promoter, operably linked to a template for transcription of a desired siRNA sequence and a termination sequence, comprised of 2-3 uridine residues and a polythymidine (T5) sequence (polyadenylation signal) (Brummelkamp et al., supra). The selected promoter can provide for constitutive or inducible transcription. Compositions and methods for DNA-directed transcription of RNA interference molecules is described in detail in U.S. Pat. No. 6,573,099. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488. The selected plasmid can provide for transient or stable delivery of a target cell. It will be apparent to those of skill in the art that plasmids originally designed to express desired gene sequences can be modified to contain a transcriptional unit cassette for transcription of siRNA.

Methods for isolating RNA, synthesizing RNA, hybridizing nucleic acids, making and screening cDNA libraries, and performing PCR are well known in the art (see, e.g., Gubler and Hoffman, Gene 25:263-269 (1983); Sambrook et al., supra; Ausubel et al., supra), as are PCR methods (see, U.S. Pat. Nos. 4,683,195 and 4,683,202; PCR Protocols: A Guide to Methods and Applications (Innis et al., eds, 1990)). Expression libraries are also well known to those of skill in the art. Additional basic texts disclosing the general methods of use in this invention include Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994).

In some cases, siRNA are chemically synthesized. The oligonucleotides that comprise the siRNA molecule can be synthesized using any of a variety of techniques known in the art, such as those described in Usman et al., J. Am. Chem. Soc., 109:7845 (1987); Scaringe et al., Nuc. Acids Res., 18:5433 (1990); Wincott et al., Nuc. Acids Res., 23:2677-2684 (1995); and Wincott et al., Methods Mol. Bio., 74:59 (1997). The synthesis of oligonucleotides makes use of common nucleic acid protecting and coupling groups, such as dimethoxytrityl at the 5'-end and phosphoramidites at the 3'-end. As a non-limiting example, small scale syntheses can be conducted on an Applied Biosystems synthesizer using a 0.2 .mu.mol scale protocol with a 2.5 min. coupling step for 2'-O-methylated nucleotides. Alternatively, syntheses at the 0.2 .mu.mol scale can be performed on a 96-well plate synthesizer from Protogene (Palo Alto, Calif.). However, a larger or smaller scale of synthesis is also within the scope of the present invention. Suitable reagents for oligonucleotide synthesis, methods for RNA deprotection, and methods for RNA purification are known to those of skill in the art.

The siRNA molecules can also be synthesized via a tandem synthesis technique, wherein both strands are synthesized as a single continuous oligonucleotide fragment or strand separated by a cleavable linker that is subsequently cleaved to provide separate fragments or strands that hybridize to form the siRNA duplex. The linker can be a polynucleotide linker or a non-nucleotide linker. The tandem synthesis of siRNA can be readily adapted to both multiwell/multiplate synthesis platforms as well as large scale synthesis platforms employing batch reactors, synthesis columns, and the like. Alternatively, the siRNA molecules can be assembled from two distinct oligonucleotides, wherein one oligonucleotide comprises the sense strand and the other comprises the antisense strand of the siRNA. For example, each strand can be synthesized separately and joined together by hybridization or ligation following synthesis and/or deprotection. In certain other instances, the siRNA molecules can be synthesized as a single continuous oligonucleotide fragment, where the self-complementary sense and antisense regions hybridize to form an siRNA duplex having hairpin secondary structure.

C. Modifying siRNA Sequences

In certain aspects, the siRNA molecules of the present invention comprise a duplex having two strands and at least one modified nucleotide in the sense and/or antisense strand, wherein each strand is about 15 to about 60 nucleotides in length. In some embodiments, the siRNA molecules described herein comprise less than about 20% modified nucleotides (e.g., less than about 20%, 15%, 10%, or 5% modified nucleotides) or between about 1%-20% modified nucleotides (e.g., between about 1%-20%, 5%-20%, 10%-20%, or 15-20% modified nucleotides). Preferably, the modified siRNA contains less than about 20% or between about 1%-20% of 2'OMe purine and/or pyrimidine nucleotides such as a 2'OMe-guanosine, 2'OMe-uridine, 2'OMe-adenosine, and/or 2'OMe-cytosine nucleotide. In certain preferred embodiments, one or more of the uridine and/or guanosine nucleotides are modified in the siRNA sequence. Advantageously, the modified siRNA is less immunostimulatory than a corresponding unmodified siRNA sequence, but retains the capability of silencing the expression of a target sequence.

Examples of modified nucleotides suitable for use in the present invention include, but are not limited to, ribonucleotides having a 2'-O-methyl (2'OMe), 2'-deoxy-2'-fluoro, 2'-deoxy, 5-C-methyl, 2'-methoxyethyl, 4'-thio, 2'-amino, or 2'-C-allyl group. Modified nucleotides having a Northern conformation such as those described in, e.g., Saenger, Principles of Nucleic Acid Structure, Springer-Verlag Ed. (1984), are also suitable for use in the siRNA molecules of the present invention. Such modified nucleotides include, without limitation, locked nucleic acid (LNA) nucleotides (e.g., 2'-O,4'-C-methylene-(D-ribofuranosyl) nucleotides), 2'-methoxyethoxy (MOE) nucleotides, 2'-methyl-thio-ethyl nucleotides, 2'-deoxy-2'-fluoro nucleotides, 2'-deoxy-2'-chloro nucleotides, and 2'-azido nucleotides. In certain instances, the siRNA molecule includes one or more G-clamp nucleotides. A G-clamp nucleotide refers to a modified cytosine analog wherein the modifications confer the ability to hydrogen bond both Watson-Crick and Hoogsteen faces of a complementary guanine nucleotide within a duplex (see, e.g., Lin et al., J. Am. Chem. Soc., 120:8531-8532 (1998)). In addition, nucleotides having a nucleotide base analog such as, for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (see, e.g., Loakes, Nucl. Acids Res., 29:2437-2447 (2001)) can be incorporated into the siRNA molecule.

In certain embodiments, the siRNA molecule can comprise one or more chemical modifications such as terminal cap moieties, phosphate backbone modifications, and the like. Examples of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, .alpha.-nucleotides, modified base nucleotides, threo-pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-aminoalkyl phosphate, 1,3-diamino-2-propyl phosphate, 3-aminopropyl phosphate, 6-aminohexyl phosphate, 1,2-aminododecyl phosphate, hydroxypropyl phosphate, 1,4-butanediol phosphate, 3'-phosphoramidate, 5'-phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al., Tetrahedron, 49:1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al., Nucleic Acid Analogues: Synthesis and Properties, in Modern Synthetic Methods, VCH, 331-417 (1995); Mesmaeker et al., Novel Backbone Replacements for Oligonucleotides, in Carbohydrate Modifications in Antisense Research, ACS, 24-39 (1994)). Such chemical modifications can occur at the 5'-end and/or 3'-end of the sense strand, antisense strand, or both strands of the siRNA.

In some embodiments, the sense and/or antisense strand can comprise a 3'-terminal overhang having about 1 to about 4 (e.g., 1, 2, 3, or 4) 2'-deoxy ribonucleotides and/or any combination of modified and unmodified nucleotides. Additional examples of modified nucleotides and types of chemical modifications that can be introduced into the modified siRNA molecule are described, e.g., in UK Patent No. GB 2,397,818 B and U.S. Patent Publication Nos. 20040192626 and 20050282188.

The siRNA molecules described herein can optionally comprise one or more non-nucleotides in one or both strands of the siRNA. As used herein, the term "non-nucleotide" refers to any group or compound that can be incorporated into a nucleic acid chain in the place of one or more nucleotide units, including sugar and/or phosphate substitutions, and allows the remaining bases to exhibit their activity. The group or compound is abasic in that it does not contain a commonly recognized nucleotide base such as adenosine, guanine, cytosine, uracil, or thymine and therefore lacks a base at the 1'-position.

In other embodiments, chemical modification of the siRNA comprises attaching a conjugate to the siRNA molecule. The conjugate can be attached at the 5' and/or 3'-end of the sense and/or antisense strand of the siRNA via a covalent attachment such as, e.g., a biodegradable linker. The conjugate can also be attached to the siRNA, e.g., through a carbamate group or other linking group (see, e.g., U.S. Patent Publication Nos. 20050074771, 20050043219, and 20050158727). In certain instances, the conjugate is a molecule that facilitates the delivery of the siRNA into a cell. Examples of conjugate molecules suitable for attachment to an siRNA include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Yet other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples include the hydrophobic group, membrane active compound, cell penetrating compound, cell targeting signal, interaction modifier, and steric stabilizer conjugate molecules described in U.S. Patent Publication No. 20040167090. Further examples include the conjugate molecules described in U.S. Patent Publication No. 20050239739. The type of conjugate used and the extent of conjugation to the siRNA molecule can be evaluated for improved pharmacokinetic profiles, bioavailability, and/or stability of the siRNA. As such, one skilled in the art can screen siRNA molecules having various conjugates attached thereto to identify ones having improved properties using any of a variety of well-known in vitro cell culture or in vivo animal models.

VII. Carrier Systems Containing siRNA

In one aspect, the present invention provides carrier systems containing the siRNA molecules described herein. In some embodiments, the carrier system is a lipid-based carrier system such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex. In further embodiments, the carrier system is a protein-based carrier system such as a cationic peptide-nucleic acid complex. Preferably, the carrier system is a stabilized nucleic acid-lipid particle such as a SNALP or SPLP. One skilled in the art will appreciate that the siRNA molecule of the present invention can also be delivered as a naked siRNA molecule, in some cases.

A. Stabilized Nucleic Acid-Lipid Particles

The stabilized nucleic acid-lipid particles (SNALPs) of the present invention typically comprise an siRNA molecule that targets expression of a PAT gene (e.g., an Ebola virus or Marburg virus gene), a cationic lipid, and a non-cationic lipid. The SNALPs can further comprise a bilayer stabilizing component (i.e., a conjugated lipid that inhibits aggregation of the particles).

The SNALPs of the present invention typically have a mean diameter of about 50 nm to about 150 nm, more typically about 60 nm to about 130 nm, more typically about 70 nm to about 110 nm, most typically about 70 to about 90 nm, and are substantially nontoxic. In addition, the nucleic acids are resistant in aqueous solution to degradation with a nuclease when present in the nucleic acid-lipid particles. Nucleic acid-lipid particles and their method of preparation are disclosed in, e.g., U.S. Pat. Nos. 5,753,613; 5,785,992; 5,705,385; 5,976,567; 5,981,501; 6,110,745; and 6,320,017; and PCT Publication No. WO 96/40964.

1. Cationic Lipids

Any of a variety of cationic lipids may be used in the stabilized nucleic acid-lipid particles of the present invention, either alone or in combination with one or more other cationic lipid species or non-cationic lipid species.

Cationic lipids which are useful in the present invention can be any of a number of lipid species which carry a net positive charge at physiological pH. Such lipids include, but are not limited to, DODAC, DODMA, DSDMA, DOTMA, DDAB, DOTAP, DOSPA, DOGS, DC-Chol, DMRIE, and mixtures thereof. A number of these lipids and related analogs have been described in U.S. Patent Publication No. 20060083780; U.S. Pat. Nos. 5,208,036; 5,264,618; 5,279,833; 5,283,185; and 5,753,613; and 5,785,992; and PCT Publication No. WO 96/10390. Additionally, a number of commercial preparations of cationic lipids are available and can be used in the present invention. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic liposomes comprising DOGS from Promega Corp., Madison, Wis., USA).

Other cationic lipids may be employed as carriers, as described in U.S. Patent Publication No. 20070135370, which is incorporated by reference herein in its entirety.

2. Non-Cationic Lipids

The non-cationic lipids used in the stabilized nucleic acid-lipid particles of the present invention can be any of a variety of neutral uncharged, zwitterionic, or anionic lipids capable of producing a stable complex. They are preferably neutral, although they can alternatively be positively or negatively charged. Examples of non-cationic lipids include, without limitation, phospholipid-related materials such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), and stearoyloleoyl-phosphatidylethanolamine (SOPE). Non-cationic lipids or sterols such as cholesterol may also be present. Additional nonphosphorous containing lipids include, e.g., stearylamine, dodecylamine, hexadecylamine, acetyl palmitate, glycerolricinoleate, hexadecyl stereate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, diacylphosphatidylcholine, diacylphosphatidylethanolamine, and the like. Other lipids such as lysophosphatidylcholine and lysophosphatidylethanolamine may be present. Non-cationic lipids also include polyethylene glycol-based polymers such as PEG 2000, PEG 5000, and polyethylene glycol conjugated to phospholipids or to ceramides (referred to as PEG-Cer), as described in U.S. patent application Ser. No. 08/316,429.

In preferred embodiments, the non-cationic lipids are diacylphosphatidylcholine (e.g., distearoylphosphatidylcholine, dioleoylphosphatidylcholine, dipalmitoylphosphatidylcholine, and dilinoleoylphosphatidylcholine), diacylphosphatidylethanolamine (e.g., dioleoylphosphatidylethanolamine and palmitoyloleoyl-phosphatidylethanolamine), ceramide, or sphingomyelin. The acyl groups in these lipids are preferably acyl groups derived from fatty acids having $C_{10}$-$C_{24}$ carbon chains. More preferably, the acyl groups are lauroyl, myristoyl, palmitoyl, stearoyl, or oleoyl. In particularly preferred embodiments, the non-cationic lipid includes one or more of cholesterol, DOPE, or ESM.

The non-cationic lipid typically comprises from about 5 mol % to about 90 mol %, from about 10 mol % to about 85 mol %, from about 20 mol % to about 80 mol %, or about 20 mol % of the total lipid present in the particle. The particles may further comprise cholesterol. If present, the cholesterol typically comprises from about 0 mol % to about 10 mol %, from about 2 mol % to about 10 mol %, from about 10 mol % to about 60 mol %, from about 12 mol % to about 58 mol %, from about 20 mol % to about 55 mol %, from about 30 mol % to about 50 mol %, or about 48 mol % of the total lipid present in the particle.

3. Bilayer Stabilizing Component

In addition to cationic and non-cationic lipids, the stabilized nucleic acid-lipid particles of the present invention can comprise a bilayer stabilizing component (BSC) such as an ATTA-lipid or a PEG-lipid such as PEG coupled to dialkyloxypropyls (PEG-DAA) as described in, e.g., PCT Publication No. WO 05/026372, PEG coupled to diacylglycerol (PEG-DAG) as described in, e.g., U.S. Patent Publication Nos. 20030077829 and 2005008689, PEG coupled to phospholipids such as phosphatidylethanolamine (PEG-PE), PEG conjugated to ceramides, or a mixture thereof (see, e.g., U.S. Pat. No. 5,885,613). In a preferred embodiment, the BSC is a conjugated lipid that prevents the aggregation of particles. Suitable conjugated lipids include, but are not limited to, PEG-lipid conjugates, ATTA-lipid conjugates, cationic-polymer-lipid conjugates (CPLs), and mixtures thereof. In another preferred embodiment, the particles comprise either a PEG-lipid conjugate or an ATTA-lipid conjugate together with a CPL.

PEG is a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH) is particularly useful for preparing the PEG-lipid conjugates including, e.g., PEG-DAA conjugates.

In a preferred embodiment, the PEG has an average molecular weight of from about 550 daltons to about 10,000 daltons, more preferably from about 750 daltons to about 5,000 daltons, more preferably from about 1,000 daltons to about 5,000 daltons, more preferably from about 1,500 daltons to about 3,000 daltons, and even more preferably about 2,000 daltons or about 750 daltons. The PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In a preferred embodiment, the linker moiety is a non-ester containing linker moiety. As used herein, the term "non-ester containing linker moiety" refers to a linker moiety that does not contain a carboxylic ester bond (—OC(O)—). Suitable non-ester containing linker moieties include, but are not limited to, amido (—C(O)NH—), amino (—NR—), carbonyl (—C(O)—), carbamate (—NHC(O)O—), urea (—NHC(O)NH—), disulphide (—S—S—), ether (—O—), succinyl (—(O)CCH$_2$CH$_2$C(O)—), succinamidyl (—NHC(O)CH$_2$CH$_2$C(O)NH—), ether, disulphide, as well as combinations thereof (such as a linker containing both a carbamate linker moiety and an amido linker moiety). In a preferred embodiment, a carbamate linker is used to couple the PEG to the lipid.

In other embodiments, an ester containing linker moiety is used to couple the PEG to the lipid. Suitable ester containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the bilayer stabilizing component. Such phosphatidylethanolamines are commercially available, or can be isolated or synthesized using conventional techniques known to those of skilled in the art. Phosphatidylethanolamines containing saturated or unsaturated fatty acids with carbon chain lengths in the range of $C_{10}$ to $C_{20}$ are preferred. Phosphatidylethanolamines with mono- or diunsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoylphosphatidylethanolamine (DOPE), and distearoyl-phosphatidylethanolamine (DSPE).

B. Additional Carrier Systems

Non-limiting examples of additional lipid-based carrier systems suitable for use in the present invention include lipoplexes (see, e.g., U.S. Patent Publication No. 20030203865; and Zhang et al., J. Control Release, 100:165-180 (2004)), pH-sensitive lipoplexes (see, e.g., U.S. Patent Publication No. 20020192275), reversibly masked lipoplexes (see, e.g., U.S. Patent Publication Nos. 20030180950), cationic lipid-based compositions (see, e.g., U.S. Pat. No. 6,756,054; and U.S. Patent Publication No. 20050234232), cationic liposomes (see, e.g., U.S. Patent Publication Nos. 20030229040, 20020160038, and 20020012998; U.S. Pat. No. 5,908,635; and PCT Publication No. WO 01/72283), anionic liposomes (see, e.g., U.S. Patent Publication No. 20030026831), pH-sensitive liposomes (see, e.g., U.S. Patent Publication No. 20020192274; and AU 2003210303), antibody-coated liposomes (see, e.g., U.S. Patent Publication No. 20030108597; and PCT Publication No. WO 00/50008), cell-type specific liposomes (see, e.g., U.S. Patent Publication No. 20030198664), liposomes containing nucleic acid and peptides (see, e.g., U.S. Pat. No. 6,207,456), liposomes containing lipids derivatized with releasable hydrophilic polymers (see, e.g., U.S. Patent Publication No. 20030031704), lipid-entrapped nucleic acid (see, e.g., PCT Publication Nos. WO 03/057190 and WO 03/059322), lipid-encapsulated nucleic acid (see, e.g., U.S. Patent Publication No. 20030129221; and U.S. Pat. No. 5,756,122), other liposomal compositions (see, e.g., U.S. Patent Publication Nos. 20030035829 and 20030072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 20050037086).

Examples of polymer-based carrier systems suitable for use in the present invention include, but are not limited to, cationic polymer-nucleic acid complexes (i.e., polyplexes). To form a polyplex, a nucleic acid (e.g., siRNA) is typically complexed with a cationic polymer having a linear, branched, star, or dendritic polymeric structure that condenses the nucleic acid into positively charged particles capable of interacting with anionic proteoglycans at the cell surface and entering cells by endocytosis. In some embodiments, the polyplex comprises nucleic acid (e.g., siRNA) complexed with a cationic polymer such as polyethylenimine (PEI) (see, e.g., U.S. Pat. No. 6,013,240; commercially available from Qbiogene, Inc. (Carlsbad, Calif.) as In vivo jetPEI™, a linear form of PEI), polypropylenimine (PPI), polyvinylpyrrolidone (PVP), poly-L-lysine (PLL), diethylaminoethyl (DEAE)-dextran, poly(.beta.-amino ester) (PAE) polymers (see, e.g., Lynn et al., J. Am. Chem. Soc., 123:8155-8156 (2001)), chitosan, polyamidoamine (PAMAM) dendrimers (see, e.g., Kukowska-Latallo et al., Proc. Natl. Acad. Sci. USA, 93:4897-4902 (1996)), porphyrin (see, e.g., U.S. Pat. No. 6,620,805), polyvinylether (see, e.g., U.S. Patent Publication No. 20040156909), polycyclic amidinium (see, e.g., U.S. Patent Publication No. 20030220289), other polymers comprising primary amine, imine, guanidine, and/or imidazole groups (see, e.g., U.S. Pat. No. 6,013,240; PCT Publication No. WO/9602655; PCT Publication No. WO95/21931; Zhang et al., J. Control Release, 100:165-180 (2004); and Tiera et al., Curr. Gene Ther., 6:59-71 (2006)), and a mixture thereof. In other embodiments, the polyplex comprises cationic polymer-nucleic acid complexes as described in U.S. Patent Publication Nos. 20060211643, 20050222064, 20030125281, and 20030185890, and PCT Publication No. WO 03/066069; biodegradable poly(β-amino ester) polymer-nucleic acid complexes as described in U.S. Patent Publication No. 20040071654; microparticles containing polymeric matrices as described in U.S. Patent Publication No. 20040142475; other microparticle compositions as described in U.S. Patent Publication No. 20030157030; condensed nucleic acid complexes as described in U.S. Patent Publication No. 20050123600; and nanocapsule and microcapsule compositions as described in AU 2002358514 and PCT Publication No. WO 02/096551.

In certain instances, the siRNA molecule may be complexed with cyclodextrin or a polymer thereof. Non-limiting examples of cyclodextrin-based carrier systems include the cyclodextrin-modified polymer-nucleic acid complexes described in U.S. Patent Publication No. 20040087024; the linear cyclodextrin copolymer-nucleic acid complexes described in U.S. Pat. Nos. 6,509,323, 6,884,789, and 7,091,192; and the cyclodextrin polymer-complexing agent-nucleic acid complexes described in U.S. Pat. No. 7,018,609. In certain other instances, the siRNA molecule may be complexed with a peptide or polypeptide. An example of a protein-based carrier system includes, but is not limited to, the cationic oligopeptide-nucleic acid complex described in PCT Publication No. WO95/21931.

VIII. Bladder Disorders

Although the present invention may be useful for any medical condition for which a modulator of an APF receptor provides improvement of at least one symptom to any individual in need thereof, in specific embodiments the present invention is useful for one or more bladder disorders. Although the terms "bladder disorder" or "bladder condition" refer to any abnormal condition of the urinary bladder, in specific embodiments the bladder disorder comprises interstitial cystitis, bladder cancer, either as a primary or secondary cancer, chronic pelvic pain syndrome, irritable bladder syndrome, urethral syndrome, painful bladder syndrome, bladder pain syndrome, chronic nonbacterial prostatitis, and other bladder conditions characterized by increased urinary frequency often accompanied by bladder pain and/or increased urinary urgency, for example, and in some cases for which no other etiology has been determined.

In specific embodiments of the present invention, there are methods and compositions related to interstitial cystitis. Typical symptoms of interstitial cystitis include pain, which can be in the abdominal, urethral or vaginal area and is also frequently associated with sexual intercourse; urgency, which includes the sensation of having to urinate immediately and may also be accompanied by pressure and/or spasms; and increased frequency of urination, which can be day and/or night frequency of urination.

Diagnosis of intersitial cystitis is heretofore performed using cystoscopy, and hydro-distention and biopsies are normally performed at the same time. Examination by cytoscopy of a typical bladder having interstitial cystitis may identify submucosal pinpoint hemorrhages (glomerulations), thinning of the epithelium and/or Hunner's ulcers; in some cases, inflammation may also be present. Thus, there is considerable pain when urine enters into the bladder of an IC patient, making it very difficult for patients with interstitial cystitis to be able to hold urine in their bladder, due to the burning, stinging and pain.

Current therapies include oral medications, such as Elmiron®, Amitriptyline (Elavil®) Atarax®, Neurontin®, Ditropan®, Prozac®, and Cimetidine, for example. In specific embodiments of the invention, therapeutic agents associated with the present invention are used either alone or in conjunction with one or more of these or similar medications. In specific embodiments, the patients also suffer with various other syndromes including fibromyalgia, urethral syndrome, vulvodynia, irritable bowel syndrome, chronic fatigue syndrome, allergies, and other auto-immune disorders, such as scleroderma, systemic lupus erythematous, for example, that may be associated with interstitial cystitis.

IX. Pharmaceutical Compositions

The present invention is also directed to pharmaceutical compositions for use in treating or ameliorating or preventing bladder conditions, such as interstitial cystitis. It is further contemplated that the compounds of the present invention may be used to block the interaction of APF with its target for the treatment of interstitial cystitis or other disorders related to cell proliferation. In particular, the APF receptor is modulated such that APF is prevented from binding at least one of its natural targets, such as the APF receptor itself, including an APF receptor that resides in one or more membranes.

Such methods generally involve administering a pharmaceutical composition comprising an effective amount of a substance that inhibits palmitoylation of the APF receptor. Where the invention is directed to treating with the compounds of the present invention, administration of the compounds of the invention with a suitable pharmaceutical excipient as necessary can be carried out via any of the accepted modes of administration. The compounds may be comprised in a pharmaceutically acceptable excipient, which may be considered as a molecular entity and/or composition that does not produce an adverse, allergic and/or other untoward reaction when administered to an animal, as appropriate. It includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated.

Thus, administration can be, for example, intravenous, topical, subcutaneous, transcutaneous, intramuscular, oral, intra-joint, parenteral, peritoneal, intranasal, intravesical or by inhalation. Suitable sites of administration thus include, but are not limited to, skin, bronchial, gastrointestinal, anal, vaginal, eye, bladder, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art, e.g., REMINGTON'S PHARMACEUTICAL SCIENCES, 18TH ED., Mack Publishing Co., Easton, Pa. (1990).

The compositions of the present invention may be administered to the bladder directly, such as by catheter, or it may be released as by an osmotic pump. It may also be made directly by bladder cells that have been transfected with nucleic acid or a viral agent, for example, carrying nucleic acid that encodes the receptor in a soluble form that is then secreted by the cell.

For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see Remington's Pharmaceutical Sciences, supra., and similar publications. The composition to be administered will, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person. However, it is possible that an effective dose of APF, especially if administered directly into the bladder, may be outside of this range.

X. Combination Treatments

In particular aspects of the invention, an agent that modulates a modulator of the APF receptor is employed in combination with one or more other therapies for a bladder disorder, including, for example, interstitial cystitis, and so forth. In specific aspects, the agent inhibits a post-translational modifier of the APF receptor. In additional specific aspects, the agent modulates a PAT for the APF receptor, such as inhibits a PAT for the APF receptor, and may be referred to as a PAT inhibitor for illustrative embodiments only.

The PAT modulator treatment may precede, follow, or both precede and follow the other treatment(s) by intervals ranging from minutes to weeks. In embodiments where the PAT modulator composition and the other agent are applied separately to a cell of the individual, such as via the luminal side of the bladder, one would generally ensure that a significant period of time did not expire between the time of each delivery, such that the PAT modulator composition and the other treatment would still be able to exert an advantageously combined effect on at least one cell associated with the bladder disorder. In such instances, it is contemplated that one may instill both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, for example, wherein the PAT modulator treatment is "A" and the secondary agent is "B":

| A/B/A | B/A/B | B/B/A | A/A/B | A/B/B | B/A/A | A/B/B/B | B/A/B/B |
|---|---|---|---|---|---|---|---|
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration of the PAT modulator compositions of the present invention to a patient will follow general protocols for the administration of bladder condition therapeutics, taking into account the toxicity, if any, of the molecule. It is expected that the treatment cycles would be repeated as necessary. It also is contemplated that various standard therapies, as well as surgical intervention, may be applied in combination with the described hyperproliferative cell therapy.

In one aspect of the invention, one or more PAT modulator compositions is employed in combination with one or more therapies for interstitial cystitis (IC), and in particular aspects of the invention the combination with other IC therapies increases the effectiveness of the PAT modulator composition, increases the treatment that it is combined with, or both. The combination of the therapy of the invention with another IC therapy may provide additive therapeutic effects or synergistic therapeutic effects, for example. Exemplary IC treatment includes Elmiron®, Amitriptyline (Elavil®) Atarax®, Neurontin®, Ditropan®, Prozac®, Cimetidine, DMSO, and combinations thereof, for example.

XI. Screening For Modulators of PATs

The present invention further comprises methods for identifying modulators of the function of one or more PATs. These assays may comprise random screening of large libraries of candidate substances; alternatively, the assays may be used to focus on particular classes of compounds selected with an eye towards structural attributes that are believed to make them more likely to modulate the function of one or more PATs. For example, perusal of DHHCs, for example, such as by x-ray crystallography or NMR studies, may identify one or more particular domains that the PAT of the assay employs. In specific embodiments, the modulator of APF is a dominant negative mutant of PAT.

By function, it is meant that one may assay for the activity of a PAT, such as palmitoylation of APF receptor, for example.

To identify a modulator of PAT, one generally will determine the function of PAT, the function of APF receptor, and/or the function of APF in the presence and absence of the candidate substance, a modulator defined as any substance that alters function. For example, a method generally comprises:

(a) providing a candidate modulator;
(b) admixing the candidate modulator with a compound or cell, or a suitable experimental animal, including an isolated compound or cell, or a suitable experimental animal;
(c) measuring one or more characteristics of the compound, cell or animal in step (b); and
(d) comparing the characteristic measured in step (c) with the characteristic of the compound, cell or animal in the absence of said candidate modulator,
wherein a difference between the measured characteristics indicates that said candidate modulator is, indeed, a modulator of the compound, cell or animal.

Assays may be conducted in cell free systems, in isolated cells, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

A. Modulators

As used herein the term "candidate substance" refers to any molecule that may potentially inhibit APF activity via inhibition of PAT activity, and/or APF receptor activity. The candidate substance may be a sugar, a protein or fragment thereof, a small molecule, a nucleic acid molecule, or a mixture of combination thereof, for example. It may prove to be the case that the most useful pharmacological compounds will be compounds that are structurally related to a PAT, APF, or CKAP4. Using lead compounds to help develop improved compounds is know as "rational drug design" and includes not only comparisons with known inhibitors and activators, but predictions relating to the structure of target molecules.

The goal of rational drug design is to produce structural analogs of biologically active polypeptides or target compounds. By creating such analogs, it is possible to fashion drugs, which are more active or stable than the natural molecules, that have different susceptibility to alteration or that may affect the function of various other molecules. In one approach, one would generate a three-dimensional structure for a target molecule, or a fragment thereof. This could be accomplished by x-ray crystallography, computer modeling, by far-western, or by a combination thereof, for example.

It also is possible to use antibodies to ascertain the structure of a target compound activator or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the DHHC2 target molecule. Such compounds are described in greater detail elsewhere in this document. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on APF receptor. Regardless of the type of inhibitor or activator identified by the present screening methods, the effect of the inhibition or activator by such a compound results in modulation of APF receptor as compared to that observed in the absence of the added candidate substance.

B. In Vitro Assays

The present invention provides methods of screening for a candidate substance that modulates PAT. In these embodiments, the present invention is directed to a method for determining the ability of a candidate substance to interfere with binding of APF to APF receptor, generally including the steps of: administering a candidate substance to the animal; and determining the ability of the candidate substance to reduce one or more characteristics of APF receptor, such as ligand binding to the receptor.

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge-charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

C. In Cyto Assays

The present invention also contemplates the screening of compounds for their ability to modulate APF receptor in cells. Various cell lines can be utilized for such screening assays, including cells specifically engineered for this purpose. Exemplary cells include, for example, bladder cells, such as bladder epithelial cells, cancer cells, and so forth.

Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

D. In Vivo Assays

The present invention provides methods of screening for a candidate substance that modulates PAT. In these embodiments, the present invention is directed to a method for determining the ability of a candidate substance to interfere with binding of APF to APF receptor, generally including the steps of: administering a candidate substance to the animal; and determining the ability of the candidate substance to reduce one or more characteristics of APF receptor, such as ligand binding to the receptor.

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance (s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

XII. Nucleic Acid-Based Expression Systems

In some embodiments of the present invention, a nucleic acid-based expression system is employed, such as for encoding an agent that interferes with PAT activity, APF receptor palmitoylation, or APF binding to APF receptor. The nucleic acid-based expression system may encode the agent and may be employed to deliver the agent to a cell.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 by upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 by apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the □ lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB available on the world wide web) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other.

Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, $E.\ coli$ is often transformed using derivatives of pBR322, a plasmid derived from an $E.\ coli$ species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEMTM 11 may be utilized in making a recombinant phage vector which can be used to transform host cells, such as, for example, $E.\ coli$ LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with β galactosidase, ubiquitin, and the like.

Bacterial host cells, for example, $E.\ coli$, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

10. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Compositions of the present invention may be comprised in a viral vector that encode one or more agents that modulate APF receptor binding. Non-limiting examples of virus vectors that may be used to deliver a nucleic acid of the present invention are described below.

a. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

b. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the compositions of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

c. Retroviral Vectors

Retroviruses have promise as delivery vectors due to their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding an agent of interest) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

d. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

e. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

B. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985), and any combination of such methods. Through the application of techniques such as these, organelle(s), cell(s), tissue(s) or organism(s) may be stably or transiently transformed.

1. Ex Vivo Transformation

Methods for tranfecting vascular cells and tissues removed from an organism in an ex vivo setting are known to those of skill in the art. For example, cannine endothelial cells have been genetically altered by retrovial gene tranfer in vitro and transplanted into a canine (Wilson et al., 1989). In another example, yucatan minipig endothelial cells were tranfected by retrovirus in vitro and transplated into an artery using a double-ballonw catheter (Nabel et al., 1989). Thus, it is contemplated that cells or tissues may be removed and tranfected ex vivo using the nucleic acids of the present invention. In particular aspects, the transplanted cells or tissues may be placed into an organism. In preferred facets, a nucleic acid is expressed in the transplated cells or tissues.

2. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus oocytes* (Harland and Weintraub, 1985). The amount of agent used may vary upon the nature of the antigen as well as the organelle, cell, tissue or organism used 3. Electroporation In certain embodiments of the present invention, a nucleic acid is introduced into an organelle, a cell, a tissue or an organism via electroporation. Electroporation involves the exposure of a suspension of cells and DNA to a high voltage electric discharge. In some variants of this method, certain cell wall degrading enzymes, such as pectin degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre B lymphocytes have been transfected with human kappa immunoglobulin genes (Potter et al., 1984), and rat hepatocytes have been transfected with the chloramphenicol acetyltransferase gene (Tur Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

4. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV 1, BHK, NIH3T3 and HeLa cells were transfected with a neomycin marker gene (Chen and Okayama, 1987), and rat hepatocytes were transfected with a variety of marker genes (Rippe et al., 1990).

5. DEAE Dextran

In another embodiment, a nucleic acid is delivered into a cell using DEAE dextran followed by polyethylene glycol. In this manner, reporter plasmids were introduced into mouse myeloma and erythroleukemia cells (Gopal, 1985).

6. Sonication Loading

Additional embodiments of the present invention include the introduction of a nucleic acid by direct sonic loading. LTK fibroblasts have been transfected with the thymidine kinase gene by sonication loading (Fechheimer et al., 1987).

7. Liposome Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome mediated nucleic acid delivery and expression of foreign DNA in vitro has been very successful (Nicolau and Sene, 1982; Fraley et al., 1979; Nicolau et al., 1987). The feasibility of liposome mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome encapsulated DNA (Kaneda et al., 1989). In other embodiments, a liposome may be complexed or employed in conjunction with nuclear non histone chromosomal proteins (HMG 1) (Kato et al., 1991). In yet further embodiments, a liposome may be complexed or employed in conjunction with both HVJ and HMG 1. In other embodiments, a delivery vehicle may comprise a ligand and a liposome.

C. Receptor Mediated Transfection

Still further, a nucleic acid may be delivered to a target cell via receptor mediated delivery vehicles. These take advantage of the selective uptake of macromolecules by receptor mediated endocytosis that will be occurring in a target cell. In view of the cell type specific distribution of various receptors, this delivery method adds another degree of specificity to the present invention.

Certain receptor mediated gene targeting vehicles comprise a cell receptor specific ligand and a nucleic acid binding agent. Others comprise a cell receptor specific ligand to which the nucleic acid to be delivered has been operatively attached. Several ligands have been used for receptor mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell specific binding. For example, lactosyl ceramide, a galactose terminal asialganglioside, have been incorporated into liposomes and observed an increase in the uptake of the insulin gene by hepatocytes (Nicolau et al., 1987). It is contemplated that the tissue specific transforming constructs of the present invention can be specifically delivered into a target cell in a similar manner.

D. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

E. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co expressed with other selected RNAs or proteinaceous sequences in the same host cell. Co expression may be achieved by co transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with an agent of the invention. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, anthers, ascite tissue, cobs, ears, flowers, husks, kernels, leaves, meristematic cells, pollen, root tips, roots, silk, stalks, and all cancers thereof.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art (see, for example, webpage http://phylogeny.arizona.edu/tree/phylogeny.html).

Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F, lambda, prototrophic, ATCC No. 273325), DH5α, JM109, and KC8, bacilli such as *Bacillus subtilis*; and other enterobacteriaceae such as *Salmonella typhimurium, Serratia marcescens*, various *Pseudomonas* specie, as well as a number of commercially available bacterial hosts such as SURE® Competent Cells and SOLOPACK™ Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

F. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed", i.e., expressed in increased levels relative to its natural expression in cells. Such overexpression may be assessed by a variety of methods, including radio labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g. 8M) or chaotropic agents such as guanidine hydrochloride in the presence of reducing agents, such as ⊔ mercaptoethanol or DTT (dithiothreitol), and refolded into a more desirable conformation, as would be known to one of ordinary skill in the art.

XIII. Kits of the Invention

Therapeutic kits comprise another aspect of the present invention. Such kits will generally contain, in suitable container means, one or more agents that modulate an molecule that modulates APF receptor. In specific embodiments, one or more PAT inhibitors of the present invention are provided in the kit. The kit may have a single container means that contains the PAT inhibitor composition or it may have distinct container means for the PAT inhibitor composition and other reagents that may be included within such kits. Some kits may comprise other inhibitors of APF in suitable container means, such as antibodies, small interference RNAs, and so forth. The PAT inhibitors may be nucleic acid, amino acid, small molecule, or mixtures thereof. In particular cases, the PAT inhibitor is a siRNA. The kit may further comprise an inhibitor of APF and/or an additional therapy for a bladder condition.

The components of the kit may be provided as liquid solution(s), or as dried powder(s). When the components are provided in a liquid solution, the liquid solution is an aqueous or non-aqueous solution, with a sterile aqueous or non-aqueous solution being particularly preferred. When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the composition may be placed, and preferably suitably aliquoted. Where a second composition is provided, the kit will also generally contain a second vial or other container into which this ligand or antibody may be placed. The kits of the present invention will also typically include a means for containing the composition containers in close confinement for commercial sale. Such containers may include injection or blow-molded plastic containers into which the desired vials are retained.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Materials and Methods

The following materials and methods were employed in the invention, although one of skill in the art recognizes that suitable alternative methods and materials may also be employed.

ZDHHC2 Knockdown by SIRNA Transfection of HeLa Cells

One day prior to transfection, HeLa cells (ATCC #CCL-2) were plated in 10 ml of antibiotic-free DMEM medium supplemented with 10% fetal bovine serum (per 10 cm plate) to yield 30~50% confluency at the time of transfection. For each transfection, 50 µl of ZDHHC2 siRNA (20 pmol/µl final concentration) was diluted in 833 µl of serum-containing DMEM medium, mixed gently, and incubated for 5 min at room temperature. Fifty µl of Oligofectamine reagent (Invitrogen) were added to 200 µl of serum-free DMEM medium, mixed gently, and incubated for 5 min at room temperature. The diluted siRNA and Oligofectamine samples were then combined (total volume is 1033 µl), mixed gently, and incubated for 20 min at room temperature to allow siRNA:Oligofectamine complex formation. Complexes were subsequently diluted in 9 ml of antibiotic-free, serum-containing DMEM medium and added to the HeLa cells. The cells were incubated at 37° C. in a $CO_2$ incubator for 48-72 hrs until they reached confluency and were ready to assay for gene knockdown.

Real Time PCR Quantitation of Gene Knockdown

Total RNA was isolated from untreated and siRNA-treated HeLa cells using the RNAqueous small scale phenol-free kit (Ambion) according to the manufacturer's protocol. RNA was assessed by visualization of the 28S/18S ribosomal RNA ratio on a 1% agarose gel. Total RNA concentration was determined by measuring the absorbance of each sample at 260 nm and 280 nm using a Gene Quant RNA/DNA Calculator (Pharmacia Biotech). Only samples with $OD_{260}/OD_{280}$ ratio between 1.8 and 2.0 were used for reverse transcription-PCR. First strand cDNA synthesis was performed using 5 µg of total RNA and Superscript III (Invitrogen) according to the manufacturer's protocol. ZDHHC2 primer sequences were designed using Primer Express 2.0, and specificity was confirmed using a BLAST search. Quantitative real-time-PCR (qRT-PCR) analysis was carried out on ABI Prism® 7900 Sequence Detection system (Applied Biosystems, Foster City, Calif.) using SYBR® green dye for detection. Each sample consisted of the following: 100 ng cDNA, 300 nM primers and 12.5 µl of SYBR® green PCR Master Mix (Applied Biosystems) in a reaction volume of 25 µl. Amplification conditions included two initial steps at 95° C. (20 min) and 95° C. (10 min) followed by 40 repetitions of the following cycle 95° C. (15 sec), 60° C. (1 min) and finally, a dissociation stage at 95° C. (15 sec), 60° C. (20 sec) and 95° C. (15 sec). Samples were tested in triplicate and ZDHHC2 mRNA levels were normalized to that of 18S rRNA (Wong and Medrano, 2005). The data were analyzed using Relative Quantitation (Heid et al., 1996).

Differential Labeling and Identification of DHHC2 Substrates with ICAT Reagents

Proteins from untreated and siRNA-treated HeLa cells were extracted and treated with MMTS as above. Precipitated proteins were dissolved (proteins from normal control cells and RNAi-treated cells) in 100 µl fresh labeling buffer (0.05% SDS, 50 mM Tris (pH 7.4), 5 mM EDTA, 6 M Urea), and the protein concentration was measured to ensure that they were equal and no more than 4 mg/ml. Protein samples were allowed to react with H and L ICAT reagents in 7 µl of 50% NH2OH (pH 7.4). After labeling, the control and siRNA-treated protein samples were combined, fractionated by SDS-PAGE, and digested in-gel with trypsin. ICAT labeled peptides from different gel fractions (regions) were enriched by avidin purification and cleaved to remove biotin groups.

Co-Over Expression of DHHC2 and CKAP4/p63

To confirm that DHHC2 palmitoylates CKAP4/p63, an established method was employed (Fukata et al., 2004; Fukata et al., 2006) in which COS cells were transfected with plasmids containing cDNAs encoding DHHC2 and/or CKAP4/p63 using Fugene 6 (Roche). Twenty-four hours after the transfection, the cells were serum starved for 30 minutes then metabolically labeled with 0.5 mCi of $^3[H]$ palmitic acid for 6 hours. Cells were washed in PBS then harvested in SDS sample buffer containing 62.5 mM tris-HCl, pH 6.8, 2% SDS, 10% glycerol, 10 mM DTT and bromophenol blue. Equal quantities of proteins from each condition were separated by SDS-PAGE. The gels were fixed 30 min in isopropanol:water:acetic acid=25:65:10. Autofluorographic images were generated by treating the gels with Amplify (GE Healthcare) for 30 minutes. The gels were dried and exposed to film at −80° C. for 24-48 hours.

Immunofluorescent Labeling of CKAP4/p63 in Hela Cells: Control Versus ZDHHC2 Knockdown Double stranded siRNA targeting ZDHHC2 was purchased from Dharmacon. HeLa cells or cells explanted from IC patients (IC cells) were trypsinized for 10 minutes at room temperature, centrifuged in growth medium (MEM with 10% heat inactivated FBS, 1% antibiotic/antimycotics solution, and 1% L glutamine), and the cell pellet was resuspended in serum-free medium at a density of $1 \times 10^4$ cells/ml. One mL of the cell suspension was then transferred to a sterile 2 mm cuvette with 20 µM siRNA, and electroporated at 160 V/500 µF capacitance using a BioRad Gene Pulser Xcell. HeLa cells were then plated onto a 96 well plate for the thymidine incorporation assay, and both HeLa and IC cells were plated onto an 8 well Lab-Tek tissue culture slide for confocal microscopy.

For confocal microscopy, after 96 hours of incubation the medium was removed from the wells and cells were fixed using ethanol/acetone (1:1) for 15 min at room temperature, washed three times with 1×PBS, and incubated with mouse monoclonal anti-CKAP4/p63 antibodies ("anti-CLIMP-63", clone G1/296; Alexis Biochemicals) in PBS, for 2 hrs at 37° C. Cells were then washed three times with PBS and further incubated with fluorescein isothiocyanate (FITC)-labeled secondary antibody diluted in PBS (goat anti-Mouse IgG 1:2000; Zymed) for 2 hrs at 37° C. Following five additional washes with PBS, cells were examined using a Zeiss LSM510 confocal laser-scanning microscope. Negative controls for the method included cells incubated without primary and/or secondary antibodies, as well as cells incubated with secondary antibody alone.

$^3$H-Thymidine Incorporation

Cell proliferation was measured by 3H-thymidine incorporation into ZDHHC2 siRNA-treated HeLa cells. Briefly, electroporated cells that received ZDHHC2 or control nonsense siRNA were plated into 96 well culture plates and incubated at 37° C. in a 5% $CO_2$ atmosphere for 96 hours. Purified lyophilized synthetic APF was re-suspended in acetonitrile/distilled water (1:1), diluted in serum-free MEM (containing only glutamine and antibiotics/antimycotics), and applied to HeLa cells; cell controls received acetonitrile/distilled water diluted in serum-free MEM alone. Cells were then incubated for an additional 48 hours. The cell contents were harvested and methanol-fixed onto glass fiber filter paper, and the amount of radioactivity incorporated determined. Significant inhibition of $^3$H-thymidine incorporation was defined as a mean decrease in counts per minute of greater than 2 standard deviations from the mean of control cells for each plate.

Example 2

Identification of DHHC2 Substrates

Figure 2:
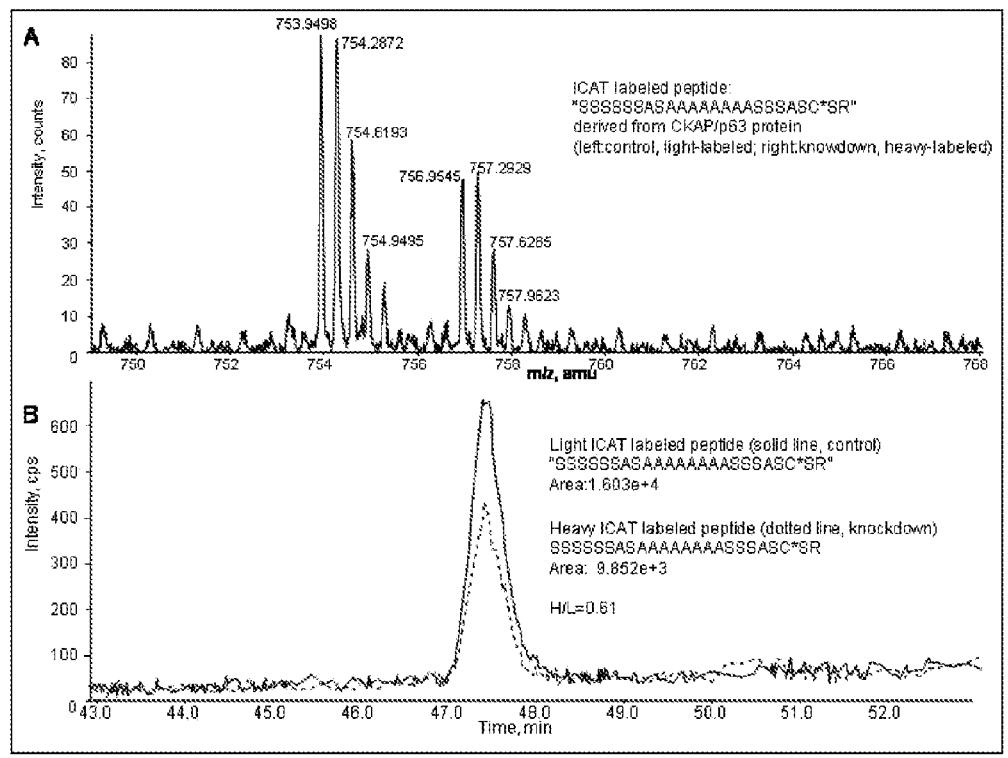
FIGS. 2A-2B provide mass spectrometry identification of CKAP4/p63 peptides labeled by H and L ICAT reagents. (A) ICAT-labeled tryptic peptides (m/z 753.9 and 756.9) derived from a putative palmitoylated protein and detected by LC-MS/MS in the retention time range 35-40 min. Following a Mascot protein database search of the corresponding MS/MS spectrum, the sequence was determined to be SSSSSSASAAAAAAAASSSASC*SR (SEQ ID NO:3), a tryptic peptide of CKAP/p63 modified at the cysteine residue with the ICAT reagent. The specificity of the labeling reaction allows for selective derivatization of protein palmitoylation sites with the ICAT reagent. The 9 Da mass difference (Δm/z 3 for a triply-charged species) provided by the heavy ICAT reagent can be observed for this particular ICAT pair, and any variation in mass spectral intensity correlates to changes in protein palmitolylation induced from the ZDHHC2 knockdown treatment. (B) Reconstructed ion chromatogram derived from the monoisotopic masses corresponding to the L and H ICAT-labeled peptide SSSSSSASAAAAAAAASSSASC*SR (SEQ ID NO:3) from a separate experiment. Upon calculation of the peak-area ratios (H:L) obtained from four separate experiments using a quantitation algorithm within the data acquisition software, this particular protein showed a 35% decrease in palmitoylation ($p<0.001$, $n=4$) after ZDHHC2 knockdown.
Figure 3:
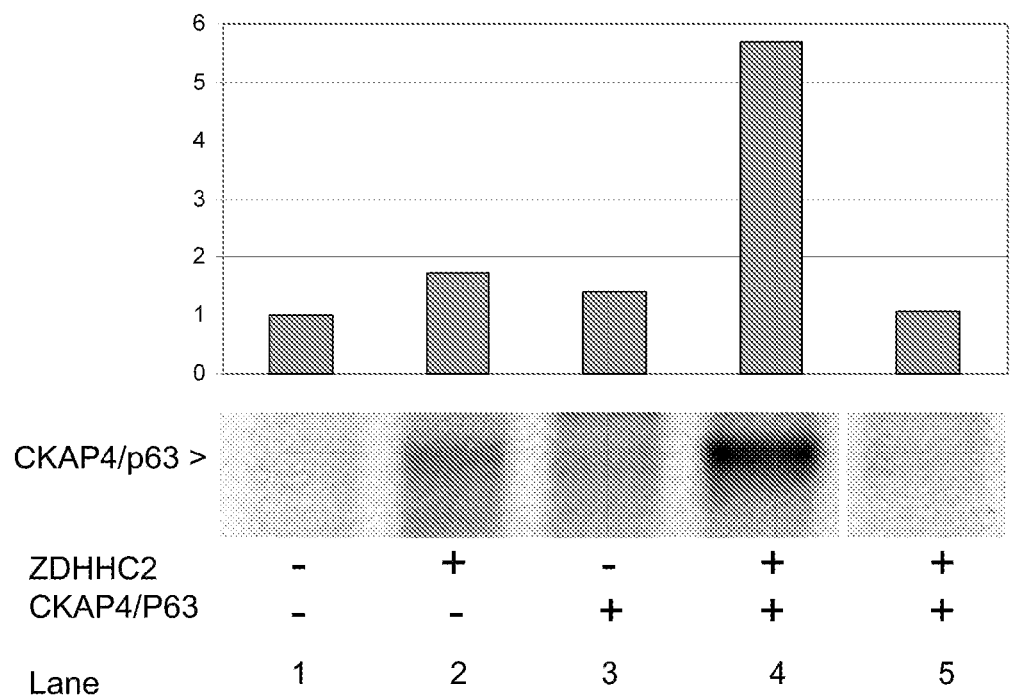
FIG. 3 shows confirmation that CKAP4/p63 is a substrate of DHHC2. Co-overexpression of CKAP4/p63 and DHHC2 in COS cells results in a dramatic increase in the incorporation of $^3[H]$ palmitate into CKAP4/p63. In normal control cells, or cells in which either DHHC2 or CKAP4/p63 are overexpressed, CKAP4/p63 does not incorporate measurable amounts of $^3[H]$ palmitate (Lanes 1-3). When both DHHC2 and CKAP4/p63 are overexpressed together, CKAP4/p63 is labeled at significantly higher levels confirming that it is a substrate of DHHC2 (lane 4 and *). Treatment of the same protein sample run in lane 4 with hydroxylamine removes palmitate from CKAP4/p63 confirming that $^3[H]$ palmitate is attached by a thioester bond (lane 5).

To identify substrates of DHHC2 in HeLa cells, the level of endogenous ZDHHC2 mRNA expression was reduced using siRNA (Dharmacon) and measured the resulting global changes in palmitoylation with PICA and the thiol-reactive ICAT reagents (Gygi et al., 1999)—the H tag on proteins from the ZDHHC2 knockdown and the L on those from the control. After 48-60 hrs of siRNA exposure, ZDHHC2 mRNA expression was reduced 93% as measured by qRT-PCR. Using PICA, ~50 ICAT-labeled proteins were identified, including some already known to be palmitoylated. For most of the proteins identified, the H:L ratio does not deviate significantly from parity, indicating that they are not substrates of DHHC2. However, CKAP4/p63, a type II transmembrane domain protein known to be palmitoylated (Schweizer et al., 1995), was captured (FIG. 2), and palmitoylation was reduced an average of 35% in the ZDHHC2 knockdown cells versus control (mean H:L ratio=0.65; p=0.001; n=4), indicating that it is a substrate of DHHC2. CKAP4/p63 was palmitoylated on Cys100 in the tryptic peptide 78—SSSSSSASAAAAAAAASSSASC*SR-102 (SEQ ID NO:3) corresponding to the cysteine previously reported to be palmitoylated (Schweizer et al., 1995). To confirm that DHHC2 palmitoylates CKAP4/p63, ZDHHC2 and/or CKAP4/p63 were overexpressed in COS cells and metabolically labeled the cells with $^3$[H] palmitate. When both DHHC2 and CKAP4/P63 were over expressed together in the same cells, there was a marked increase in the incorporation of $^3$[H] palmitate into CKAP4/p63 (FIG. 3).

Expression of either construct alone did not result in a signal from CKAP4/p63 that was greater than background (metabolically-labeled, untransfected COS cells). It was confirmed that the radiolabeled band was CKAP4/p63 by Western blot using the same antibody as was done for immunocytochemical localization of CKAP4/p63 in HeLa cells.

Example 3

Figure 4:
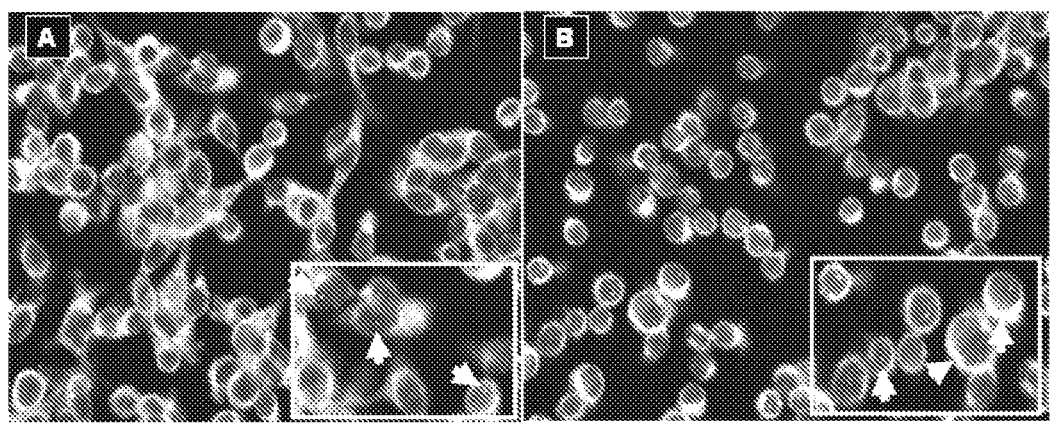
FIGS. 4A-4B show that CKAP4/p63 is confined to perinuclear membranes when DHHC2-mediated palmitoylation is blocked by siRNA-mediated ZDHHC2 knockdown. A. CKAP4/p63 immunolocalization in untreated, normal HeLa cells shows a distribution throughout the cytoplasm and in the nucleolus (inset: arrows). B. In HeLa cells treated for 48 hours with siRNA targeting ZDHHC2, the immunostaining is no longer dispersed throughout the cytoplasm but is confined to the perinuclear membranes (inset: arrows). The nucleolar immunolocalization persists in cells in which ZDHHC2 is knocked down. No other gross morphological changes were detected in the treated cells at the 48 hour time point.

Immunolocalization of CKAP4/p63 Following siRNA-Mediated Silencing of ZDHHC2 Expression Knockdown of ZDHHC2 in HeLa cells for 48 hours followed by immunolocalization of CKAP4/p63 results in a gross redistribution of CKAP4/p63. In control cells, labeling is distributed broadly throughout the cytoplasm of the cells (FIG. 4A) which is in agreement with published observations (Schweizer et al., 1994; Klopfenstein et al., 2001; Vedrenne et al., 2005)). In cells in which ZDHHC2 was silenced the distribution was limited to membranes close to the nucleus (FIG. 4B). There were no other obvious changes in cellular morphology.

Figure 5:
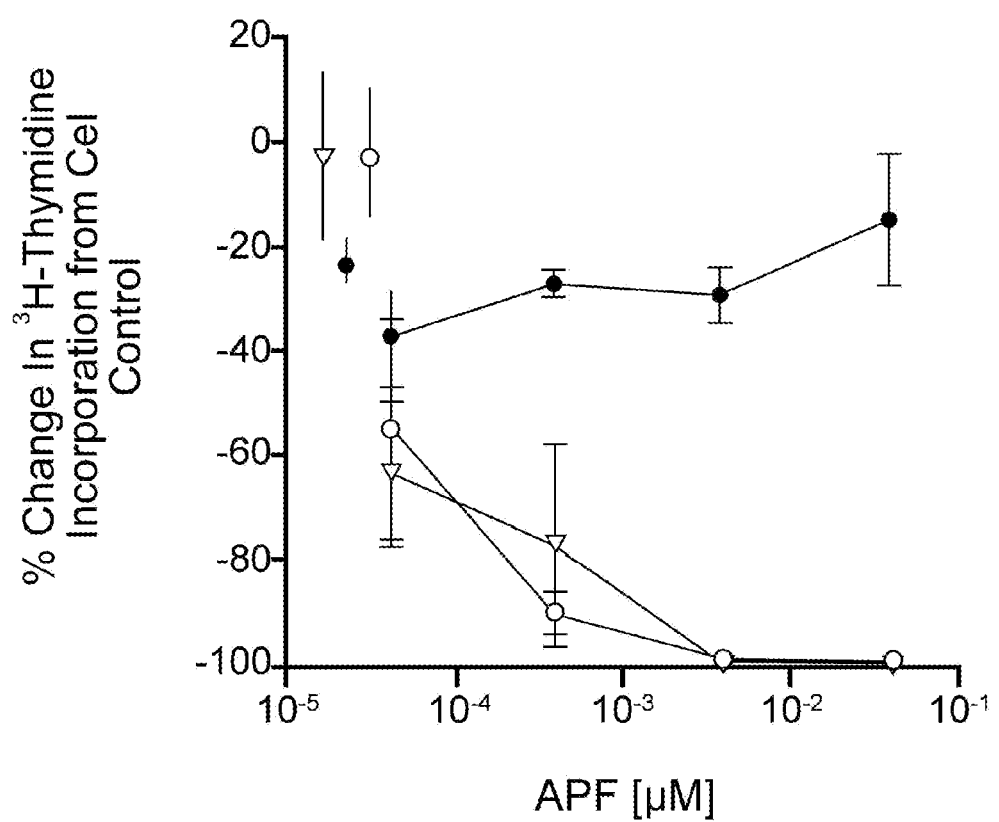
FIG. 5 shows the effect of siRNA knockdown of ZDHHC2 activity on APF sensitivity of HeLa cells (closed circles are ZDHHC2 siRNA-treated cells; open circles and open triangles are untreated control cells and cells treated with a nonsense siRNA).

FIG. 5 shows the effect of siRNA knockdown of ZDHHC2 activity on APF sensitivity of HeLa cells (closed circles are ZDHHC2 siRNA-treated cells; open circles and open triangles are untreated control cells and cells treated with a nonsense siRNA).

Figure 6:
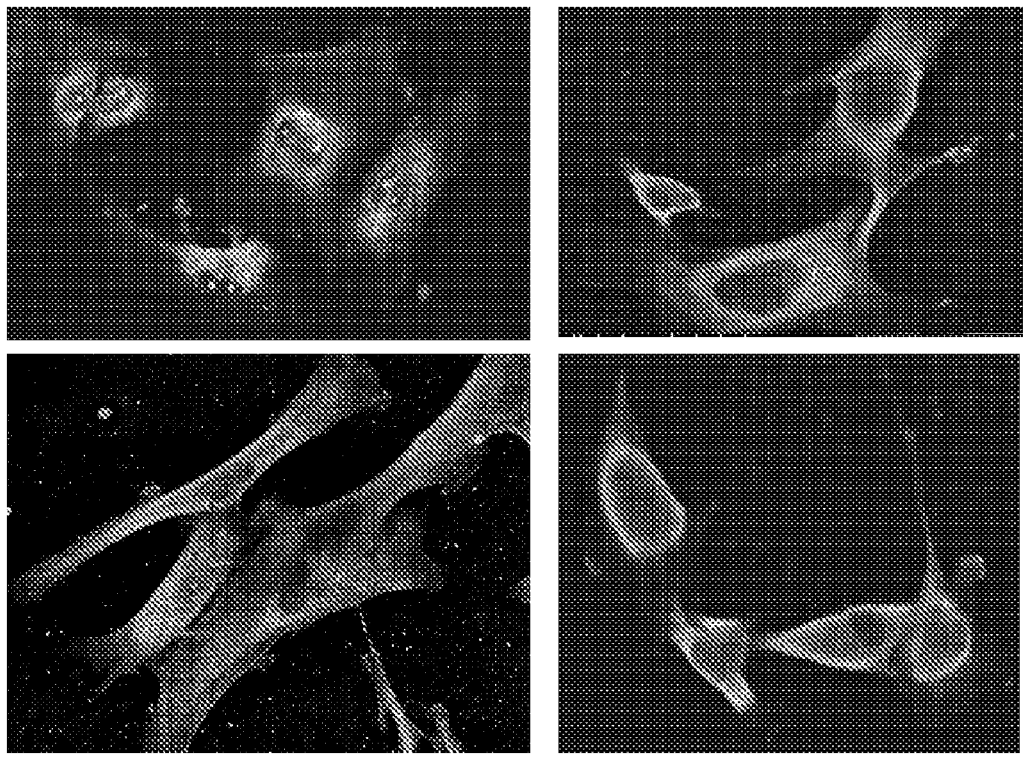
FIG. 6 provides representative confocal images of IC cells that were given ZDHHC2 siRNA knockdown. The two left panels are controls (top—nonsense siRNA-treated control; bottom—electroporation control) and the two right panels received ZDHHC2 siRNA. These images were taken 96 hours after siRNA knockdown was performed.

FIG. 6 provides representative confocal images of IC cells that were given ZDHHC2 siRNA knockdown. The two left panels are controls (top—nonsense siRNA-treated control; bottom—electroporation control) and the two right panels received ZDHHC2 siRNA. These images were taken 96 hours after siRNA knockdown was performed.

Example 4

Particular Inventive Embodiments

CKAP4 was identified as a major substrate of the palmitoyl acyl transferase DHHC2 using a novel proteomic method called Palmitoyl-cysteine Identification, Capture and Analysis (PICA). CKAP4 is a reversibly palmitoylated and phosphorylated protein that links the ER to the cytoskeleton. It is also a high-affinity receptor for APF, a small glycosylated peptide secreted from bladder epithelial cells of patients with interstitial cystitis. The ability of DHHC2-mediated palmitoylation of CKAP4 to regulate the antiproliferative effects of APF in HeLa cells was investigated. The data show that siRNA-mediated knockdown of DHHC2 expression and consequent suppression of CKAP4 palmitoylation blocks the ability of APF to regulate proliferation. Immunocytochemistry revealed inhibition of CKAP4 trafficking to the plasma membrane following DHHC2 knockdown. Stable expression of a palmitoylation-incompetent form of CKAP4 showed reduced binding to microtubules and significantly increased the rate of cell migration. These data indicate an important role for DHHC2-mediated palmitoylation of CKAP4 in cancer-related cellular behaviors and indicates that DHHC2 is a tumor suppressor, in specific embodiments of the invention.

Example 5

Palmitoylation of Cytoskeletal Associated Protein 4 by DHHC2 Regulates Antiproliferative Factor-Mediated Signaling The ability of DHHC2-mediated palmitoylation of CKAP4 to regulate the antiproliferative effects of APF in HeLa and normal bladder epithelial cells was characterized in this Example. The exemplary data described below show that siRNA-mediated knockdown of DHHC2 and consequent suppression of CKAP4 palmitoylation blocks the ability of APF to regulate cellular proliferation; moreover, APF-induced changes in the expression of E-cadherin, vimentin, and ZO-1—genes known to play a role in cellular proliferation and tumorigenesis—are inhibited. Immunocytochemistry revealed inhibition of APF-stimulated CKAP4 nuclear localization following DHHC2 knockdown. Stable expression of a palmitoylation-incompetent form of CKAP4 significantly increased the rate of cell migration. These data indicate an important role for DHHC2-mediated palmitoylation of CKAP4 in opposing cancer-related cellular behaviors (such as proliferation and migration) and shows that DHHC2 is a tumor suppressor, in certain embodiments of the invention.

Exemplary Methods and Materials

DNA Constructs—A vector construct containing wild-type CKAP4 (WT CKAP4) fused in-frame to the N-terminus of the V5 and 6×His epitope tags was generated by PCR using CKAP4 specific primers and cDNA from HeLa cells. A palmitoylation-incompetent form of CKAP4 (CKAP4 C100S) was created using site-directed mutagenesis (Stratagene) to alter the cysteine at position 100 to serine.

Cell Culture and Transfections—HeLa (ATCC #CCL-2) cells were maintained in Dulbecco's modified Eagle's medium (DMEM) containing 10% fetal bovine serum (FBS), 100 U/ml penicillin, 100 µg/ml streptomycin, and 1 µg/ml fungizone (all from Invitrogen). Cells were transfected using FuGENE6 reagent (Roche) according to the manufacturer's instructions. To obtain stable clones, cells were diluted into 96-well plates (100 cells/well) 24 hours post-transfection and selected in the presence of 0.4 mg/ml Geneticin (G418) (Invitrogen).

Normal primary bladder (NB) epithelial cells were isolated from patients as previously described (Conrads et al., 2006; Keay et al., 2000; Keay et al., 2004; Keay et al., 1996). Cells were propagated in DMEM-F12 (Media-Tech) with 10% heat inactivated FBS, 1% antibiotic/antimycotic solution, 1% L-glutamine, 0.25 U/ml insulin (Sigma), and 5 ng/ml human epidermal growth factor (R & D Systems) at 37° C. in a 5% $CO_2$ atmosphere, and characterized by binding of AE-1/AE-3 pancytokeratin antibodies (Signet) as previously described (Keay et al., 1996; Keay et al., 2004).

siRNA—Double-stranded siRNA targeting ZDHHC2 (available from GenBank/EMBL/DDBJ under accession no. NM_016353) was purchased from Dharmacon (ON-TARGET plus). The target sequences for DHHC2 were (all 5' to 3'): GACAGAUGCCAACUUAUAA (SEQ ID NO:54), CCAAGGAUCUUCCCAUCUA (SEQ ID NO:55), ACAAAUGGCCUACCUGAUA (SEQ ID NO:56), GGCAACAGAUUUACAGUAU (SEQ ID NO:57). A blast homology search confirmed that these sequences had no homology to any other human ZDHHC gene. Nonsense siRNA (ON-TARGETplus™ Control siRNA) was purchased from Dharmacon and served as a control for nonsequence-specific effects. HeLa cells were trypsinized for 5 minutes at 37° C., centrifuged in DMEM growth medium, and the cell pellet was resuspended in serum-free medium at a density of $1 \times 10^6$ cells/ml. 200 µl of the cell suspension was then transferred to a sterile 2 mm cuvette with 14 µg siRNA and electroporated at 160 V/500 µF capacitance using a BioRad Gene Pulser Xcell. The cells were immediately transferred to 96-well plates for thymidine incorporation assay or to LabTek multiwell glass slides (Nalge Nunc) for immunocytochemistry.

$^3$H-Thymidine Incorporation—Cell proliferation was measured by 3H-thymidine incorporation into the DNA of HeLa or NB epithelial cells. Briefly, synthetic APF or inactive control peptide (NeoMPS) was resuspended in acetonitrile/distilled water (1:1), diluted in serum-free DMEM, and applied to HeLa or NB cells; cell controls received acetonitrile/distilled water diluted in serum-free DMEM alone. Cells were then incubated at 37° C. in a 5% $CO_2$ atmosphere for 48 hours. The cell contents were harvested and methanol-fixed onto glass fiber filter paper, and the amount of radioactivity incorporated determined. Significant inhibition of $^3$H-thymidine incorporation was defined as a mean decrease in counts per minute of greater than 2 standard deviations from the mean of control cells for each plate.

Immunocytochemistry—HeLa cells stably transfected with WT CKAP4 or CKAP4 C100S were seeded at a density of $2 \times 10^4$ cells/well in 8-well LabTek chamber slides (Nalge Nunc) and grown to semi-confluence in DMEM medium containing 10% FBS, 100 U/ml penicillin, 100 µg/ml streptomycin, 1 µg/ml fungizone, and 0.4 mg/ml G418 (all from Invitrogen). Cells were fixed for 20 minutes with 3% paraformaldehyde in PBS, permeabilized with 0.1% Triton X-100 in PBS, and blocked in PBS/5% NGS (normal goat serum). Cells transfected with DHHC2 siRNA and treated with synthetic APF (Peptides International) were fixed using ethanol/acetone (1:1) for 15 minutes at room temperature and washed three times with 1×PBS prior to blocking in PBS/5% NGS. The following primary antibodies were used: mouse mAb G1/296 against CKAP4 ("anti-CLIMP-63", Alexis Biochemicals) and fluorescein isothiocyanate (FITC)-conjugated mouse mAb against the V5 epitope (Invitrogen). Secondary antibodies were FITC-labeled goat anti mouse (Invitrogen) and tetramethyl rhodamine isothiocyanate (TRITC)-labeled goat anti-mouse (Jackson ImmunoResearch Laboratories). Slides were mounted in SlowFade Antifade reagent (Invitrogen) and imaged using a Nikon TE2000 epifluorescence microscope.

Quantitative Real-Time PCR—Total RNA was extracted from synthetic APF, inactive control peptide-treated, or control untreated NB epithelial cells using the RNeasy Plus Mini Kit (Qiagen) according to the manufacturer's protocol. RNA was assessed by visualization of the 28S/18S ribosomal RNA ratio on a 1% agarose gel, and total RNA concentration determined by measuring the absorbance of each sample at 260 nm and 280 nm using a Gene Quant RNA/DNA Calculator (Pharmacia Biotech). Quantitative real-time PCR for gene expression was performed using Quantitect Primers (Qiagen), SYBR Green RT-PCR kit reagents (Qiagen), and a Roche System II Light-Cycler (software version 3.5). Samples were tested in triplicate runs, and specific mRNA levels quantified and compared to mRNA levels for β-actin using real-time PCR analysis software from Applied Biosystems.

Western Blot Analysis—Cells were lysed in ice-cold RIPA buffer containing protease inhibitors (Pierce), sonicated, and centrifuged for 15 minutes at 4° C. The supernatant protein concentration was measured using a Folin reagent-based protein assay kit (BioRad). Proteins were separated by electrophoresis using 4-12% NuPAGE Novex Bis-Tris polyacrylamide gels in MOPS running buffer (Invitrogen) and then transferred to nitrocellulose. Membranes were blocked for 2 hours at room temperature in TBST buffer (Tris-buffered saline, pH 7.4, with 0.1% Tween 20) containing 5% nonfat milk and incubated with specific antibodies against vimentin (diluted 1:2000; BD Pharmingen) or ZO-1 (diluted 1:125; Zymed) overnight at 4° C. The membranes were subsequently washed with TBST, incubated for 1 hour at room temperature in HRP-conjugated goat anti-mouse (diluted 1:4000, Santa Cruz Biotechnology) or goat anti-rabbit (diluted 1:10000; Pierce) secondary antibodies, and developed by enhanced chemiluminescence (Pierce). To assess equal loading of protein, the membranes were stripped and reprobed for β-actin (diluted 1:5000; Sigma). The membranes were exposed to film (BioMax AR, Kodak) and the resulting images scanned at 300 dpi. The protein bands of interest were quantified using ImageJ and the integrated signal densities normalized first to β-actin (the loading control) and subsequently expressed in terms of the fractional abundance relative to untreated control cells.

Wound-healing Migration Assay—HeLa cells stably transfected with CKAP4 C100S or parental controls were seeded at a density of $4 \times 10^4$ cells/well in six-well plates coated with fibronectin. Once the cells reached confluency, the culture medium was replaced with medium containing AraC (5 μg/ml; Sigma) to block further cell division and permit measurement of migration in the absence of proliferation. The scratch wound was made using a p200 pipette tip eight hours after the addition of AraC. Cell migration was monitored over a 24 hour period starting at the time the scratch wound was made and at three-hour intervals thereafter using a Nikon Eclipse TE2000-U microscope under 20× magnification and phase contrast. The percent of the wound remaining open ±SEM was measured at the indicated time points and calculated using Image J, with the 0 hour time point being set to 100%. The percentage of surface not covered by the cells was plotted versus time, and the data were fit to a monoexponential decay curve using Microcal Origin 6.0 to determine the rate at which the cells migrated to fill the exposed area. The distance between the two migrating front lines of cells was measured using the micrometer tool in NIS Elements (Nikon), and the rate of migration was determined and expressed as μM/hr.

CKAP4 C100S does not Localize to the Plasma Membrane

It has been shown previously that CKAP4 is localized to perinuclear ER membranes when DHHC2-mediated palmitoylation is blocked by DHHC2 knockdown (Zhang et al., 2008). To further examine the effect of palmitoylation on CKAP4 localization, WT CKAP4 or the palmitoylation-incompetent mutant, CKAP4 C100S, were stably expressed in HeLa cells and immunocytochemistry was performed. Cells were fixed and incubated with an anti-V5-FITC conjugated monoclonal antibody, and the stably expressed proteins were visualized by epifluorescence microscopy. As shown in FIG. 7A, WT CKAP4 is present on the plasma and perinuclear membranes similar to endogenous CKAP4 localization, while CKAP4 C100S is confined to the ER. Importantly, in cells stably expressing CKAP4 C100S, the ER retains its reticulated structure, radiating throughout the cell. However, when endogenous CKAP4 is unpalmitoylated following DHHC2 knockdown the ER contracts around the nucleus to a greater degree (FIG. 7B). These data corroborate earlier findings indicating that palmitoylation is required for trafficking of CKAP4 from the ER to the plasma membrane (Zhang et al., 2008).

DHHC2 Knockdown Inhibits APF-Stimulated Localization of CKAP4 to the Nucleus

CKAP4 and APF have been shown to colocalize to the plasma membrane and to the perinuclear cytoplasm of NB and HeLa cells (Conrads et al., 2006). To determine if DHHC2-mediated palmitoylation of CKAP4 is required for its nuclear localization upon APF binding, HeLa cells were transfected with DHHC2 siRNA. As shown in FIG. 7B, in cells with reduced DHHC2 expression, CKAP4 is not detected in the nucleus following APF treatment. These data indicate that palmitoylation, and at least temporary residence on the plasma membrane, are required for APF-mediated translocation of CKAP4 to the nucleus.

Figure 8:
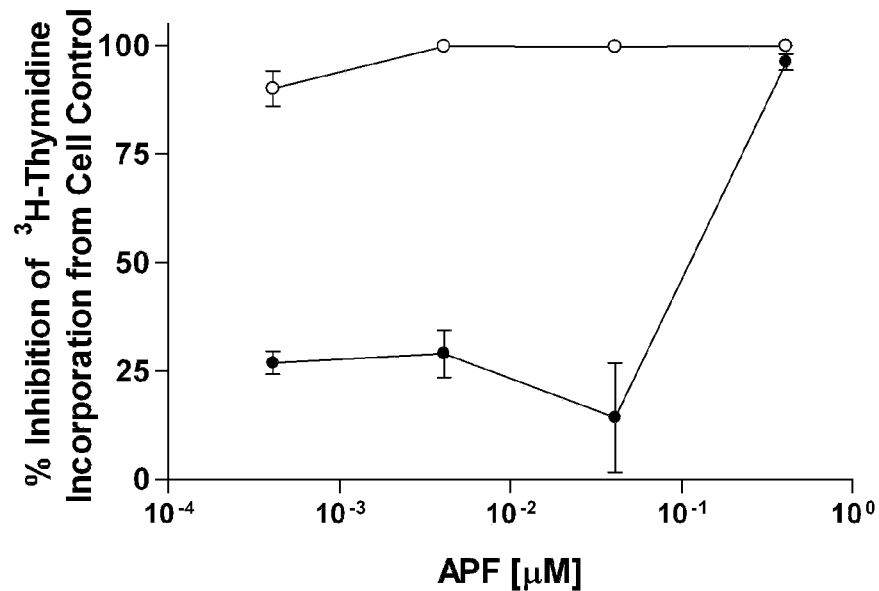
FIGS. 8A-8B demonstrate that siRNA-mediated knockdown of DHHC2 blocks the antiproliferative response of HeLa and NB cells to APF. A) HeLa or B) NB epithelial cells were electroporated with nonsense siRNA (open circles) as a control or with DHHC2 double-stranded siRNA (solid circles) on Day 1, serum-starved on Day 2, and varying concentrations of APF or control peptide (0.25-250 nM) were added to the medium on Day 3; cells were then cultured for an additional 48 hours under conditions of serum starvation. Cellular proliferation was assessed by inhibition of $^3$H-thymidine incorporation. Each data point represents the mean and standard deviation of three independent experiments. Data are presented as percent inhibition of 3H-thymidine incorporation compared to controls. The ability of APF to block proliferation was inhibited in the presence of DHHC2 siRNA for all APF concentrations except 250 nM for HeLa cells, or 25 and 250 nM for NB cells.
Figure 8:
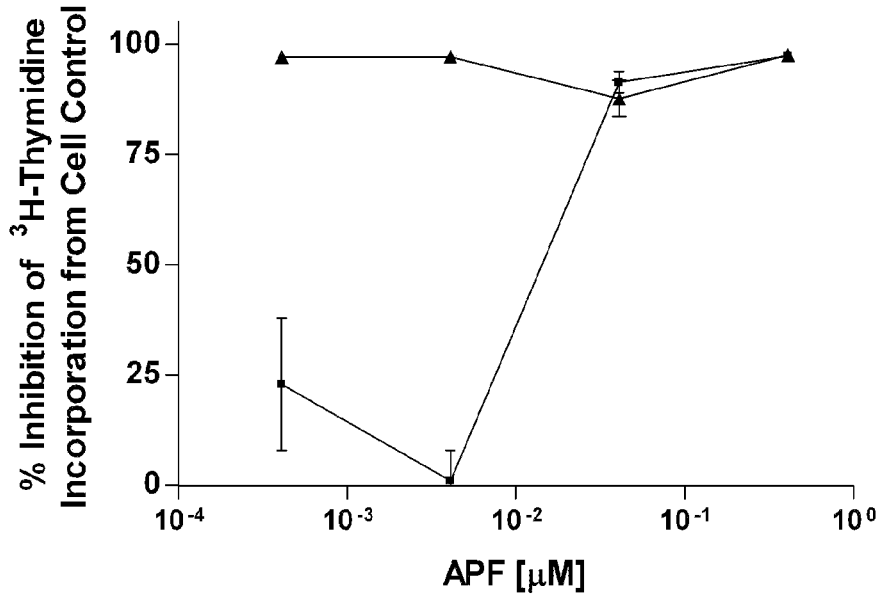

DHHC2 Knockdown Blocks the Antiproliferative Response of Hela and NB Cells to APF Both HeLa and NB epithelial cells express endogenous CKAP4 and have been shown to be sensitive to the antiproliferative effects of APF (Conrads et al., 2006). To determine the effect of reduced CKAP4 palmitoylation on the proliferative response of HeLa and NB cells to APF, the expression of DHHC2 was knocked down using siRNA. Forty-eight hours after siRNA transfection, cells were incubated with varying concentrations of APF. As shown in FIG. 8, APF inhibited HeLa and NB cell proliferation in a concentration dependent manner (FIGS. 8A and 8B, respectively). By contrast, DHHC2 knockdown profoundly inhibited the ability of both cell types to respond to APF. These results demonstrate that DHHC2-mediated palmitoylation of CKAP4 is necessary for APF-induced antiproliferative effects in HeLa and NB cells.

Figure 9:
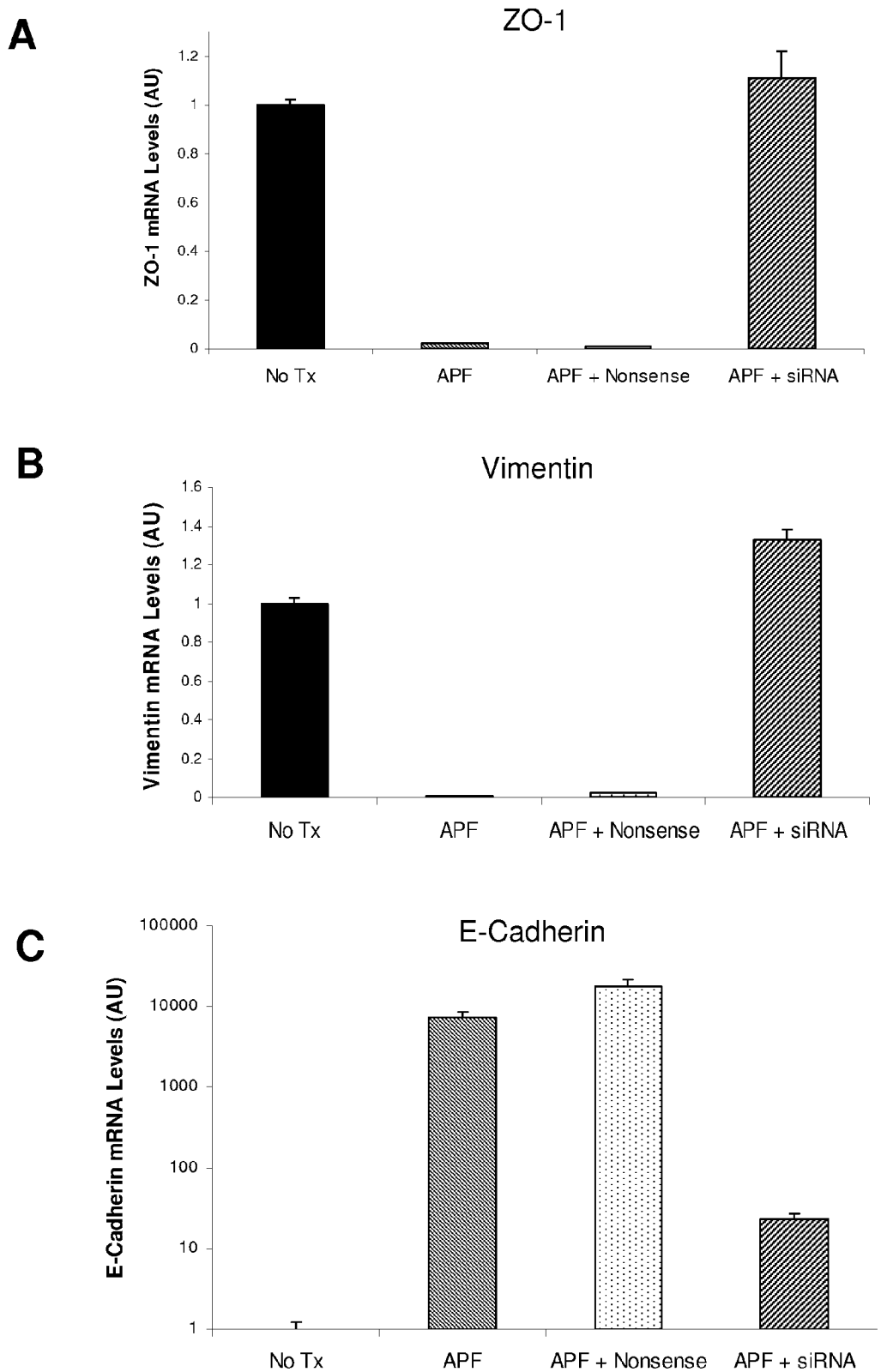
FIGS. 9A-9C show that APF-mediated changes in gene expression are dependent on palmitoylation of CKAP4 by DHHC2 in NB cells. Primary NB epithelial cells were electroporated with nonsense siRNA or with DHHC2 double-stranded siRNA on Day 1, serum-starved on Day 2, and 2.5 nM APF or control peptide were added to the medium on Day 3; cells were then cultured for an additional 48 hours under conditions of serum starvation. Expression of ZO-1, vimentin, and E-cadherin mRNA was assessed by quantitative real-time PCR as described in the Experimental Procedures. A, B) APF alone or in the presence of nonsense siRNA reduced ZO-1 and vimentin mRNA levels by ~93% and ~97%, respectively. DHHC2 knockdown blocked this APF-stimulated reduction in ZO-1 and vimentin mRNA levels. C) APF alone or in the presence of nonsense siRNA dramatically increased E-cadherin mRNA levels, an effect that was also blocked by DHHC2 knockdown. ZO-1, vimentin, and E-cadherin mRNA levels were measured in triplicate runs and quantified by normalization to mRNA levels for β-actin using real-time PCR analysis software from Applied Biosystems. The error in the normalized, relative abundance of each mRNA species was propagated forward from the standard deviation of the mean Ct value for each of the experimental samples and the actin control.
Figure 10:
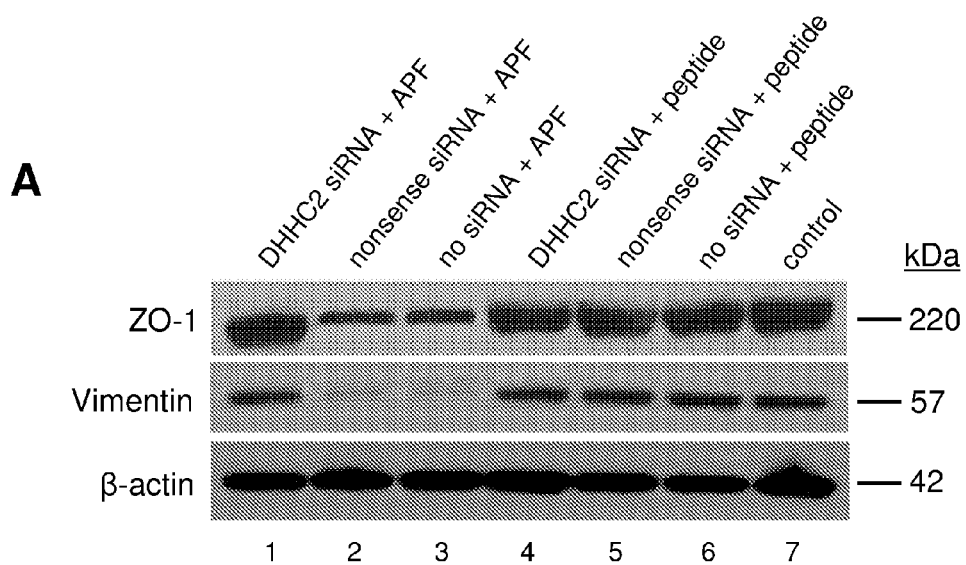
FIGS. 10A-10B demonstrate that APF-mediated changes in protein expression are dependent on palmitoylation of CKAP4 by DHHC2 in NB cells. Primary NB epithelial cells were transfected with DHHC2 double-stranded siRNA on Day 1, serum-starved on Day 2, and 2.5 nM APF or control peptide were added to the medium on Day 3; cells were then cultured for an additional 48 hours under conditions of serum starvation. A) ZO-1 and vimentin protein expression was analyzed by SDS-PAGE followed by Western blotting with antibodies to ZO-1 (220 kDa) and vimentin (57 kDa) as described in Experimental Procedures. To assess equal loading of protein, membranes were stripped and reprobed with a mAb to β-actin (1:5000; Sigma). Proteins were visualized by enhanced chemiluminescence and subsequent exposure to film (BioMaxAR, Kodak) B) The signal intensities for vimentin and ZO-1 were quantified by densitometry using ImageJ, normalized to the corresponding band for β-actin, and reported as the fractional abundance of the control (mock-transfected cells). Results shown are representative of three independent experiments that gave similar results.
Figure 10:
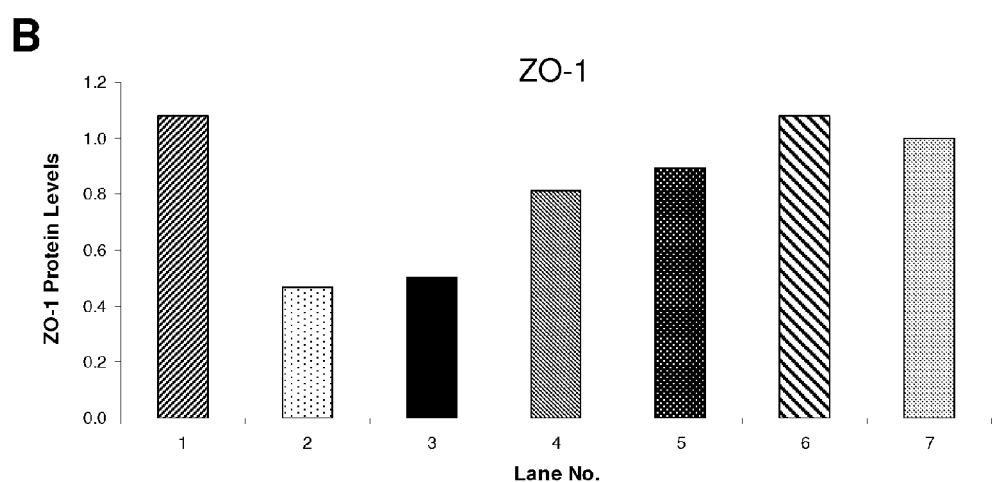
Figure 10:
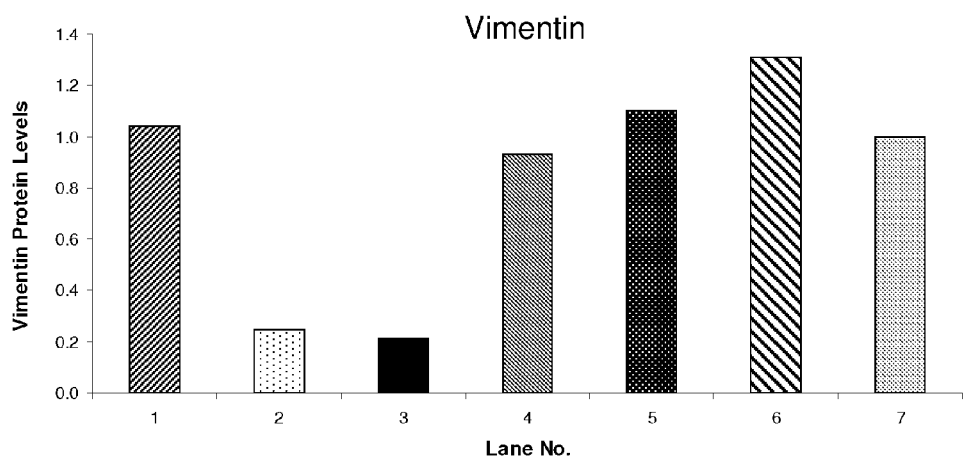

DHHC2 Knockdown Inhibits APF-Induced Changes in Cellular Gene and Protein Expression APF induces multiple changes in the pattern of cellular gene expression including decreased production of vimentin and tight junction proteins (zonula occludens-1 [ZO-1] and occludin) and increased production of E-cadherin, resulting in a more differentiated bladder epithelial cell phenotype (Keay et al., 2003; Kim et al., 2007; Zhang et al., 2005). To determine whether DHHC2 knockdown could affect APF-induced changes in gene and protein expression, confluent NB epithelial cells were treated with APF or inactive peptide control for 48 hours, and the mRNA and protein levels of vimentin, ZO-1, and E-cadherin were determined by quantitative real-time PCR and Western blot analyses, respectively. As has been shown previously, treatment of NB cells with APF significantly reduced mRNA expression of ZO-1 and vimentin (FIGS. 9A and 9B) and increased the expression of E-cadherin relative to untreated cells (FIG. 9C). Remarkably, these changes in gene expression were inhibited in cells transfected with DHHC2 siRNA. Western blot analyses revealed similar reductions in ZO-1 and vimentin protein levels following APF treatment of NB cells which were attenuated when DHHC2 expression was suppressed with siRNA (FIGS. 10A and 10B). Although an increase in E-cadherin mRNA levels could be measured in NB cells following APF treatment, E-cadherin protein expression, in all conditions, remained below the threshold required for Western blot detection.

Figure 11:
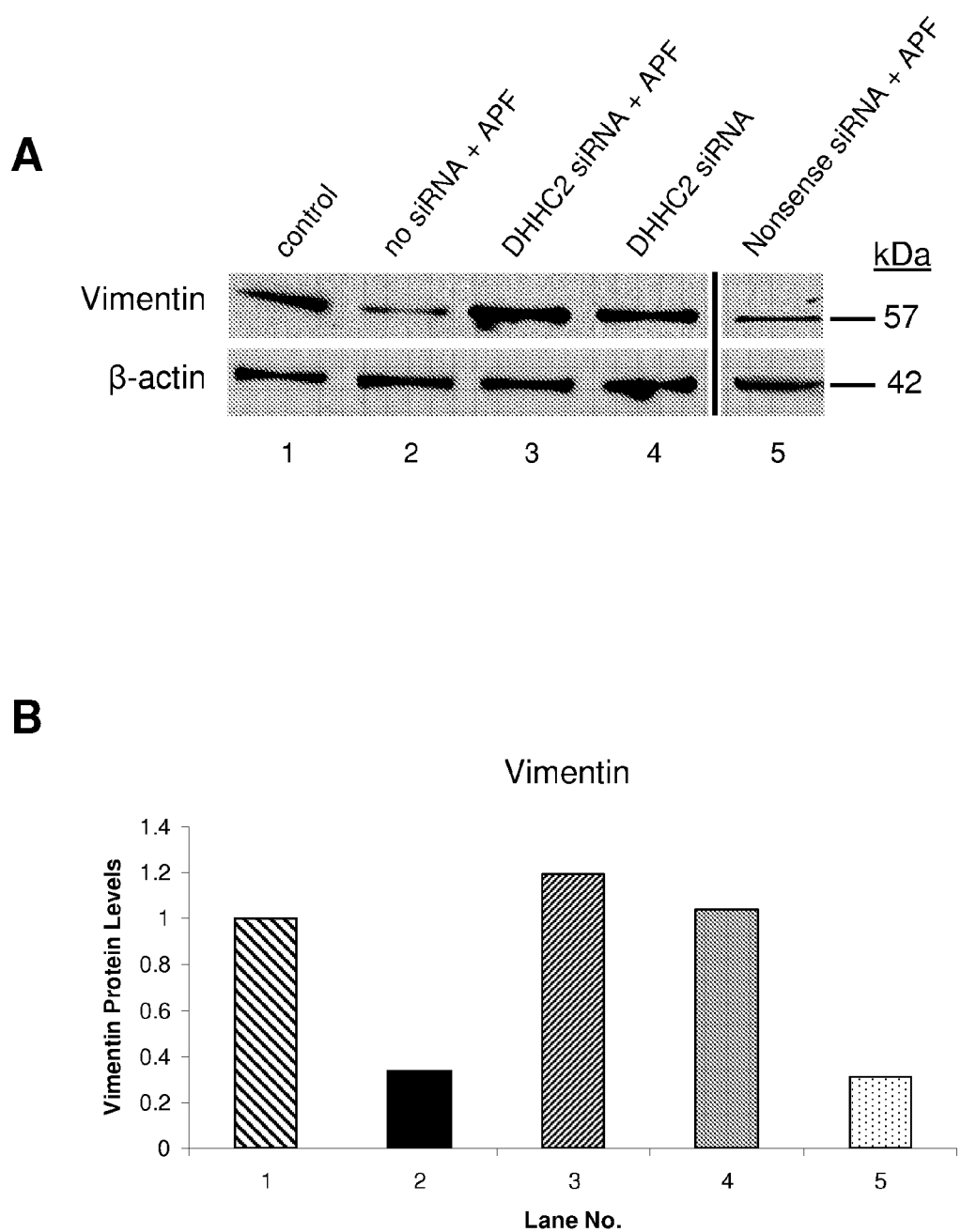
FIGS. 11A-11B show that APF-mediated changes in vimentin protein expression are dependent on palmitoylation of CKAP4 by DHHC2 in HeLa cells. HeLa cells were transfected with DHHC2 double-stranded siRNA, nonsense siRNA, or mock-transfected and cultured for 48 hours. Cells were then serum-starved, and the indicated cultures incubated with APF (20 nM) for an additional 48 hours. A) Expression of vimentin protein was analyzed by SDS-PAGE and Western blotting with a mAb antibody against vimentin (57 kDa) as described in Experimental Procedures. To assess equal loading of protein, membranes were stripped and reprobed with a mAb to β-actin (1:5000; Sigma). Proteins were visualized by enhanced chemiluminescence and subsequent exposure to film (BioMaxAR, Kodak). B) The signal intensity for vimentin was quantified by densitometry using ImageJ, normalized to the corresponding band for β-actin, and reported as the fractional abundance of the control (mock-transfected cells). Results shown are representative of three independent experiments that gave similar results.

While APF has been shown to inhibit HeLa cell proliferation, APF-induced changes in cellular gene expression have not been documented for this cell line. As shown in FIG. 11, APF treatment also reduced the expression of vimentin in HeLa cells. Changes in the expression of ZO-1 and E-cadherin could not be measured accurately by quantitative real-time PCR or by Western blot as their abundance in HeLa cells was too low. Importantly, as observed in NB cells, transfection of HeLa cells with DHHC2 siRNA inhibited the APF-mediated downregulation of vimentin expression. These data demonstrate that DHHC2-mediated palmitoylation of CKAP4 is necessary for APF to induce changes in gene and protein expression in both normal epithelial (NB) and carcinoma (HeLa) cells.

Figure 12:
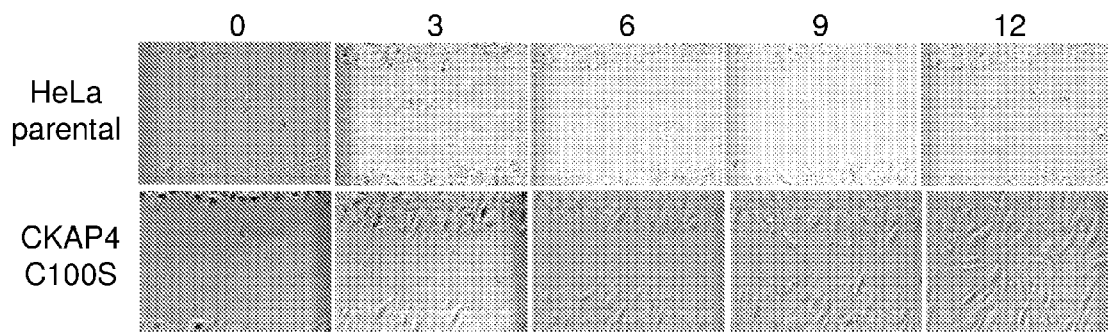
FIGS. 12A-12B show that stable CKAP4 C100S expression increases the migratory rate of HeLa cells. HeLa cells stably transfected with CKAP4 C100S or parental controls were seeded in fibronectin-coated, 6-well plates and grown to confluence. To permit measurement of migration in the absence of proliferation, cells were treated with AraC (5 μg/ml; Sigma), blocking further cell division. After 8 hours in AraC, a line of adherent cells was scraped from the bottom of each well with a p-200 pipette tip to generate a "wound." A) Cells were allowed to migrate into the wound for 24 hours, and the extent of migration into the region from which cells had been scraped was determined from consecutive images of the same field of view taken at 3-hour intervals. Cells were photographed using a Nikon Eclipse TE2000-U microscope under 20× magnification and phase contrast. B) The cell-free area introduced by each wound was measured using ImageJ and converted to a percentage of area at time 0 plotted against time. These data were fit to a monoexponential decay curve (Microcal Origin, Northampton Mass.). The T1/2 rate for migration of cells into the wound was calculated to be 2.3 hours for CKAP4 C100S overexpressing cells (curved line); parental HeLa cells did not migrate into the wound during the course of these experiments (horizontal line of diamonds across the top of the graph).
Figure 12:
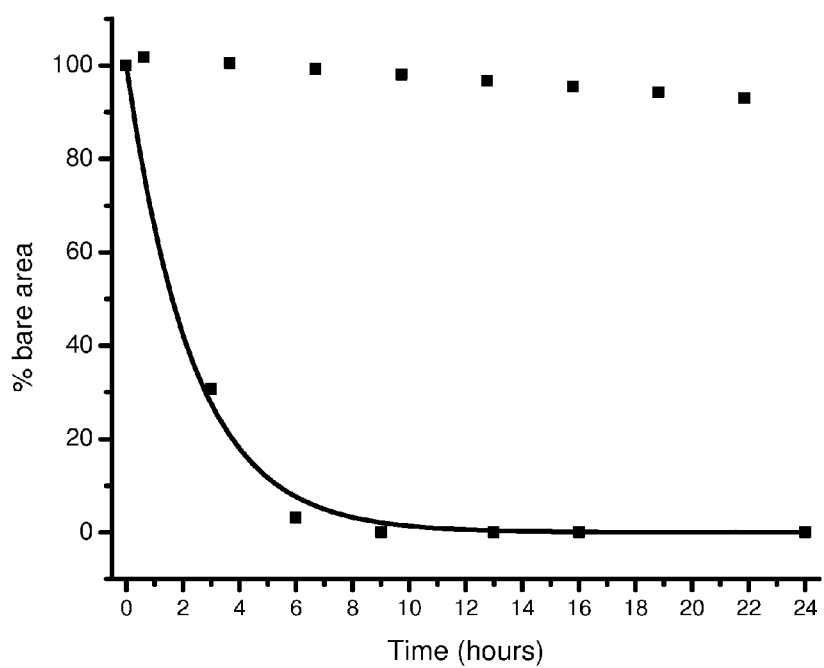

Stable CKAP4 C100S Expression Increases the Migratory Rate of HeLa Cells: Wound Healing Assay Because APF induces changes in the expression of genes involved in cell migration and adhesion, and DHHC2 knockdown inhibits these changes, the ability of HeLa cells stably expressing CKAP4 C100S to migrate by a wound healing assay was measured (FIG. 12). Overexpression of CKAP4 C100S accelerated the migratory rate of HeLa cells by 8.7 fold compared to the parental control (166 µm/hr versus 19 µm/hr, respectively) (FIG. 12B); moreover, CKAP4 C100S-expressing cells refilled the wound area with a t1/2 of 2.3 hours, while the parental control cells did not refill the area during the 24-hour observation period (FIG. 12A). These results suggest that CKAP4 is the substrate of DHHC2 that mediates changes in cellular behavior related to increased metastasis when DHHC2 is not expressed (Oyama et al., 2000).

Example 6

Significance of the Present Invention

Thus, in the present invention, it is demonstrated that palmitoylation of CKAP4 by DHHC2 is a key regulatory link between APF-mediated signaling events such as nuclear translocation of CKAP4 and changes in cellular gene and protein expression. Additionally, there is an increased rate of cellular migration when CKAP4 C100S is stably expressed in HeLa cells, providing the first molecular mechanism linking reduced DHHC2 expression to increased metastatic cellular behavior.

Figure 7:
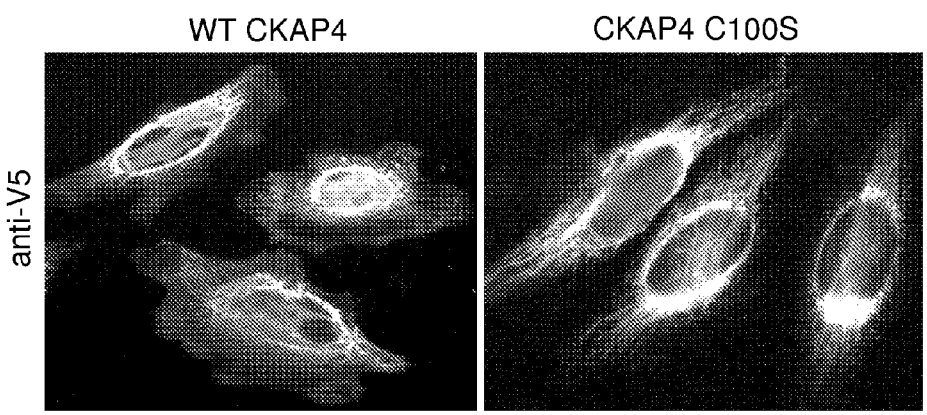
FIGS. 7A-7B show that DHHC2-mediated palmitoylation of CKAP4 on cysteine 100 regulates its trafficking from the ER to the PM and from the PM to the nucleus/nucleolus following APF binding. A) HeLa cell lines stably expressing CKAP4 WT-V5 or the palmitoylation-incompetent mutant, CKAP4 C100S-V5, were grown on LabTek multiwell glass slides (Nalge Nunc), fixed, and immunolabeled with a FITC-conjugated mAb antibody against the V5 epitope (1:5000; Invitrogen). CKAP4 WT was expressed on the plasma membrane and perinuclear membranes, whereas CKAP4 C100S expression was restricted to the ER. B) Mock-transfected or DHHC2 siRNA-transfected HeLa cells were treated with APF (20 nM) for 48 hours. Cells were fixed and incubated with a mAb G1/296 against CKAP4 ("anti-CLIMP-63", Alexis Biochemicals) followed by a TRITC-labeled, goat anti-mouse secondary antibody (Jackson ImmunoResearch Laboratories). CKAP4 was translocated to the nucleus and nucleolus in HeLa cells treated with APF; however, this translocation was blocked in APF-treated HeLa cells transfected with DHHC2 siRNA. Epifluorescence images in A were made with a 100×, 1.45 NA oil immersion objective (Nikon) and those in B, with a 60×1.45 NA oil immersion objective (Nikon).
Figure 7:
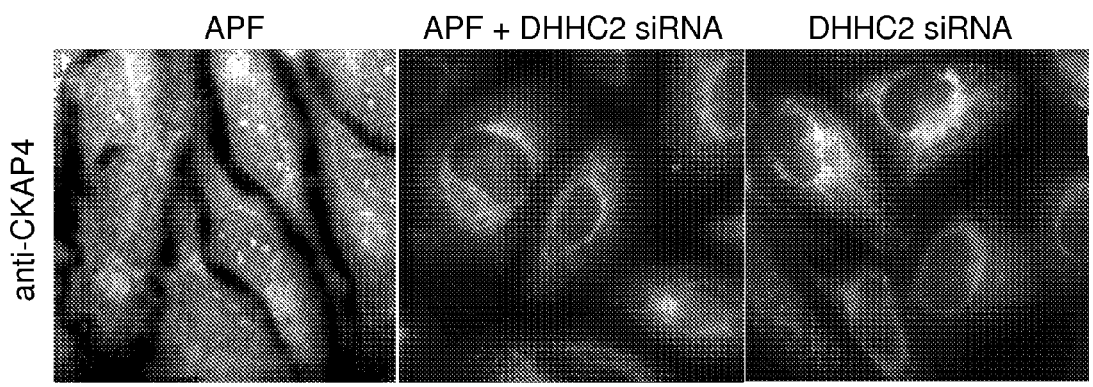

Immunolabeling of stably expressed WT CKAP4 and the palmitoylation incompetent mutant, CKAP4 C100S, was similar to the staining pattern for CKAP4 that was observed in response to DHHC2 knockdown in previous studies—WT CKAP4 was expressed on endomembranes, ER that extended throughout the cytoplasm, and the plasma membrane, while CKAP4 C100S was confined to endomembranes (see FIG. 7). However, the extensive tubular ER network was retained in cells stably expressing CKAP4 C100S, presumably because endogenous, palmitoylated CKAP4 maintained its overall structure. By contrast, the ability to maintain the tubular ER network is lost with DHHC2 knockdown because a significant population of endogenous CKAP4 is depalmitoylated. Vedrenne and colleagues (2005) have reported a similar collapse of the ER in cells expressing CKAP4 phosphomimicking mutants that are unable to bind to microtubules (Vedrenne et al., 2005). In cells expressing these mutants, the ER retracts around the nucleus while leaving the microtubular network intact, suggesting that stable anchoring of the ER to microtubules by CKAP4 is required to maintain its spatial distribution. Collectively, these findings indicate that palmitoylation by DHHC2 is required to maintain CKAP4 in a dephosphorylated, microtubule-anchored state, in particular embodiments of the invention.

APF stimulation results in translocation of CKAP4 and APF to the nucleus (Conrads et al., 2006), yet the mechanisms mediating this translocation remain elusive. It is possible that the CKAP4-APF complex is internalized by clathrin-dependent, receptor-mediated endocytosis, as is the case when SP-A binds to CKAP4 (Gupta et al., 2006). However, the mechanism by which CKAP4 escapes from endocytic vesicles and enters the nucleus/nucleolus is unknown.

APF profoundly inhibits cellular proliferation and induces changes in the expression of genes involved in cell migration and adhesion with a concomitant change in the phenotype of the cells toward a more differentiated state (Keay et al., 2003; Zhang et al., 2005). APF produces these effects by binding with high affinity to CKAP4 (Conrads et al., 2006). The data demonstrate that DHHC2-mediated palmitoylation of CKAP4 is necessary for APF-mediated changes in proliferation and gene expression. These results indicate that the downstream effects of APF are mediated through CKAP4, and that palmitoylation of CKAP4 occurs primarily via DHHC2, since loss of DHHC2 expression by siRNA-mediated knockdown is sufficient to block APF- and CKAP4-dependent signaling. These results are consistent with the idea that CKAP4 residence on the plasma membrane is required for APF-driven cellular responses, and that in HeLa and normal bladder epithelial cells APF does not act (with respect to the metrics that were analyzed) by binding to CKAP4 on the ER (regardless of its palmitoylation state).

The increased migration rate of cells expressing CKAP4 C100S is consistent with data reported by Oyama and colleagues (2000) correlating reduced ZDHHC2 mRNA expression to increased metastatic behavior of cells in vitro and in vivo (Oyama et al., 2000). It is not clear how overexpression of the palmitoylation-incompetent CKAP4 C100S mutant translates into an increased rate of cellular migration.

The significance of DHHC2-mediated palmitoylation of CKAP4 to human health and disease extends beyond IC, in certain embodiments of the invention. CKAP4 has also been identified as a functional, cell-surface receptor for tissue plasminogen activator (tPA) in vascular smooth muscle cells and for surfactant protein A (SP-A) in rat type II pneumocytes (Gupta et al., 2006; Heinrich et al., 2006). Like APF, tPA regulates cellular proliferation, migration, and invasion in the vasculature—behaviors that are also critically relevant to IC and cancer. tPA binding to CKAP4 on the plasma membrane regulates the response of vascular smooth muscle cells (VSMCs) to a variety of blood vessel injuries (Heinrch et al., 2006). Following vascular injury, tPA stimulates VSMC migration, and remodeling of the surrounding extracellular matrix, key features that promote vascular repair. SP-A levels are decreased in the lungs of patients with cystic fibrosis, respiratory distress syndrome, as well as chronic lung diseases (Nadolski and Linder, 2007). It is thought that CKAP4 may play a role in SP-A recycling and SP-A signaling by mediating transport of SP-A from the ER to the plasma membrane and/or in SP-A binding at the plasma membrane and subsequent internalization (Gupta et al., 2006).

The data presented here indicate an increasingly complex role for CKAP4 in the regulation of several cellular signaling pathways and behaviors. In addition, they highlight a unique role for CKAP4 in cellular migration. This is the first report of a transiently-palmitoylated, transmembrane receptor protein that is trafficked to the nucleolus. In specific embodiments, CKAP4 resides in the nucleolus only when bound by a ligand such as APF, because nucleolar localization of CKAP4 in untreated HeLa cells has not been observed, and nuclear translocation to the nucleus or nucleolus following binding of tPA or SPA was also not apparent in previous studies (Gupta et al., 2006; Heinrich et al., 2006). Palmitoylation has been shown to be important in regulating the subcellular distribution and function of many proteins with key regulatory roles in diverse signaling networks (Linder and Dechenes, 2007). There is relatively little known about the 23 members of the mammalian PAT family in terms of their regulation and specificity for substrates. However, the remarkable number of known associations between disease and the genes that encode PATs demonstrates the importance of palmitoylation for human health, especially cancer. The identification of CKAP4 as the substrate for DHHC2 and the functional significance of CKAP4 palmitoylation in cellular behavior related to cancer and IC illustrate the wide-ranging significance of palmitoylation.

REFERENCES

All patents, patent applications, and publications mentioned in the specifications are indicative of the levels of those skilled in the art to which the invention pertains. All patents, patent applications, and publications are herein incorporated by reference to the same extent as if each individual publication was specifically and individually indicated to be incorporated by reference.

PATENTS AND PATENT APPLICATIONS

U.S. Pat. No. 4,683,202
U.S. Pat. No. 4,684,611
U.S. Pat. No. 4,797,368
U.S. Pat. No. 4,952,500
U.S. Pat. No. 5,139,941
U.S. Pat. No. 5,302,523
U.S. Pat. No. 5,322,783
U.S. Pat. No. 5,464,765
U.S. Pat. No. 5,589,466
U.S. Pat. No. 5,580,859
U.S. Pat. No. 5,550,318
U.S. Pat. No. 5,538,877
U.S. Pat. No. 5,538,880
U.S. Pat. No. 5,591,616
U.S. Pat. No. 5,563,055
U.S. Pat. No. 5,610,042
U.S. Pat. No. 5,656,610
U.S. Pat. No. 5,563,055
U.S. Pat. No. 5,702,932
U.S. Pat. No. 5,789,215
U.S. Pat. No. 5,780,448
U.S. Pat. No. 5,736,524
U.S. Pat. No. 5,925,565
U.S. Pat. No. 5,928,906
U.S. Pat. No. 5,935,819
U.S. Pat. No. 5,994,136
U.S. Pat. No. 5,994,624
U.S. Pat. No. 5,981,274
U.S. Pat. No. 5,945,100
U.S. Pat. No. 6,013,516
U.S. Pat. No. 6,617,438
U.S. Pat. No. 6,818,447
U.S. Pat. No. 7,022,828
U.S. Pat. No. 7,345,027
PCT Application No. WO 94/09699
PCT Application No. WO 95/06128

PUBLICATIONS

Anbazhagan, R., Fujii, H., and Gabrielson, E. (1998) *Am J Pathol* 152, 815-819

Bano, M. C., Jackson, C. S., and Magee, A. I. (1998) *Biochem J* 330 (Pt 2), 723-731

Bizzozero, O. A., McGarry, J. F., and Lees, M. B. (1987) *J Biol Chem* 262, 13550-13557

Bova, G. S., Carter, B. S., Bussemakers, M. J., Emi, M., Fujiwara, Y., Kyprianou, N., Jacobs, S. C., Robinson, J. C., Epstein, J. I., Walsh, P. C., and et al. (1993) *Cancer Res* 53, 3869-3873

Conrads, T. P., Tocci, G. M., Hood, B. L., Zhang, C. O., Guo, L., Koch, K. R., Michejda, C. J., Veenstra, T. D., and Keay, S. K. (2006) *J Biol Chem* 281, 37836-37843

Conrads, T. P., Tocci, G. M., Hood, B. L., Zhang, C. O., Guo, L., Koch, K. R., Michejda, C. J., Veenstra, T. D., and Keay, S. K. (2006) J Biol Chem December 8; 281(49):37836-43

Drisdel, R. C., Manzana, E., and Green, W. N. (2004) J Neurosci 24, 10502-10510 el-Husseini Ael, D., and Bredt, D. S. (2002) *Nat Rev Neurosci* 3, 791-802

Emi, M., Fujiwara, Y., Ohata, H., Tsuda, H., Hirohashi, S., Koike, M., Miyaki, M., Monden, M., and Nakamura, Y. (1993) *Genes Chromosomes Cancer* 7, 152-157

Fujiwara, Y., Emi, M., Ohata, H., Kato, Y., Nakajima, T., Mori, T., and Nakamura, Y. (1993) *Cancer Res* 53, 1172-1174

Fujiwara, Y., Ohata, H., Emi, M., Okui, K., Koyama, K., Tsuchiya, E., Nakajima, T., Monden, M., Mori, T., Kurimasa, A., and et al. (1994) *Genes Chromosomes Cancer* 10, 7-14

Fukata, M., Fukata, Y., Adesnik, H., Nicoll, R. A., and Bredt, D. S. (2004) *Neuron* 44, 987-996

Fukata, Y., Iwanaga, T., and Fukata, M. (2006) Methods 40, 177-182

Greaves, J., and Chamberlain, L. H. (2007) *J Cell Biol* 176, 249-254

Gupta, N., Manevich, Y., Kazi, A. S., Tao, J. Q., Fisher, A. B., and Bates, S. R. (2006) *Am J Physiol Lung Cell Mol Physiol* 291, L436-446

Heid, C. A., Stevens, J., Livak, K. J., and Williams, P. M. (1996) Genome Res 6, 986-994

Heinrich, S., Hard, D., and Griese, M. (2006) *Curr Med Chem* 13, 3239-3252

Ichii, S., Takeda, S., Horii, A., Nakatsuru, S., Miyoshi, Y., Emi, M., Fujiwara, Y., Koyama, K., Furuyama, J., Utsunomiya, J., and et al. (1993) *Oncogene* 8, 2399-2405

Jones, A., Korpi, E. R., McKernan, R. M., Pelz, R., Nusser, Z., Makela, R., Mellor, J. R., Pollard, S., Bahn, S., Stephenson, F. A., Randall, A. D., Sieghart, W., Somogyi, P., Smith, A. J., and Wisden, W. (1997) *J Neurosci* 17, 1350-1362

Keay, S. K., Szekely, Z., Conrads, T. P., Veenstra, T. D., Barchi, J. J., Jr., Zhang, C. O., Koch, K. R., and Michejda, C. J. (2004) *Proc Natl Acad Sci USA* 101, 11803-11808

Keay, S., Kleinberg, M., Zhang, C. O., Hise, M. K., and Warren, J. W. (2000) *J Urol* 164, 2112-2118

Keay, S., Zhang, C. O., Chai, T., Warren, J., Koch, K., Grkovic, D., Colville, H., and Alexander, R. (2004) *Urology* 63, 22-26

Keay, S., Zhang, C. O., Trifillis, A. L., Hise, M. K., Hebel, J. R., Jacobs, S. C., and Warren, J. W. (1996) *J Urol* 156, 2073-2078

Keay, S., Tocci, G., Koch, K., Zhang, C., Grkovic, D., and Michejda, C. J. (2006) *European Journal of Cancer Supplements* 4, 87-88

Keay, S., Seillier-Moiseiwitsch, F., Zhang, C. O., Chai, T. C., and Zhang, J. (2003) *Physiol Genomics* 14, 107-115

Keay, S., Kleinberg, M., Zhang, C. O., Hise, M. K., and Warren, J. W. (2000) J Urol 164, 2112-2118

Keller, C. A., Yuan, X., Panzanelli, P., Martin, M. L., Alldred, M., Sassoe-Pognetto, M., and Luscher, B. (2004) J Neurosci 24, 5881-5891

Khubchandani, K. R., and Snyder, J. M. (2001) Faseb J 15, 59-69

Kim, J., Keay, S. K., Dimitrakov, J. D., and Freeman, M. R. (2007) *FEBS Lett* 581, 3795-3799

Klopfenstein, D. R., Kappeler, F., and Hauri, H. P. (1998) *Embo J* 17, 6168-6177

Klopfenstein, D. R., Klumperman, J., Lustig, A., Kammerer, R. A., Oorschot, V., and Hauri, H. P. (2001) J Cell Biol 153, 1287-1300

Knowles, M. A., Shaw, M. E., and Proctor, A. J. (1993) *Oncogene* 8, 1357-1364

Linder, M. E., and Deschenes, R. J. (2007) *Nat Rev Mol Cell Biol* 8, 74-84

Lobo, S., Greentree, W. K., Linder, M. E., and Deschenes, R. J. (2002) *J Biol Chem* 277, 41268-41273

Mansouri, M. R., Marklund, L., Gustaysson, P., Davey, E., Carlsson, B., Larsson, C., White, I., Gustayson, K. H., and Dahl, N. (2005) *Eur J Hum Genet* 13, 970-977

Mikic, I., Planey, S., Zhang, J., Ceballos, C., Seron, T., Massenbach, B. v., Watson, R., Callaway, S., Price, J., Hunter, E., and Zacharias, D. (2006) Methods in Enzymology 414

Moran, L. K., Gutteridge, J. M., and Quinlan, G. J. (2001) *Curr Med Chem* 8, 763-772

Mukai, J., Liu, H., Burt, R. A., Swor, D. E., Lai, W. S., Karayiorgou, M., and Gogos, J. A. (2004) *Nat Genet* 36, 725-731

Nadolski, M. J., and Linder, M. E. (2007) *Febs J* 274, 5202-5210

Ohata, H., Emi, M., Fujiwara, Y., Higashino, K., Nakagawa, K., Futagami, R., Tsuchiya, E., and Nakamura, Y. (1993) *Genes Chromosomes Cancer* 7, 85-88

Oyama, T., Miyoshi, Y., Koyama, K., Nakagawa, H., Yamori, T., Ito, T., Matsuda, H., Arakawa, H., and Nakamura, Y. (2000) *Genes Chromosomes Cancer* 29, 9-15

Raymond, F. L., Tarpey, P. S., Edkins, S., Tofts, C., O'Meara, S., Teague, J., Butler, A., Stevens, C., Barthorpe, S., Buck, G., Cole, J., Dicks, E., Gray, K., Halliday, K., Hills, K., Hinton, J., Jones, D., Menzies, A., Perry, J., Raine, K., Shepherd, R., Small, A., Varian, J., Widaa, S., Mallya, U., Moon, J., Luo, Y., Shaw, M., Boyle, J., Kerr, B., Turner, G., Quarrell, O., Cole, T., Easton, D. F., Wooster, R., Bobrow, M., Schwartz, C. E., Gecz, J., Stratton, M. R., and Futreal, P. A. (2007) *Am J Hum Genet* 80, 982-987

Razzaq, T. M., Bass, R., Vines, D. J., Werner, F., Whawell, S. A., and Ellis, V. (2003) J Biol Chem 278, 42679-42685

Resh, M. D., (2006) *Sci STKE* 2006, re14

Roth, A. F., Feng, Y., Chen, L., and Davis, N. G. (2002) *J Cell Biol* 159, 23-28

Schweizer, A., Rohrer, J., and Kornfeld, S. (1995) *J Biol Chem* 270, 9638-9644

Schweizer, A., Ericsson, M., Bachi, T., Griffiths, G., and Hauri, H. P. (1993) *J Cell Sci* 104 (Pt 3), 671-683

Schweizer, A., Rohrer, J., Hauri, H. P., and Kornfeld, S. (1994) *J Cell Biol* 126, 25-39

Schweizer, A., Rohrer, J., Jeno, P., DeMaio, A., Buchman, T. G., and Hauri, H. P. (1993) *J Cell Sci* 104 (Pt 3), 685-694

Smotrys, J. E., and Linder, M. E. (2004) *Annu Rev Biochem* 73, 559-587

Tsuruo, T., Yamori, T., Naganuma, K., Tsukagoshi, S., and Sakurai, Y. (1983) *Cancer Res* 43, 5437-5442

Vedrenne, C., and Hauri, H. P. (2006) *Traffic* 7, 639-646

Vedrenne, C., Klopfenstein, D. R., and Hauri, H. P. (2005) Mol Biol Cell 16, 1928-1937 20 Loisel, T. P., Adam, L., Hebert, T. E., and Bouvier, M. (1996) Biochemistry 35, 15923-15932

Wedegaertner, P. B., and Bourne, H. R. (1994) *Cell* 77, 1063-1070

Wong, M. L., and Medrano, J. F. (2005) Biotechniques 39, 75-85

Yamamoto, Y., Chochi, Y., Matsuyama, H., Eguchi, S., Kawauchi, S., Furuya, T., Oga, A., Kang, J. J., Naito, K., and Sasaki, K. (2007) *Oncology* 72, 132-138

Yanai, A., Huang, K., Kang, R., Singaraja, R. R., Arstikaitis, P., Gan, L., Orban, P. C., Mullard, A., Cowan, C. M., Raymond, L. A., Drisdel, R. C., Green, W. N., Ravikumar, B., Rubinsztein, D. C., El-Husseini, A., and Hayden, M. R. (2006) *Nat Neurosci*

Yaremko, M. L., Kutza, C., Lyzak, J., Mick, R., Recant, W. M., and Westbrook, C. A. (1996) *Genes Chromosomes Cancer* 16, 189-195

Zacharias, D. A., Violin, J. D., Newton, A. C., and Tsien, R. Y. (2002) *Science* 296, 913-916

Zhang, C. O., Wang, J. Y., Koch, K. R., and Keay, S. (2005) *J Urol* 174, 2382-2387

Zhang, J., Planey, S. L., Ceballos, C., Stevens, S. M., Jr., Keay, S. K., and Zacharias, D. A. (2008) *Mol Cell Proteomics*

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of modulating activity of antiproliferative factor in an individual, comprising delivering to the individual a therapeutically effective amount of an agent that inhibits palmitoyl acyl transferase, wherein the palmitoyl acyl transferase is DHHC2.

2. The method of claim 1, wherein the agent is a nucleic acid, protein, small molecule, or a mixture thereof.

3. The method of claim 1, wherein the nucleic acid comprises siRNA.

4. The method of claim 1, wherein the delivering step improves at least one symptom of a bladder condition.

5. The method of claim 4, wherein the bladder condition is interstitial cystitis.

6. The method of claim 4, wherein the individual is further provided an additional interstitial cystitis therapy.

* * * * *

SEQUENCE LISTING

<160> NUMBER OF SEQ ID NOS: 58

<210> SEQ ID NO 1
<211> LENGTH: 3837
<212> TYPE: DNA

<213> ORGANISM: Human

<400> SEQUENCE: 1

| | | | | | |
|---|---|---|---|---|---|
| gccgggctga | ggagccggga | gtccgccgcg | ccggctcggg | gctgcgggat | ggggagttag | 60 |
| cgccacggcg | gcggcagtgg | ccgcagcgca | ccccgccgcc | gcccaggagc | ccgtccagcc | 120 |
| aggggtgccg | ggcccgccca | gcccgccccg | gagccaggcc | cgcgggcggc | ggcggagctg | 180 |
| ggcaggtgga | tgcggctgga | agatggcgcc | ctcgggcccg | ggcagcagcg | ccaggcggcg | 240 |
| gtgccggcgg | gtgctgtact | ggatcccggt | ggtgttcatc | accctcctgc | tcggctggtc | 300 |
| ctactacgcc | tacgccatcc | agctgtgcat | agtgtccatg | gaaaacactg | gcgaacaagt | 360 |
| tgtgtgcctg | atggcctatc | atctactttt | tgcaatgttt | gtctggtcat | actggaaaac | 420 |
| tatctttaca | ttaccaatga | atccttcaaa | agaattccat | ctctcttatg | cagagaaaga | 480 |
| tttgttggag | agagagccaa | gaggagaagc | ccatcaggaa | gttcttaggc | gagcagccaa | 540 |
| ggatcttccc | atctatacca | ggaccatgtc | tggagccatc | cgatactgtg | acagatgcca | 600 |
| acttataaaa | ccagatcgct | gccatcactg | ctccgtctgt | gataaatgta | ttttgaagat | 660 |
| ggatcatcat | tgtccatggg | tgaacaattg | tgttggattt | tcaaattata | agttctttct | 720 |
| cctttttcttg | gcttattctc | tgctctactg | cctttttatt | gcggcaacag | atttacagta | 780 |
| ttttatcaaa | ttttggacaa | atggcctacc | tgatactcaa | gccaagttcc | atattatgtt | 840 |
| tttattcttt | gctgcagcta | tgttttctgt | cagcttgtct | tctctgtttg | gctatcattg | 900 |
| ttggctagtc | agcaaaaata | aatctacatt | agaggcattc | agaagtccag | tatttcgaca | 960 |
| tggaacagat | aagaatggat | tcagcttggg | tttcagtaaa | aacatgcgac | aagttttttgg | 1020 |
| tgatgagaag | aagtactggt | tgctacccat | tttttcaagt | ctaggtgatg | gctgctcctt | 1080 |
| tccaacttgc | cttgttaacc | aggatcctga | acaagcatct | actcctgcag | ggctgaattc | 1140 |
| cacagctaaa | aatctcgaaa | accatcagtt | tcctgcaaag | ccattgagag | agtcccagag | 1200 |
| ccaccttctt | actgattctc | agtcttggac | ggagagcagc | ataaacccag | gaaaatgcaa | 1260 |
| agctggtatg | agcaatcctg | cattaaccat | ggaaaatgag | acttaactct | tcaagcaaga | 1320 |
| taaattcata | ctttataaaa | gtatcaatgc | tgtagatgga | tggaagaggc | ttcccacagg | 1380 |
| aaggtgccac | cagtcagttg | tgcctatgtc | cctttggctg | gaaatgcaga | atatgaattg | 1440 |
| attagttctc | tccaagccat | tgcttaaaat | ataacatgtt | ttggatccaa | tacacacatt | 1500 |
| gttacaacta | acacaaattc | ctattaaata | ttaaaagtag | ttctggttta | ttaatcaacg | 1560 |
| gggaaaacat | cttctccaaa | aaacttggaa | taaatccaag | gaccagtttt | tacccaaata | 1620 |
| tatgggtagc | acagtttatc | acatagaaac | tccattaatc | atctgatttt | ccgaatctga | 1680 |
| aaattgagac | tattaagata | ttaagatttc | agagatttca | agtcacatta | taatgataag | 1740 |
| cattattcat | aaaacttgtt | acctttaaga | aggtggaagt | ggcaaaccat | acttctttt | 1800 |
| ttttcctctg | atgtgaatcc | agcctcagac | tgagtgaact | gtaataatta | tgaattcatt | 1860 |
| acagagtcca | ggtggcctgc | agttgaagat | catcaaccat | ttttgcctca | cttaattcca | 1920 |
| gcctttgtt | ttctgctgga | aaataagtgt | ggacattgaa | gcttgagctc | tcaaagcagt | 1980 |
| tggctggaat | acttttgtca | gaatacggta | catttctatt | acatcagaaa | tatattttca | 2040 |
| tctcttcttg | ttaaatttggg | aggaaattta | tgatagcaat | tatgaagatt | gttttatgac | 2100 |
| attcttttgt | cagtttggct | ttctaaaaat | ctcttttttag | attatttctc | ctgttgaaca | 2160 |
| tagtaaaact | attgaatttc | tcttaagaat | tcctaatagg | tcaatagatt | taccctccag | 2220 |
| tgatatctat | attatttctt | tctcgtctca | tcaaaatgat | gacaggtaaa | ctatatttt | 2280 |

-continued

| | |
|---|---|
| ccttaaacac ctattacagt taaattatgc aaatcattaa ataaaaatca tacaactttt | 2340 |
| ggaaagttag ttcaacatga actaaaatgg catgctattt ggaaatttag tttgagataa | 2400 |
| actaaagtgt gttgatgcca gaatgttcag cttcagtaaa tataataagc tcttgtgcct | 2460 |
| tgtatgcact atttaaaaaa agttttttt atttgagtcc agtataattc atgtaaatgt | 2520 |
| taacaattag aataatactc tgtatgcttt tttgatactg attttgagaa tttaaagcag | 2580 |
| attaccttt aaaactggac caactaagta attggtattt aatcaaagag aaaatggtaa | 2640 |
| taaactttc aaaatctttg ttaaaccaaa cattcaacac aaaataaact agaaggccag | 2700 |
| aggataatgg aataaaagat cattgcaatt acttatcctt cctaaaaata tagttttata | 2760 |
| ttaattgtgc ttatggaaga aacaatgtca gccaagtcca ttttatagtt tgagtgcaat | 2820 |
| tctttgaaca atagaaatat ctgcagtctt tcacagattt gtattatgct gaagagtttc | 2880 |
| atctgacaat ctgcttcaag aaatctcaga aaatatgata acattttaac tttcgtttta | 2940 |
| gagcacgttt tggtcatttt taaaaatacc taaagtgcca gaccggaacc tatagctact | 3000 |
| gctagaagtc ttaaaaaaac caacagcagc acaggatgta ttaagaatta tatgaagtca | 3060 |
| ggtttgtttt ttttttttt ttttcaaag cacagtactg ttagctgttt ttgtggacag | 3120 |
| gattcgatta agtattccct cttgtcaaac tggaagctag gggaaaaaga gggatttta | 3180 |
| tcctttactc ttctagagta ctgttaatgc cccttccca cagtctttta tataattaaa | 3240 |
| tatatgtcaa tacacattag aatcagattt gaaaaagtta aaacaatttc attgttgtaa | 3300 |
| ttgttcctt tctgttttca tatagtgaat aacctttaaa gggttgtttt gttttgtttt | 3360 |
| gaattatagg agttataatc tttggagatg attgcatatc tcattagata tgcaatataa | 3420 |
| atttatctga gtgaacaaag tgctaaataa atagatctac attttgtaca tatttatata | 3480 |
| aaatttaccct ttaagtattt actttaaaaa atttaatggc ttaactcgaa cttgaagaca | 3540 |
| catacttcaa ctgtccttat tgtccattaa actgataatt ttgattttc ttgcttttat | 3600 |
| agattttact atataggaat caagatttaa gaaattttgc attaaaaata gtgtaccaat | 3660 |
| gcttcatata cgttagttat ttgctattat gtagggaaga ggattgttat ttcaaagata | 3720 |
| tattaaagaa cagttgcatc tgaatataat catgatgcat tcaatgaagt tcatatccat | 3780 |
| gaattcactc ctaatatacc ctaataaagt ggttgaaacc gaaaaaaaaa aaaaaa | 3837 |

<210> SEQ ID NO 2
<211> LENGTH: 367
<212> TYPE: PRT
<213> ORGANISM: Human

<400> SEQUENCE: 2

Met Ala Pro Ser Gly Pro Gly Ser Ser Ala Arg Arg Cys Arg Arg
1               5                   10                  15

Val Leu Tyr Trp Ile Pro Val Val Phe Ile Thr Leu Leu Gly Trp
                20                  25                  30

Ser Tyr Tyr Ala Tyr Ala Ile Gln Leu Cys Ile Val Ser Met Glu Asn
                35                  40                  45

Thr Gly Glu Gln Val Val Cys Leu Met Ala Tyr His Leu Leu Phe Ala
        50                  55                  60

Met Phe Val Trp Ser Tyr Trp Lys Thr Ile Phe Thr Leu Pro Met Asn
65                  70                  75                  80

Pro Ser Lys Glu Phe His Leu Ser Tyr Ala Glu Lys Asp Leu Leu Glu
                85                  90                  95

Arg Glu Pro Arg Gly Glu Ala His Gln Glu Val Leu Arg Arg Ala Ala
                100                 105                 110

```
Lys Asp Leu Pro Ile Tyr Thr Arg Thr Met Ser Gly Ala Ile Arg Tyr
            115                 120                 125

Cys Asp Arg Cys Gln Leu Ile Lys Pro Asp Arg Cys His His Cys Ser
        130                 135                 140

Val Cys Asp Lys Cys Ile Leu Lys Met Asp His His Cys Pro Trp Val
145                 150                 155                 160

Asn Asn Cys Val Gly Phe Ser Asn Tyr Lys Phe Phe Leu Leu Phe Leu
                165                 170                 175

Ala Tyr Ser Leu Leu Tyr Cys Leu Phe Ile Ala Ala Thr Asp Leu Gln
            180                 185                 190

Tyr Phe Ile Lys Phe Trp Thr Asn Gly Leu Pro Asp Thr Gln Ala Lys
        195                 200                 205

Phe His Ile Met Phe Leu Phe Ala Ala Ala Met Phe Ser Val Ser
210                 215                 220

Leu Ser Ser Leu Phe Gly Tyr His Cys Trp Leu Val Ser Lys Asn Lys
225                 230                 235                 240

Ser Thr Leu Glu Ala Phe Arg Ser Pro Val Phe Arg His Gly Thr Asp
                245                 250                 255

Lys Asn Gly Phe Ser Leu Gly Phe Ser Lys Asn Met Arg Gln Val Phe
            260                 265                 270

Gly Asp Glu Lys Lys Tyr Trp Leu Leu Pro Ile Phe Ser Ser Leu Gly
        275                 280                 285

Asp Gly Cys Ser Phe Pro Thr Cys Leu Val Asn Gln Asp Pro Glu Gln
290                 295                 300

Ala Ser Thr Pro Ala Gly Leu Asn Ser Thr Ala Lys Asn Leu Glu Asn
305                 310                 315                 320

His Gln Phe Pro Ala Lys Pro Leu Arg Glu Ser Gln Ser His Leu Leu
                325                 330                 335

Thr Asp Ser Gln Ser Trp Thr Glu Ser Ser Ile Asn Pro Gly Lys Cys
            340                 345                 350

Lys Ala Gly Met Ser Asn Pro Ala Leu Thr Met Glu Asn Glu Thr
        355                 360                 365

<210> SEQ ID NO 3
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 3

Ser Ser Ser Ser Ser Ala Ser Ala Ala Ala Ala Ala Ala Ala
1               5                   10                  15

Ser Ser Ser Ala Ser Cys Ser Arg
            20

<210> SEQ ID NO 4
<211> LENGTH: 522
<212> TYPE: PRT
<213> ORGANISM: Human

<400> SEQUENCE: 4

Met Pro Ser Ala Lys Gln Arg Gly Ser Lys Gly Gly His Gly Ala Ala
1               5                   10                  15

Ser Pro Ser Glu Lys Gly Ala His Pro Ser Gly Gly Ala Asp Asp Val
            20                  25                  30

Ala Lys Lys Pro Pro Pro Ala Ala Ala Phe Ser Gly Trp Cys Val His
```

```
                35                  40                  45
His Val Leu Glu Glu Val Gln Gln Val Arg Arg Ser His Gln Asp Phe
            50                  55                  60
Ser Arg Gln Arg Glu Glu Leu Gly Gln Gly Leu Gln Gly Val Glu Gln
65                  70                  75                  80
Lys Val Gln Ser Leu Gln Ala Thr Phe Gly Thr Phe Glu Ser Ile Leu
                85                  90                  95
Arg Ser Ser Gln His Lys Gln Asp Leu Thr Glu Lys Ala Val Lys Gln
            100                 105                 110
Gly Glu Ser Glu Val Ser Arg Ile Ser Glu Val Leu Gln Lys Leu Gln
        115                 120                 125
Asn Glu Ile Leu Lys Asp Leu Ser Asp Gly Ile His Val Val Lys Asp
    130                 135                 140
Ala Arg Glu Arg Asp Phe Thr Ser Leu Glu Asn Thr Val Glu Glu Arg
145                 150                 155                 160
Leu Thr Glu Leu Thr Lys Ser Ile Asn Asp Asn Ile Ala Ile Phe Thr
                165                 170                 175
Glu Val Gln Lys Arg Ser Gln Lys Glu Ile Asn Asp Met Lys Ala Lys
            180                 185                 190
Val Ala Ser Leu Glu Glu Ser Glu Gly Asn Lys Gln Asp Leu Lys Ala
        195                 200                 205
Leu Lys Glu Ala Val Lys Glu Ile Gln Thr Ser Ala Lys Ser Arg Glu
    210                 215                 220
Trp Asp Met Glu Ala Leu Arg Ser Thr Leu Gln Thr Met Glu Ser Asp
225                 230                 235                 240
Ile Tyr Thr Glu Val Arg Glu Leu Val Ser Leu Lys Gln Glu Gln Gln
                245                 250                 255
Ala Phe Lys Glu Ala Ala Asp Thr Glu Arg Leu Ala Leu Gln Ala Leu
            260                 265                 270
Thr Glu Lys Leu Leu Arg Ser Glu Glu Pro Val Ser Arg Leu Pro Glu
        275                 280                 285
Glu Ile Arg Arg Leu Glu Glu Glu Leu Arg Gln Leu Lys Ser Asp Ser
    290                 295                 300
His Gly Pro Lys Glu Asp Gly Gly Phe Arg His Ser Glu Ala Phe Glu
305                 310                 315                 320
Ala Leu Gln Gln Lys Ser Gln Gly Leu Asp Ser Arg Leu Gln His Val
                325                 330                 335
Glu Asp Gly Val Leu Ser Met Gln Val Ala Ser Ala Arg Gln Thr Glu
            340                 345                 350
Ser Leu Glu Ser Leu Leu Ser Lys Ser Gln Glu His Glu Gln Arg Leu
        355                 360                 365
Ala Ala Leu Gln Gly Arg Leu Glu Gly Leu Gly Ser Ser Glu Ala Asp
    370                 375                 380
Gln Asp Gly Leu Ala Ser Thr Val Arg Ser Leu Gly Glu Thr Gln Leu
385                 390                 395                 400
Val Leu Tyr Gly Asp Val Glu Glu Leu Lys Arg Ser Val Gly Glu Leu
                405                 410                 415
Pro Ser Thr Val Glu Ser Leu Gln Lys Val Gln Glu Gln Val His Thr
            420                 425                 430
Leu Leu Ser Gln Asp Gln Ala Gln Ala Ala Arg Leu Pro Pro Gln Asp
        435                 440                 445
Phe Leu Asp Arg Leu Ser Ser Leu Asp Asn Leu Lys Ala Ser Val Ser
    450                 455                 460
```

```
Gln Val Glu Ala Asp Leu Lys Met Leu Arg Thr Ala Val Asp Ser Leu
465                 470                 475                 480

Val Ala Tyr Ser Val Lys Ile Glu Thr Asn Glu Asn Asn Leu Glu Ser
                485                 490                 495

Ala Lys Gly Leu Leu Asp Asp Leu Arg Asn Asp Leu Ser Arg Leu Phe
            500                 505                 510

Val Lys Val Glu Lys Ile His Glu Lys Val
            515                 520

<210> SEQ ID NO 5
<211> LENGTH: 2231
<212> TYPE: DNA
<213> ORGANISM: Human

<400> SEQUENCE: 5
```

| | | | | | |
|---|---|---|---|---|---|
| agccaatggg | gctcgctcgc | ctcccagccc | gcggcccgag | ccgccgccgc | gcccgccatg | 60 |
| ccctcggcca | acaaaggggg | ctccaagggc | ggccacggcg | ccgcgagccc | ctcggagaag | 120 |
| ggtgcccacc | cgtcgggcgg | cgcggatgac | gtggcgaaga | agccgccgcc | ggcgccgcag | 180 |
| cagccgccgc | cgccgcccgc | gccgcacccg | cagcagcacc | cgcagcagca | cccgcagaac | 240 |
| caggcgcacg | gcaagggcgg | ccaccgcggc | ggcggcggcg | gcggcggcaa | gtcctcctcc | 300 |
| tcctcctccg | cctccgccgc | cgctgccgcc | gccgccgcct | cgtcctcggc | gtcctgctcg | 360 |
| cgcaggctcg | gcagggcgct | caactttctc | ttctacctcg | ccctggtggc | ggcggccgct | 420 |
| ttctcgggct | ggtgcgtcca | ccacgtcctg | gaggaggtcc | agcaggtccg | cgcagccac  | 480 |
| caggacttct | cccggcagag | ggaggagctg | gccagggct  | tgcagggcgt | cgagcagaag | 540 |
| gtgcagtctt | tgcaagccac | atttggaact | tttgagtcca | tcttgagaag | ctcccaacat | 600 |
| aaacaagacc | tcacagagaa | agctgtgaag | caaggggaga | gtgaggtcag | ccggatcagc | 660 |
| gaagtgctgc | agaaactcca | gaatgagatt | ctcaaagacc | tctcggatgg | gatccatgtg | 720 |
| gtgaaggacg | cccgggagcg | ggacttcacg | tccctggaga | cacggtggga | ggagcggctg | 780 |
| acggagctca | ccaaatccat | caacgacaac | atcgccatct | tcacagaagt | ccagaagagg | 840 |
| agccagaagg | agatcaatga | catgaaggca | aaggttgcct | ccctggaaga | atctgagggg | 900 |
| aacaagcagg | atttgaaagc | cttaaaggaa | gctgtgaagg | agatacagac | ctcagccaag | 960 |
| tccagagagt | gggacatgga | ggccctgaga | agtacccttc | agactatgga | gtctgacatc | 1020 |
| tacaccgagg | tccgcgagct | ggtgagcctc | aagcaggagc | agcaggcttt | caaggaggcg | 1080 |
| gccgacacgg | agcggctcgc | cctgcaggcc | tcacgagaa  | agcttctcag | gtctgaggag | 1140 |
| tccgtctccc | gcctccggga | ggagatccgg | agactggagg | aagagctccg | ccagctgaag | 1200 |
| tccgattccc | acgggccgaa | ggaggacgga | ggcttcagac | actcggaagc | ctttgaggca | 1260 |
| ctccagcaaa | agagtcaggg | actggactcc | aggctccagc | acgtggagga | tggggtgctc | 1320 |
| tccatgcagg | tggcttctgc | gcgccagacc | gagagcctgg | agtccctcct | gtccaagagc | 1380 |
| caggagcacg | agcagcgcct | ggccgccctg | caggggcgcc | tggaaggcct | cgggtcctca | 1440 |
| gaggcagacc | aggatggcct | ggccagcacg | gtgaggagcc | tggcgagac  | ccagctggtg | 1500 |
| ctctacggtg | acgtggagga | gctgaagagg | agtgtgggcg | agctccccag | caccgtggaa | 1560 |
| tcactccaga | aggtgcagga | gcaggtgcac | acgctgctca | gtcaggacca | agcccaggcc | 1620 |
| gcccgtctgc | ctcctcagga | cttcctggac | agactttctt | ctctagacaa | cctgaaagcc | 1680 |
| tcagtcagcc | aagtggaggc | ggacttgaaa | atgctcagga | ctgctgtgga | cagtttggtt | 1740 |
| gcatactcgg | tcaaaataga | aaccaacgag | aacaatctgg | aatcagccaa | gggtttacta | 1800 |

```
gatgacctga ggaatgatct ggataggttg tttgtgaaag tggagaagat tcacgaaaag   1860
gtctaaatga attgcgtgtg cagggcgcgg atttaaagtc caatttctca tgaccaaaaa   1920
atgtgtggtt ttttcccatg tgtcccctac cccccaattt cttgtcccct cttaaagagc   1980
agttgtcacc acctgaacac caaggcattg tatttcatg cccagttaac ttatttacaa    2040
tatttaagtt ctctgcttct gcatttggtt ggtttcctga agcgcagccc ctgtgaataa   2100
caggtggctt tcatggatg tctctagtca gagaaaaatg ataaaggctt aaattgagga    2160
ttaacagaag cagattaacc tcagaaatcc tgtctggctg gcagatttca agtaaaaaaa   2220 aaaaaaaaa a                                                          2231
```

<210> SEQ ID NO 6
<211> LENGTH: 9
<212> TYPE: PRT
<213> ORGANISM: Artificial Sequence
<220> FEATURE:
<223> OTHER INFORMATION: Synthetic Peptides

<400> SEQUENCE: 6

Thr Val Pro Ala Ala Val Val Val Ala
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Peptides

<400> SEQUENCE: 7

Ser Val Pro Ala Ala Val Val Val Ala
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptides

<400> SEQUENCE: 8

Thr Val Pro Ala Ala Val Val Leu Ala
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic Peptides

<400> SEQUENCE: 9

Ser Leu Pro Ala Ala Val Val Val Ala
1               5

<210> SEQ ID NO 10
<211> LENGTH: 485
<212> TYPE: PRT
<213> ORGANISM: Human

<400> SEQUENCE: 10

Met Tyr Lys Met Asn Ile Cys Asn Lys Pro Ser Asn Lys Thr Ala Pro
1               5                   10                  15

Glu Lys Ser Val Trp Thr Ala Pro Ala Gln Pro Ser Gly Pro Ser Pro

```
                        20                  25                  30
Glu Leu Gln Gly Gln Arg Ser Arg Arg Asn Gly Trp Ser Trp Pro Pro
                35                  40                  45

His Pro Leu Gln Ile Val Ala Trp Leu Leu Tyr Leu Phe Phe Ala Val
        50                  55                  60

Ile Gly Phe Gly Ile Leu Val Pro Leu Leu Pro His His Trp Val Pro
65                  70                  75                  80

Ala Gly Tyr Ala Cys Met Gly Ala Ile Phe Ala Gly His Leu Val Val
                85                  90                  95

His Leu Thr Ala Val Ser Ile Asp Pro Ala Asp Ala Asn Val Arg Asp
        100                 105                 110

Lys Ser Tyr Ala Gly Pro Leu Pro Ile Phe Asn Arg Ser Gln His Ala
                115                 120                 125

His Val Ile Glu Asp Leu His Cys Asn Leu Cys Asn Val Asp Val Ser
        130                 135                 140

Ala Arg Ser Lys His Cys Ser Ala Cys Asn Lys Cys Val Cys Gly Phe
145                 150                 155                 160

Asp His His Cys Lys Trp Leu Asn Asn Cys Val Gly Glu Arg Asn Tyr
                165                 170                 175

Arg Leu Phe Leu His Ser Val Ala Ser Ala Leu Leu Gly Val Leu Leu
        180                 185                 190

Leu Val Leu Val Ala Thr Tyr Val Phe Val Glu Phe Val Asn Pro
        195                 200                 205

Met Arg Leu Arg Thr Asn Arg His Phe Glu Val Leu Lys Asn His Thr
        210                 215                 220

Asp Val Trp Phe Val Phe Leu Pro Ala Ala Pro Val Glu Thr Gln Ala
225                 230                 235                 240

Pro Ala Ile Leu Ala Leu Ala Ala Leu Leu Ile Leu Gly Leu Leu
                245                 250                 255

Ser Thr Ala Leu Leu Gly His Leu Leu Cys Phe His Ile Tyr Leu Met
        260                 265                 270

Trp His Lys Leu Thr Thr Tyr Glu Tyr Ile Val Gln His Arg Pro Pro
        275                 280                 285

Gln Glu Ala Lys Gly Val His Arg Glu Leu Glu Ser Cys Pro Pro Lys
        290                 295                 300

Met Arg Pro Ile Gln Glu Met Glu Phe Tyr Met Arg Thr Phe Arg His
305                 310                 315                 320

Met Arg Pro Glu Pro Pro Gly Gln Ala Gly Pro Ala Ala Val Asn Ala
                325                 330                 335

Lys His Ser Arg Pro Ala Ser Pro Asp Pro Thr Pro Gly Arg Arg Asp
        340                 345                 350

Cys Ala Gly Pro Pro Val Gln Val Glu Trp Asp Arg Lys Lys Pro Leu
                355                 360                 365

Pro Trp Arg Ser Pro Leu Leu Leu Ala Met Trp Gly Pro Gln Ala
        370                 375                 380

Pro Pro Cys Leu Cys Arg Lys Arg Gly Arg Gly Ala Cys Ile Lys Cys
385                 390                 395                 400

Glu Arg Leu Arg Pro Arg Ile Arg Arg Gly Leu Gly Pro Ala
                405                 410                 415

Ala Ala Pro Ala Arg Arg Ile Pro Arg Thr Pro Ala Leu Cys Thr
                420                 425                 430

Pro Leu Ala Leu Pro Ala Pro Thr Arg Arg Arg Gln Ser Pro Trp
                435                 440                 445
```

```
  Thr Arg Phe Gln Trp Arg Arg Arg Ala Trp Ala Ala Pro Leu Trp Pro
  450                 455                 460
  Pro Arg Gly Ala Gly Ala Asp Ser Pro Arg Trp Arg Gly Arg Arg Val
  465                 470                 475                 480
  Arg Pro Pro Phe Ser
                  485

<210> SEQ ID NO 11
<211> LENGTH: 2049
<212> TYPE: DNA
<213> ORGANISM: Human

<400> SEQUENCE: 11
gccggacgag gcccagccag tctgggtctg gcctggccgc ccctccagcc tgctggagcc     60
ggagccggag ccggagccgg agccagagcc agagctcgag gactcaccgg cccagtctcc    120
gtccgggatg gggcccccgct cccgggcgcg ttgccgccca gtcccgggga ccgtccctac    180
cgcgagggtc tgaggcgcgg ctgccccggg gagggtggaa ggcaggcgt ggggcccgaa     240 cctctggctg actttggcag ggcccatctg gcacggcctc cgcggcgcgc agctgttttc    300
aagtcagcaa acatttactg aggatctact atgtacaaga tgaacatctg caacaagccc    360
tccaacaaga cggcccctga agagtgtgtg tggacggcac cggcacagcc cagcggaccc    420
tcccctgagc tgcagggcca cgatcccgc cggaatgggt ggagctggcc cctcacccg     480 ctccagattg tggcctggct gctgtacctc ttctttgctg tgatcggctt tgggatcctt    540
gttcccctcc tgcctcacca ctgggtgccc gctggctacg cttgcatggg cgccatcttt    600
gctggccacc ttgtggtgca cctgaccgcc gtctccatcg atccagcaga tgccaacgtg    660
cgggacaaga gctatgcggg gcccctgccc atcttcaacc gaagccagca cgcacatgtc    720
attgaagacc tgcactgcaa cttgtgcaac gtggatgtga gcgctcgctc caagcactgc    780
agcgcctgca acaagtgcgt gtgcggtttc gaccaccact gcaagtggct caacaactgt    840
gtgggcgagc ggaactaccg gctctttcta cacagtgttg catccgcttt actgggcgtc    900
ctgctcctgg tgctggtggc cacatatgtc ttcgtggagt ctctttgtcaa ccccatgcgt    960 ctgcgcacca accgacactt tgaagtcctg aagaatcaca cggatgtgtg gttcgtgttc   1020
ctgcctgccg ccccgtgga gacccaggcc cctgccatcc tggccctggc cgccctgctc   1080
atccttctgg gcctcctgtc cacagccctc ctggggcacc tgctctgctt ccacatttat   1140
ctcatgtggc acaagctcac cacctatgag tacatcgtgc agcaccgccc accacaggag   1200 gccaagggg ttcacaggga gctcgagtca tgtcctccca agatgcggcc cattcaggag   1260
atggagttct acatgcggac cttcagacat atgcgcccag agcccctgg ccaggccggg   1320 ccagcagcag tgaatgccaa acactctcgc cctgcctccc cggatccgac cccaggtagg   1380
agggactgtg ctgggcctcc ggtccaggtg gagtgggata gaaagaagcc tctaccctgg   1440
cgctcgcctc tgcttctttt ggcgatgtgg ggccctcagg ctccccgtg tctctgcaga   1500 aaaagaggaa gaggcgcgtg tataaagtgc gaacgtctga gacctcggat ccggcgtcgg   1560
ggcctagggc cccagccgc cgctccagct cgtcgacgga ttccgcggac gccagccctg   1620
tgcacgccgc tggccctgcc ggcgcctacc actcggcgtc ggcagagtcc gtggacgaga   1680
ttccagtggc gcagacgcgc ctgggcagcg ccgctctggc cgccccgcgg ggccggggcc   1740
gacagcccac gctggcgcgg caggcgcgtg cgcccgccgt tttcgtgagc ccgagcagcg   1800
gcgagcccag ggcgccgggc ggcgggagg ctggtctggc ttagctgggc cgagaggccg   1860
gagggccgag ttagagcggc cggcctgact ctctatgcaa caccccatcc ttgccgcacc   1920
```

-continued

```
gagtgcactt tagggggcccc tacggccggc gggatcggcc tccctccccc acgactcagc    1980
aataccggcc ccaccggctg tgatgctcca ataaactttt ttatgcttta aaaaaaaaaa    2040
aaaaaaaaa                                                              2049
```

<210> SEQ ID NO 12
<211> LENGTH: 327
<212> TYPE: PRT
<213> ORGANISM: Human

<400> SEQUENCE: 12

```
Met Met Leu Ile Pro Thr His His Phe Arg Asn Ile Glu Arg Lys Pro
1               5                   10                  15

Glu Tyr Leu Gln Pro Glu Lys Cys Val Pro Pro Tyr Pro Gly Pro
            20                  25                  30

Val Gly Thr Met Trp Phe Ile Arg Asp Gly Cys Gly Ile Ala Cys Ala
        35                  40                  45

Ile Val Thr Trp Phe Leu Val Leu Tyr Ala Glu Phe Val Val Leu Phe
    50                  55                  60

Val Met Leu Ile Pro Ser Arg Asp Tyr Val Tyr Ser Ile Ile Asn Gly
65                  70                  75                  80

Ile Val Phe Asn Leu Leu Ala Phe Leu Ala Leu Ala Ser His Cys Arg
                85                  90                  95

Ala Met Leu Thr Asp Pro Gly Ala Val Pro Lys Gly Asn Ala Thr Lys
            100                 105                 110

Glu Phe Ile Glu Ser Leu Gln Leu Lys Pro Gly Gln Val Val Tyr Lys
        115                 120                 125

Cys Pro Lys Cys Cys Ser Ile Lys Pro Asp Arg Ala His His Cys Ser
    130                 135                 140

Val Cys Lys Arg Cys Ile Arg Lys Met Asp His His Cys Pro Trp Val
145                 150                 155                 160

Asn Asn Cys Val Gly Glu Asn Asn Gln Lys Tyr Phe Val Leu Phe Thr
                165                 170                 175

Met Tyr Ile Ala Leu Ile Ser Leu His Ala Leu Ile Met Val Gly Phe
            180                 185                 190

His Phe Leu His Cys Phe Glu Glu Asp Trp Thr Thr Tyr Gly Leu Asn
        195                 200                 205

Arg Glu Glu Met Ala Glu Thr Gly Ile Ser Leu His Glu Lys Met Gln
    210                 215                 220

Pro Leu Asn Phe Ser Ser Thr Glu Cys Ser Phe Ser Pro Pro Thr
225                 230                 235                 240

Thr Val Ile Leu Leu Ile Leu Leu Cys Phe Glu Gly Leu Leu Phe Leu
                245                 250                 255

Ile Phe Thr Ser Val Met Phe Gly Thr Gln Val His Ser Ile Cys Thr
            260                 265                 270

Asp Glu Thr Gly Ile Glu Gln Leu Lys Lys Glu Glu Arg Arg Trp Ala
        275                 280                 285

Lys Lys Thr Lys Trp Met Asn Met Lys Ala Val Phe Gly His Pro Phe
    290                 295                 300

Ser Leu Gly Trp Ala Ser Pro Phe Ala Thr Pro Asp Gln Gly Lys Ala
305                 310                 315                 320

Asp Pro Tyr Gln Tyr Val Val
                325
```

<210> SEQ ID NO 13

<211> LENGTH: 2720
<212> TYPE: DNA
<213> ORGANISM: Human

<400> SEQUENCE: 13

```
gctcgatggg cttctcctgc gcgccgcccg gtgtctggcc gagtccagag agccgcggcg      60
cctcgttccg aggagccatc gccgaagccc gaggccgggt cccggggttgg ggactgcagg    120
ggaaggcagc ggcggcggcg gcgggagccc caccggggtc tgggactggg gaactgcctc    180
cggcttcacg atgccagtat ggacagaata gcttatgatg cttatcccca cccaccactt    240
ccgaaacatt gagcggaaac cagaatacct ccagccagag aagtgtgtcc caccccccta    300
ccctggtcct gtgggaacca tgtggtttat ccgtgacggc tgtggcatcg cctgtgccat    360
cgttacctgg tttctggtcc tctatgcgga gttcgtggtc ctctttgtca tgctgattcc    420
atctcgagac tacgtgtata gcatcatcaa cggaattgtg ttcaacctgc tggccttctt    480
ggccctggcc tcccactgcc gggccatgct gacggacccc ggggcagtgc ccaaaggaaa    540
tgccactaaa gaattcatcg agagtttaca gttgaagcct gggcaggtgg tgtacaagtg    600
ccccaaaatgc tgcagcatca gcccgaccg agcccaccac tgcagtgttt gtaagcggtg    660
cattcggaag atggaccacc actgtccctg gtcaacaac tgtgtaggcg agaacaacca    720
gaagtacttc gtcctgtttta caatgtacat agctctcatt ccttgcacg ccctcatcat    780
ggtgggattc cacttcctgc attgctttga agaagattgg acaacctatg gactgaacag    840
ggaagaaatg gcagagactg gaatctctct tcatgaaaaa atgcagcccc ttaacttcag    900
ttcgacagag tgcagctcct tctctccacc caccacagtg attctcctta tcctgctgtg    960
ctttgagggc ctgctcttcc tcattttcac atcagtgatg tttgggaccc aggtgcactc   1020
catctgcaca gatgagacgg gaatagaaca attgaaaaag gaagagagaa gatgggctaa   1080
aaaaacaaag tggatgaaca tgaaagccgt ttttggccac cccttctctc taggctgggc   1140
cagccccttt gccacgccag accaagggaa ggcagacccg taccagtatg tggtctgaag   1200
gaccccgacc ggcatggcca ctcagacaca agtccacacc acagcactac cgtcccatcc   1260
gttctcatga atgtttaaat cgaaaaagca aaacaactac tcttaaaact ttttttatgt   1320
ctcaagtaaa atggctgagc attgcagaga aaaaaaaaag tccccacatt ttatttttta   1380
aaaccatcc tttcgatttc ttttggtgac cgaagctgct ctcttttcct tttaaaatca   1440
cttctctggc ctctggtttc tctctgctgt ctgtctggca tgactaatgt agagggcgct   1500
gtctcgcgct gtgccattc tactaactga gtgagacatg acgctgtgcg tggatggaat   1560
agtctggaca cctggtgggg gatgcatggg aaagccagga gggccctgac ctcccactgc   1620
ccaggaggca gtggcgggct ccccgatggg acataaaacc tcaccgaaga tggatgctta   1680
ccccttgagg cctgagaagg gcaggatcag aagggacctt ggcacagcga cctcatcccc   1740
caagtgaca cggtttgcct gctaactcgc aaagcaattg cctgccttgt actttatggg   1800
cttggggtgt gtagaatgat tttgcggggg agtggggaga aagatgaaag aggtcttatt   1860
tgtattctga atcagcaatt atattccctg tgattatttg gaagagtgtg taggaaagac   1920
gttttttccag ttcaaaatgc cttatacaat caagaggaaa aaaaattaca caatttcagg   1980
caagctacg tttcctttgt ttcatctgct tcctctctca ccaccccatc tccctctctt   2040
ccccagcaag atgtcaatta agcagtgtga attctgactg caataggcac cagtgcccaa   2100
cacatacagc cccaccatca tccccttctc attttataaa cctcaaagtg gattcacttt   2160
ctgatagtta accccccataa atgtgcacgt acctgtgtct tatctatatt ttaacctggg   2220
```

```
agactgttgt cctggcatgg agatgaccat gatgctgggg ttacctcaca gtccccaccc    2280
tttcaaagtt gacatatggc catcccattg ccagaatcc acagacacac ctaagcctgt     2340
ggcactggga cagaatagat tttccatttg agaggcactt cctgtgtcag tcttgtttga    2400
aggaggtggt gatggtggat agaggtgaag gaggtaggga gtgccctcca agtgcaaaaa    2460
taacaaatat gattattgac catcgggaa ttctcacaca ttgatttgtt ttttaagcaa     2520
ttgccagaaa ccccctttt tagcttttgc ttggggtggg ggtaggagtt aaggtttatt     2580
caatcctgtc ctgggtaggg cgaaagttaa tctagccatg tgattttca gaaaagtaag    2640 tggaacatgc tgccactttt caattctgtc agtgcttcca catggaaaca aaatgcaata    2700 aaattttcc aaaacctgat                                                2720
```

<210> SEQ ID NO 14
<211> LENGTH: 344
<212> TYPE: PRT
<213> ORGANISM: Human

<400> SEQUENCE: 14

```
Met Asp Phe Leu Val Leu Phe Leu Phe Tyr Leu Ala Ser Val Leu Met
1               5                   10                  15

Gly Leu Val Leu Ile Cys Val Cys Ser Lys Thr His Ser Leu Lys Gly
            20                  25                  30

Leu Ala Arg Gly Gly Ala Gln Ile Phe Ser Cys Ile Ile Pro Glu Cys
        35                  40                  45

Leu Gln Arg Ala Val His Gly Leu Leu His Tyr Leu Phe His Thr Arg
    50                  55                  60

Asn His Thr Phe Ile Val Leu His Leu Val Leu Gln Gly Met Val Tyr
65                  70                  75                  80

Thr Glu Tyr Thr Trp Glu Val Phe Gly Tyr Cys Gln Glu Leu Glu Leu
                85                  90                  95

Ser Leu His Tyr Leu Leu Leu Pro Tyr Leu Leu Leu Gly Val Asn Leu
            100                 105                 110

Phe Phe Phe Thr Leu Thr Cys Gly Thr Asn Pro Gly Ile Ile Thr Lys
        115                 120                 125

Ala Asn Glu Leu Leu Phe Leu His Val Tyr Glu Phe Asp Glu Val Met
    130                 135                 140

Phe Pro Lys Asn Val Arg Cys Ser Thr Cys Asp Leu Arg Lys Pro Ala
145                 150                 155                 160

Arg Ser Lys His Cys Ser Val Cys Asn Trp Cys Val His Arg Phe Asp
                165                 170                 175

His His Cys Val Trp Val Asn Asn Cys Ile Gly Ala Trp Asn Ile Arg
            180                 185                 190

Tyr Phe Leu Ile Tyr Val Leu Thr Leu Thr Ala Ser Ala Ala Thr Val
        195                 200                 205

Ala Ile Val Ser Thr Thr Phe Leu Val His Leu Val Met Ser Asp
    210                 215                 220

Leu Tyr Gln Glu Thr Tyr Ile Asp Asp Leu Gly His Leu His Val Met
225                 230                 235                 240

Asp Thr Val Phe Leu Ile Gln Tyr Leu Phe Leu Thr Phe Pro Arg Ile
                245                 250                 255

Val Phe Met Leu Gly Phe Val Val Leu Ser Phe Leu Leu Gly Gly
            260                 265                 270

Tyr Leu Leu Phe Val Leu Tyr Leu Ala Ala Thr Asn Gln Thr Thr Asn
        275                 280                 285
```

```
Glu Trp Tyr Arg Gly Asp Trp Ala Trp Cys Gln Arg Cys Pro Leu Val
        290                 295                 300

Ala Trp Pro Pro Ser Ala Glu Pro Gln Val His Arg Asn Ile His Ser
305                 310                 315                 320

His Gly Leu Arg Ser Asn Leu Gln Glu Ile Phe Leu Pro Ala Phe Pro
                325                 330                 335

Cys His Glu Arg Lys Lys Gln Glu
                340

<210> SEQ ID NO 15
<211> LENGTH: 1704
<212> TYPE: DNA
<213> ORGANISM: Human

<400> SEQUENCE: 15
gcatttgact gcaactcttg tcgtcttatg tgggtgttga attgatctgt ctctgcaggc      60
cagatccagg ctcctggaag aaccatgtcc ggcagctact ggtcatgcca ggcacacact     120
gctgcccaag aggagctgct gtttgaatta tctgtgaatg ttgggaagag gaatgccaga     180
gctgccggct gaaaattacc caaccaagag aaatctgcag gatggacttt ctggtcctct     240
tcttgttcta cctggcttcg gtgctgatgg gtcttgttct tatctgcgtc tgctcgaaaa     300
cccatagctt gaaaggcctg gcaaggggag gagcacagat attttcctgt ataattccag     360
aatgtcttca gagagccgtg catggattgc ttcattacct ttttccatacg agaaaccaca     420
ccttcattgt cctgcacctg gtcttgcaag ggatggttta tactgagtac acctgggaag     480
tatttggcta ctgtcaggag ctggagttgt ccttgcatta ccttcttctg ccctatctgc     540
tgctaggtgt aaacctgttt tttttcaccc tgacttgtgg aaccaatcct ggcattataa     600
caaaagcaaa tgaattatta tttcttcatg tttatgaatt tgatgaagtg atgtttccaa     660
agaacgtgag gtgctctact tgtgatttaa ggaaaccagc tcgatccaag cactgcagtg     720
tgtgtaactg gtgtgtgcac cgtttcgacc atcactgtgt ttgggtgaac aactgcatcg     780
gggcctggaa catcaggtac ttcctcatct acgtcttgac cttgacggcc tcggctgcca     840
ccgtcgccat tgtgagcacc acttttctgg tccacttggt ggtgatgtca gatttatacc     900
aggagactta catcgatgac cttggacacc tccatgttat ggacacggtc tttcttattc     960
agtacctgtt cctgactttt ccacggattg tcttcatgct gggcttttgtc gtggttctga    1020
gcttcctcct gggtggctac ctgttgtttg tcctgtatct ggcggccacc aaccagacta    1080
ctaacgagtg gtacagaggt gactgggcct ggtgccagcg ttgtcccctt gtggcctggc    1140
ctccgtcagc agagccccaa gtccaccgga acattcactc ccatgggctt cggagcaacc    1200
ttcaagagat ctttctacct gcctttccat gtcatgagag aagaaacaa gaatgacaag    1260
tgtatgactg cctttgagct gtagttcccg tttatttaca catgtggatc ctcgtttcc    1320
aagcaaaaaa aaatggcttg tttgttttga tttctgctgt gcttataaat cactttcggt    1380
gggcaaggga gagaggggaa aatgggtgtt gactgaggaa tcccccttgc ttgtcttctt    1440
ttgaaaccgg gcatctctga agtcctggtg tcaaggggat caagagatga cttctcagag    1500
gttctaggtg atgctgagac cttggtgtct ctaaactctg gcatgtggaa caggagggc    1560
ttgcggccgt gtctctgacc tgtgtgatgt gcaggagggt ctcattgact cagcgcctgc    1620
gcgttagtgc ctggctgtgc tctcttttat gcccctcta ttctcctctc tccccagggg    1680
gattttcatc tcaacaacag agtg                                          1704

<210> SEQ ID NO 16
```

-continued

```
<211> LENGTH: 715
<212> TYPE: PRT
<213> ORGANISM: Human

<400> SEQUENCE: 16

Met Pro Ala Glu Ser Gly Lys Arg Phe Lys Pro Ser Lys Tyr Val Pro
1               5                   10                  15

Val Ser Ala Ala Ala Ile Phe Leu Val Gly Ala Thr Thr Leu Phe Phe
            20                  25                  30

Ala Phe Thr Cys Pro Gly Leu Ser Leu Tyr Val Ser Pro Ala Val Pro
        35                  40                  45

Ile Tyr Asn Ala Ile Met Phe Leu Phe Val Leu Ala Asn Phe Ser Met
50                  55                  60

Ala Thr Phe Met Asp Pro Gly Ile Phe Pro Arg Ala Glu Glu Asp Glu
65                  70                  75                  80

Asp Lys Glu Asp Asp Phe Arg Ala Pro Leu Tyr Lys Thr Val Glu Ile
                85                  90                  95

Lys Gly Ile Gln Val Arg Met Lys Trp Cys Ala Thr Cys Arg Phe Tyr
            100                 105                 110

Arg Pro Pro Arg Cys Ser His Cys Ser Val Cys Asp Asn Cys Val Glu
        115                 120                 125

Glu Phe Asp His His Cys Pro Trp Val Asn Asn Cys Ile Gly Arg Arg
130                 135                 140

Asn Tyr Arg Tyr Phe Phe Leu Phe Leu Leu Ser Leu Thr Ala His Ile
145                 150                 155                 160

Met Gly Val Phe Gly Phe Gly Leu Leu Tyr Val Leu Tyr His Ile Glu
                165                 170                 175

Glu Leu Ser Gly Val Arg Thr Ala Val Thr Met Ala Val Met Cys Val
            180                 185                 190

Ala Gly Leu Phe Phe Ile Pro Val Ala Gly Leu Thr Gly Phe His Val
        195                 200                 205

Val Leu Val Ala Arg Gly Arg Thr Thr Asn Glu Gln Val Thr Gly Lys
210                 215                 220

Phe Arg Gly Gly Val Asn Pro Phe Thr Asn Gly Cys Cys Asn Asn Val
225                 230                 235                 240

Ser Arg Val Leu Cys Ser Ser Pro Ala Pro Arg Tyr Leu Gly Arg Pro
                245                 250                 255

Lys Lys Glu Lys Thr Ile Val Ile Arg Pro Pro Phe Leu Arg Pro Glu
            260                 265                 270

Val Ser Asp Gly Gln Ile Thr Val Lys Ile Met Asp Asn Gly Ile Gln
        275                 280                 285

Gly Glu Leu Arg Arg Thr Lys Ser Lys Gly Ser Leu Glu Ile Thr Glu
290                 295                 300

Ser Gln Ser Ala Asp Ala Glu Pro Pro Pro Pro Lys Pro Asp Leu
305                 310                 315                 320

Ser Arg Tyr Thr Gly Leu Arg Thr His Leu Gly Leu Ala Thr Asn Glu
                325                 330                 335

Asp Ser Ser Leu Leu Ala Lys Asp Ser Pro Pro Thr Pro Thr Met Tyr
            340                 345                 350

Lys Tyr Arg Pro Gly Tyr Ser Ser Ser Thr Ser Ala Ala Met Pro
        355                 360                 365

His Ser Ser Ala Lys Leu Ser Arg Gly Asp Ser Leu Lys Glu Pro
370                 375                 380

Thr Ser Ile Ala Glu Ser Ser Arg His Pro Ser Tyr Arg Ser Glu Pro
385                 390                 395                 400
```

Ser Leu Glu Pro Glu Ser Phe Arg Ser Pro Thr Phe Gly Lys Ser Phe
            405                 410                 415

His Phe Asp Pro Leu Ser Ser Gly Ser Arg Ser Ser Leu Lys Ser
        420                 425                 430

Ala Gln Gly Thr Gly Phe Glu Leu Gly Gln Leu Gln Ser Ile Arg Ser
        435                 440                 445

Glu Gly Thr Thr Ser Thr Ser Tyr Lys Ser Leu Ala Asn Gln Thr Arg
450                 455                 460

Asn Gly Ser Leu Ser Tyr Asp Ser Leu Leu Thr Pro Ser Asp Ser Pro
465                 470                 475                 480

Asp Phe Glu Ser Val Gln Ala Gly Pro Glu Pro Asp Pro Pro Leu Gly
                485                 490                 495

Tyr Thr Ser Pro Phe Leu Ser Ala Arg Leu Ala Gln Gln Arg Glu Ala
                500                 505                 510

Glu Arg His Pro Arg Leu Val Pro Thr Gly Pro Thr His Arg Glu Pro
            515                 520                 525

Ser Pro Val Arg Tyr Asp Asn Leu Ser Arg His Ile Val Ala Ser Leu
        530                 535                 540

Gln Glu Arg Glu Lys Leu Leu Arg Gln Ser Pro Leu Pro Gly Arg
545                 550                 555                 560

Glu Glu Glu Pro Gly Leu Gly Asp Ser Gly Ile Gln Ser Thr Pro Gly
                565                 570                 575

Ser Gly His Ala Pro Arg Thr Ser Ser Ser Asp Asp Ser Lys Arg
                580                 585                 590

Ser Pro Leu Gly Lys Thr Pro Leu Gly Arg Pro Ala Val Pro Arg Phe
        595                 600                 605

Gly Lys Pro Asp Gly Leu Arg Gly Arg Gly Val Gly Ser Pro Glu Pro
    610                 615                 620

Gly Pro Thr Ala Pro Tyr Leu Gly Arg Ser Met Ser Tyr Ser Ser Gln
625                 630                 635                 640

Lys Ala Gln Pro Gly Val Ser Glu Thr Glu Glu Val Ala Leu Gln Pro
                645                 650                 655

Leu Leu Thr Pro Lys Asp Glu Val Gln Leu Lys Thr Thr Tyr Ser Lys
                660                 665                 670

Ser Asn Gly Gln Pro Lys Ser Leu Gly Ser Ala Ser Pro Gly Pro Gly
            675                 680                 685

Gln Pro Pro Leu Ser Ser Pro Thr Arg Gly Gly Val Lys Lys Val Ser
        690                 695                 700

Gly Val Gly Gly Thr Thr Tyr Glu Ile Ser Val
705                 710                 715

<210> SEQ ID NO 17
<211> LENGTH: 4582
<212> TYPE: DNA
<213> ORGANISM: Human

<400> SEQUENCE: 17
gagacccggc actgagggca acggccgcgc gccggctccg agacgagcga cgcctggcgg      60
gagcgcgcgg cagcggggcg ggcgtggagc gtgcgggggc cgcgcgctgc ttctctgagg     120
caggacggca ctgccgggag gcggcggtga caacgacggc ggtggtgacg ggcaccgggc     180
tcgcgggtga gacacagtaa cctggttgaa ctctgcatct ggaaagctga agactgaaga     240
aagataagag acattgacta gtctggaaac agggacatct ttggaacttc gttttcatcc     300
acagtaaact tttgaagtgt catcaattgg aattgatttc ttcatcttat tctgcctatt     360

```
gggaagaaca tggcttcaag gattttaagt ttcccttttag ttttacatga actttgtagg      420
aaacagagcc cttaaagggc ttgggaataa caagaagaga ttgaagacag agaagcttgc      480
cctgttttcc ttgccccttc aaagaaaagg atttacagct caaacttaga acagctgttg      540
tccagcttta gccatcaaga gagaaataaa ttaaaccacc attgccagac tacaagccct      600
ggtgaagtca gggtgtggga gtggtggcat tgagaagact acctaaaaga gacaaagact      660
gcagtaaaca aagctcctct ttaaagttgg aaggggcctc aggttccttc ttggattgaa      720
atagaaatag aaacacaggg cacacctctt ttaggtgcag ctcacatttt atggaactgt      780
agtcgtggag gtactatagt atctcagaag aattttttctt tgcccaaagt tttttttgcca    840 tacccctgata ttctctcctt cttttgaaga cctgcctcca tccatgagct gtatcttgat    900
ctgtctgact gtccatgttt tccacctgca accatttgca tgtgtacagc ctactgtttg      960
tctccagttt ttaaactgta caagttgtgt ttcttaatct tcccttctgc cttgttctgg     1020
ggaggtggtt attcatcatt tggaatcacc tttccccctc ccatgtgctt tccttcattt     1080
gagatctttt gaccttttggc tttatttggg aggggaagg gtgataaagt tttctgtttc     1140
cctggttttt ttttgtactc ctctctgttg cttccctcct cccattttct tgtctgttct     1200
gccgctgtgt gggcctgggc tatgcggcag ggcagatttc ccatcagagc tccaacatgc     1260
ccgcagagtc tggaaagaga ttcaaaccca gcaagtatgt cccggtctct gcagccgcca     1320
tcttcctagt gggagctacg acactcttct ttgcctttac gtgtccagga ctaagcctgt     1380
atgtgtcacc tgcagtgccc atctacaatg caattatgtt tctctttgtg ttggccaact     1440
tcagcatggc caccttcatg gacccaggga ttttccctcg agctgaggag gatgaggaca     1500
aggaagatga tttccgagct ccccttttaca aaacagtgga gataaaggc atccaggtgc     1560 gcatgaaatg gtgtgccacc tgccgctttt accgtccccc tcgatgttcc cactgcagtg     1620
tctgtgacaa ctgtgtggag gaatttgatc atcactgccc ctgggtgaat aactgtattg     1680
gtcgccggaa ctaccgttat ttttttccttt tcctcctttc cctgacagcc cacattatgg     1740 gtgtgttttgg ctttggcctc ctttatgtcc tctaccacat agaggaactc tcaggggtcc     1800
gcacggctgt cacaatggca gtaatgtgtg tggctggctt attcttcatc cctgtagctg     1860
gcctcacggg atttcacgtg gttctggtgg ccaggggacg cacaaccaat gaacaggtta     1920
cgggtaaatt ccggggaggt gtgaacccct tcaccaatgg ctgctgtaac aatgtcagcc     1980
gtgttctctg cagttctcca gcacccaggt atttggggag accaaagaaa gagaagacaa     2040
ttgtaatcag acctcccttc cttcgaccag aagtttcaga tgggcagata actgtgaaga     2100
tcatggataa tggcatccag ggagagctga ggagaacaaa gtctaaggga agcctggaga     2160
taacagagag ccagtctgca gatgctgaac ctccacctcc tcctaagcca gacctgagcc     2220
gttacacagg gttgcgaaca cacctcggct tggctactaa tgaggatagt agcttattgg     2280
ccaaggacag cccccccgaca cctaccatgt acaagtatcg gccgggttac agtagcagca     2340
gtacgtcagc tgccatgccg cattcctcca gcgccaagtt gagtcgtggg gacagcttga     2400
aggagccaac ctcaattgca gagagcagcc gtcaccccag ctaccgctca gagcccagct     2460
tggaaccaga gagcttccgt tctcctacct ttggcaaaag ttttcacttc gatccactat     2520
ccagtggctc acgctcctcc agcctcaagt cagcccaggg cacaggcttt gagctgggcc     2580
agttgcaatc cattcgttca gagggcacca cctccacctc ctataagagc ctggccaacc     2640
agacacgcaa tggaagccta tcttatgaca gcttgctcac accttcagac agccctgatt     2700
ttgagtcagt gcaggcaggg cctgagccag acccacctttt aggctatacc tctcccttcc     2760
```

```
tgtcagccag gctggcccag caacgggaag ctgagaggca cccacgtttg gtgccaactg    2820
gcccaacaca ccgagagccc tcaccagtcc gttacgacaa tctgtcgcgc cacattgtgg    2880
cctctctcca ggaacgagag aagttgctgc gccagtcacc cccactcccg ggccgtgagg    2940
aagaaccagg cttggggggac tcaggcattc agtcaacacc aggctcgggc catgcccctc   3000
gtactagttc ctcctcagat gattcaaaga gatcaccttt gggcaagact ccactgggac    3060
gcccagctgt ccccgttttt ggcaagccag atgggctaag gggccgggga gtagggtccc    3120
ctgaaccagg cccaacagcc ccatacctgg gccgatcgat gtcttacagc agccaaaaag    3180
cccaacctgg tgtctctgag acagaagaag tggccttgca gccattactg acacccaaag    3240
atgaagtaca gctgaagacc acctacagca aatccaacgg gcagcccaag agcttaggct    3300
cagcctcccc tggcccaggc cagccacctc tcagtagccc cacgagggga ggagtcaaga    3360
aggtgtcagg ggttggtggt accacctatg agatttcggt gtgagccttc ggcacctccc    3420
ctccccaacg cctctgcgcc tacaccaaag gccccaggt ggccaccttc cttccctcaa     3480
ggggctcccc tcccgtgcat ggacattttt taaaccaccg attccaagag gatgaggagt    3540
gttttctaaa atgcagtagg cttggggagt cggagagttg gggccctgag actggggtag    3600 caacccccc tttatctttt taagaccttc ccttccttga tccctggacc agactcagtg     3660
gacatttgtg caattgctcg ccctggaggg aaccagatca ttttttaaacc agaaataatt   3720 tttttatta ttgttacgga ttctattttt ttcctcttct gcgttaccag gtgtgtgtgt     3780
acatataata tatatatata tatattataa atatcaaaga aattatatat ctatcctggg    3840
atgggaaaat gagggaggga tacatatacg gaggggatc ttactcttcc cattcctcag     3900
accagcagga aaagaggga gacgtcagtc ttttcctgt ggttccctct catttgtccc      3960
agttactaac tacggaaata gcatcctctg ctggtgctaa gtgtgattag gaagaagcct    4020
ggggagaggt gagtctggaa ttttggtcac aagagggaag gacttggaga ggagaattag    4080
ttttctaggc tcattggcat ttagtttccc taggaaaggg gtcaaaactt caagacactg    4140
gtggtggtgg gagatcagga aaataacttg gcctagctca aacaatattg gataatcccc    4200
tccttggggg agagggatta gagtgtgctc ctactggccc cttggagcct cccctagctt    4260
acacagttaa cttgatttta aaatccaagg ccaggagaga agaatccaaa aagcaatatt    4320
tttcatcaca tgccaaaaac gggggataga gagaaggagt ggcaggccta ggcccctccg    4380
attgtccctt gggggttacc cctcagccca cctcactatg gtgctgggta gaggggatac    4440
ctgggttcta acctctaaat aggggagatc ccagcctcca caaagaggcc ctttatttt    4500 ttattctgat tagccatttt aaaccaacga ggaataaaaa gaaatcctga tctaaccagc    4560
aaaaaaaaaa aaaaaaaaa aa                                              4582
```

<210> SEQ ID NO 18
<211> LENGTH: 413
<212> TYPE: PRT
<213> ORGANISM: Human

<400> SEQUENCE: 18

Met Gly Thr Phe Cys Ser Val Ile Lys Phe Glu Asn Leu Gln Glu Leu
1               5                   10                  15

Lys Arg Leu Cys His Trp Gly Pro Ile Ile Ala Leu Gly Val Ile Ala
            20                  25                  30

Ile Cys Ser Thr Met Ala Met Ile Asp Ser Val Leu Trp Tyr Trp Pro
        35                  40                  45

```
Leu His Thr Thr Gly Gly Ser Val Asn Phe Ile Met Leu Ile Asn Trp
 50                  55                  60
Thr Val Met Ile Leu Tyr Asn Tyr Phe Asn Ala Met Phe Val Gly Pro
 65                  70                  75                  80
Gly Phe Val Pro Leu Gly Trp Lys Pro Glu Ile Ser Gln Asp Thr Met
                 85                  90                  95
Tyr Leu Gln Tyr Cys Lys Val Cys Gln Ala Tyr Lys Ala Pro Arg Ser
                100                 105                 110
His His Cys Arg Lys Cys Asn Arg Cys Val Met Lys Met Asp His His
                115                 120                 125
Cys Pro Trp Ile Asn Asn Cys Cys Gly Tyr Gln Asn His Ala Ser Phe
            130                 135                 140
Thr Leu Phe Leu Leu Leu Ala Pro Leu Gly Cys Ile His Ala Ala Phe
145                 150                 155                 160
Ile Phe Val Met Thr Met Tyr Thr Gln Leu Tyr His Arg Leu Ser Phe
                165                 170                 175
Gly Trp Asn Thr Val Lys Ile Asp Met Ser Ala Ala Arg Arg Asp Pro
            180                 185                 190
Leu Pro Ile Val Pro Phe Gly Leu Ala Ala Phe Ala Thr Thr Leu Phe
            195                 200                 205
Ala Leu Gly Leu Ala Leu Gly Thr Thr Ile Ala Val Gly Met Leu Phe
210                 215                 220
Phe Ile Gln Met Lys Ile Ile Leu Arg Asn Lys Thr Ser Ile Glu Ser
225                 230                 235                 240
Trp Ile Glu Glu Lys Ala Lys Asp Arg Ile Gln Tyr Tyr Gln Leu Asp
                245                 250                 255
Glu Val Phe Val Phe Pro Tyr Asp Met Gly Ser Arg Trp Arg Asn Phe
                260                 265                 270
Lys Gln Val Phe Thr Trp Ser Gly Val Pro Glu Gly Asp Gly Leu Glu
            275                 280                 285
Trp Pro Val Arg Glu Gly Cys His Gln Tyr Ser Leu Thr Ile Glu Gln
            290                 295                 300
Leu Lys Gln Lys Ala Asp Lys Arg Val Arg Ser Val Arg Tyr Lys Val
305                 310                 315                 320
Ile Glu Asp Tyr Ser Gly Ala Cys Cys Pro Leu Asn Lys Gly Ile Lys
                325                 330                 335
Thr Phe Phe Thr Ser Pro Cys Thr Glu Glu Pro Arg Ile Gln Leu Gln
            340                 345                 350
Lys Gly Glu Phe Ile Leu Ala Thr Arg Gly Leu Arg Tyr Trp Leu Tyr
            355                 360                 365
Gly Asp Lys Ile Leu Asp Asp Ser Phe Ile Glu Gly Val Ser Arg Ile
            370                 375                 380
Arg Gly Trp Phe Pro Arg Lys Cys Val Glu Lys Cys Pro Cys Asp Ala
385                 390                 395                 400
Glu Thr Asp Gln Ala Pro Glu Gly Glu Lys Lys Asn Arg
                405                 410

<210> SEQ ID NO 19
<211> LENGTH: 2187
<212> TYPE: DNA
<213> ORGANISM: Human

<400> SEQUENCE: 19
agagtcctgg cgagggcgct ggccgagagg tgctcggctt gtagcaggtc ccgcactcca      60
gcctctcgct gccagggttt gctctctgct tgtcctgggc tgaggtgtcc atgacggagt     120
```

```
catccaagga ggaaaaaatc tgttccgggt gagcccaggc cgccccggat atgcgatggc    180
tgaggagcag acaccaggga ccacactgag gttgggtttc agaccaagac actggattct    240
cctagttaag ataaagagct ttgggtgcct gacagtgaaa atggtgtaat ctgcgttaac    300
agttcacagc ttgaaggcat gacaattaaa gaacacacat ggacttgtgg cacatggaaa    360
tgtgcgcaca gaaaaggaa atctataatt cttttaaagt aggaaggcat tcttccttgc     420
caaaatgggt acgttctgtt cggttatcaa gtttgaaaat ctacaagaat taaagagact    480
gtgtcactgg ggtcccatca tagcccttgg tgttatagca atatgttcta ccatggccat    540
gattgactct gtgttgtggt attggccctt acatacaact ggaggaagtg tgaatttcat    600
catgttgata aattggactg tcatgattct ttataattac ttcaatgcca tgtttgtcgg    660
tccgggcttt gtccctctgg ggtggaaacc ggaaatttct caggatacca tgtatctcca    720
gtattgtaaa gtctgccaag catacaaggc accacgttca catcactgca gaaagtgtaa    780
cagatgtgtg atgaagatgg accatcactg tccttggatc aacaactgtt gtggttacca    840
aaatcatgct tcgttcacac tgtttctcct tttagcacca ctgggttgta tccatgctgc    900
tttcattttt gtgatgacta tgtacacaca gctttatcat cggctctcct ttgggtggaa    960
cacagtgaag atcgacatga gtgcagcccg gagagatcct cttccaattg ttccatttgg   1020
attagctgca tttgctacca ccttgtttgc cttgggatta gctttaggaa caaccatagc   1080
tgttgggatg ttgttttttta ccagatgaa ataattctc agaaacaaaa cttctattga   1140
gtcatggatt gaagagaagg ctaaagatcg aattcagtat tatcaactag atgaagtctt   1200 tgttttttcca tatgatatgg gaagtagatg gaggaacttt aaacaggtat ttacgtggtc   1260
aggggtccct gaaggagatg gacttgagtg gccagtaaga gaaggctgtc accaatacag   1320
cttaacaata gaacagttga acaaaaagc agataagaga gtcagaagtg ttcgctataa   1380
agtaatagaa gattatagtg gtgcctgctg ccctctgaat aaaggaatca aaaccttctt   1440
cacaagtccc tgcaccgaag agcctcgaat acagctgcaa aaagggaat tcattttagc   1500 cacaagaggt ttacgatact ggttatatgg agacaaaatt cttgatgatt cctttataga   1560
aggtgtttca agaataaggg gttggttccc tagaaaatgt gtggaaaagt gtccctgtga   1620
tgctgaaaca gatcaagccc cagagggga gaagaaaaaa agatagctgc tgttaaaaca   1680
aaattatcct ttaagtctgc ttaattactt gaaaattgta catattacta agaattatg    1740 caatgagcct actctggtta agatgttctt ttcctcaaag gtgccctagt gccatgattt   1800
aaatattttt attaccattt tgaaatggag aagccattct gcatatgcct ttgaattcct   1860
gcccttcttt accacctctt cctcccctc aaaggaaaa catttcatcc aagtaagtta    1920
acggcatttt ctgtaggatt ttcttatgca ctgcacactc tggacctcac ctgcagatac   1980
agttcccccc ttgccaggag catctgcatg tggtacttct ctttcccctc agttgatatt   2040
tcttatatga tattctagat actatagaac tcaatttgtc agattcagta taacctcaga   2100
ttttgttacc tgtcttttaa aaatgcagat tttgtcaaat caaataaaga tcaatggatg   2160
ttgggtataa aaaaaaaaaa aaaaaaa                                        2187

<210> SEQ ID NO 20
<211> LENGTH: 308
<212> TYPE: PRT
<213> ORGANISM: Human

<400> SEQUENCE: 20

Met Gln Pro Ser Gly His Arg Leu Arg Asp Val Glu His His Pro Leu
```

```
              1               5              10              15
Leu Ala Glu Asn Asp Asp Tyr Asp Ser Ser Ser Ser Ser Ser Ser Glu
                20                  25                  30
Ala Asp Val Ala Asp Arg Val Trp Phe Ile Arg Asp Gly Cys Gly Met
                35                  40                  45
Ile Cys Ala Val Met Thr Trp Leu Leu Val Ala Tyr Ala Asp Phe Val
    50                  55                  60
Val Thr Phe Val Met Leu Leu Pro Ser Lys Asp Phe Trp Tyr Ser Val
65                  70                  75                  80
Val Asn Gly Val Ile Phe Asn Cys Leu Ala Val Leu Ala Leu Ser Ser
                85                  90                  95
His Leu Arg Thr Met Leu Thr Asp Pro Gly Ala Val Pro Lys Gly Asn
                100                 105                 110
Ala Thr Lys Glu Tyr Met Glu Ser Leu Gln Leu Lys Pro Gly Glu Val
                115                 120                 125
Ile Tyr Lys Cys Pro Lys Cys Cys Cys Ile Lys Pro Glu Arg Ala His
                130                 135                 140
His Cys Ser Ile Cys Lys Arg Cys Ile Arg Lys Met Asp His His Cys
145                 150                 155                 160
Pro Trp Val Asn Asn Cys Val Gly Glu Lys Asn Gln Arg Phe Phe Val
                165                 170                 175
Leu Phe Thr Met Tyr Ile Ala Leu Ser Ser Val His Ala Leu Ile Leu
                180                 185                 190
Cys Gly Phe Gln Phe Ile Ser Cys Val Arg Gly Gln Trp Thr Glu Cys
                195                 200                 205
Ser Asp Phe Ser Pro Pro Ile Thr Val Ile Leu Leu Ile Phe Leu Cys
                210                 215                 220
Leu Glu Gly Leu Leu Phe Phe Thr Phe Thr Ala Val Met Phe Gly Thr
225                 230                 235                 240
Gln Ile His Ser Ile Cys Asn Asp Glu Thr Gly Ile Glu Arg Leu Lys
                245                 250                 255
Ser Glu Lys Pro Thr Trp Glu Arg Arg Leu Arg Trp Glu Gly Met Lys
                260                 265                 270
Ser Val Phe Gly Gly Pro Pro Ser Leu Leu Trp Met Asn Pro Phe Val
                275                 280                 285
Gly Phe Arg Phe Arg Arg Leu Pro Thr Arg Pro Arg Lys Gly Gly Pro
                290                 295                 300
Glu Phe Ser Val
305

<210> SEQ ID NO 21
<211> LENGTH: 3172
<212> TYPE: DNA
<213> ORGANISM: Human

<400> SEQUENCE: 21
acttccggcg ctcgcaccgc cccgctctcc agccaaggtt ccgggctgag gcatttgctt      60
ggctgcagcc tccttccgac ctgccggcg ggacccaggg gaccaagccg agccgagccg     120
cggggcccgc tccagcccgg ccatgagcgc ggccgcatga tgcgtccctg cctcggccgc     180
tgcagtcgcc gccgccgccg ccgcaggccg ggaggagccg cagcgccggg cgaccccgcc     240
cgggcctcgg atccgatcac ataggacagt atgcacctta agatcctgaa gaaacggcac     300
aaaatgttca gtgatgtttt agaaataact tgtgagggtg cgtcaggaa atcatgcagc      360 catcaggaca caggctccgg gacgtcgagc atcatcctct cctggctgaa aatgacgact     420
```

```
atgactcttc atcgtcctcc tcctccgagg ctgacgtggc tgaccgggtc tggttcatcc    480
gtgacggctg cggcatgatc tgtgctgtca tgacgtggct tctggtcgcc tatgcagact    540
tcgtggtgac tttcgtcatg ctgctgcctt ccaaagactt ctggtactct gtggtcaacg    600
gggtcatctt taactgcttg gccgtgcttg ccctgtcatc ccacctgaga accatgctca    660
ccgaccctgg ggcagtaccc aaaggaaacg ctacgaaaga atacatggag agcttgcagc    720
tgaagcctgg ggaagtcatc tacaagtgcc ccaagtgctg ctgtattaaa cccgagcgcg    780
cccaccactg cagtatttgc aaaagatgta ttcggaaaat ggatcatcac tgcccgtggg    840
tgaacaattg tgtaggagaa aagaatcaaa gatttttttgt gctcttcact atgtatatag   900
ctctgtcttc agtccatgct ctgatccttt gtggatttca gttcatctcc tgtgtccgag    960
ggcagtggac tgaatgcagt gattttttcac ctccgataac tgtaatcctg ttgatcttcc   1020
tgtgccttga gggtcttctg ttttttcactt tcactgcagt tatgtttggc acccaaatcc   1080
actccatatg caacgacgag acggagatcg agcgattgaa aagtgagaag cccacatggg   1140
agcggaggct gcgatgggaa gggatgaagt ccgtctttgg ggggcccccc tcactcctct    1200
ggatgaatcc ctttgtgggc ttccgattta ggcgactgcc cacagaccc  agaaaaggcg    1260 gcccggagtt ctcagtgtga ggcgtggctc atcagactga aacttgctca cagacttcca    1320
gttatttatt tggggtctga aggatatcaa cagctcatct gtgaccaaca gggcaactgg    1380
aacctacaca aaccaattgc ttgcagcaag cagagtttta tatatttata gtcacagatg    1440
gcagaggaag aggctctcag tccccacctg tacaacaacg aaaggtgtg  tggccacacg    1500 aagaagccaa acgccgtggc ctcctgcaga gctggggctt ctgtggagaa tacttcgggt    1560
tattacatgg gttattcaaa tcctgggtcc tgagctgctg tttccaatca tgaagaaaaa    1620
cagtgaatcc agtgaacagg gattctccaa gcagtcattt caggggctc  ctgctgaccc    1680 cgccactcag cagtgcactc cccggatcac agcaggcgt  ttacatagaa agacgttttg    1740
gtctcgatta actccgatgc tttgcgctga agttgcaaaa gatctgtgca ctgaacagtg    1800
aaggtggctt ccggcacact ccccgctgcc ccggaagaga catcctttga ccctctcagc    1860
aagtctgtgt gtgtgcgtgt ctgtgcgtgt gcgcgcgtgt gtgcatgtgt gtcaaaattg    1920
ccagtgttgt ttaggcaatg taacatttac cggctgtgta cagcaaacaa gctattttt     1980 agaaaccgac gtttcaggga agaggggaga gagccgcggg gtcctgcccg tggttactat    2040
gaatgtattg ctgttggagg acatctcgat ccaaagaaca gccgttcctg tgcggccctt    2100
cgttgccctc ctgctttcat ttttttaaaga aatcttgagt gcttgagggc cttggaactg    2160 atttttttttt tttgttccag ccaaattagc agtgtataaa tggcacctag gtaagagcag    2220
agctgcggct cggtgacttg atacttgggg cagcccgatg ctgtgtgtgg ggcaggggag    2280
gcatccttac tggagaggca gggcccagcc attgggcacc tctgggaagg ggaggggacc    2340
atgaggcagc cagcccctgg caggggcgac tgtgccaccg caggcagcgc tccagtcggg    2400
aatggccagg atggcgccct cttgttggag ttttttggtta gcttttacgt tttcttctcc    2460
acccacggca caggtgataa aataggatcc ttggtgcgga gcttaaaatt atgccagaaa    2520
gccaacagct cccctcgtgg ggccttgcct taaacttgcc tggtttgtac attttttgcc    2580
ggacgcatca agaagcaatc tgtgacaaag tctgagggtc ttcctttatg cttgccctcc    2640
acactaagag aagttggcgt ctccctcctg ggaattgttt tgcctttctg ttcatctgtg    2700
aactgttttt tgttttttaat tactctgtac cccatccgaa tcagggcttc taccactgct    2760
gatgcaaaac cacaaaggga cctacctgag ccaccgtcct agccaagcga gcaaacctgc    2820
```

```
aggggggtttg gaagtggact tggtcaccgc agaagcgtgt gcgccgttgg gggaagagct    2880
gtgtcacagc cagagggaca aagtgtgggt gatcctggag acgccagttt ccgagattgt    2940
tctgcatatt cgtttgcaca ttgttgtctg ggttggacat gcgtgtgggc ttcagtgtga    3000 ggctttttaat atgtatatcc tgttatcaat aaaacaatta tccaagtggt tgaatcctgt    3060
gagacttggc aagtgtgtgc aaatcaagta tacttgactt ttcaacctct tctttcaatg    3120
taacttttat atgaaataaa gtaatcaatt aacagttaaa aaaaaaaaa aa             3172
```

<210> SEQ ID NO 22
<211> LENGTH: 765
<212> TYPE: PRT
<213> ORGANISM: Human

<400> SEQUENCE: 22

```
Met Pro Arg Ser Pro Gly Thr Arg Leu Lys Pro Ala Lys Tyr Ile Pro
1               5                   10                  15

Val Ala Thr Ala Ala Leu Leu Val Gly Ser Ser Thr Leu Phe Phe
            20                  25                  30

Val Phe Thr Cys Pro Trp Leu Thr Arg Ala Val Ser Pro Ala Val Pro
            35                  40                  45

Val Tyr Asn Gly Ile Ile Phe Leu Phe Val Leu Ala Asn Phe Ser Met
        50                  55                  60

Ala Thr Phe Met Asp Pro Gly Val Phe Pro Arg Ala Asp Glu Asp Glu
65                  70                  75                  80

Asp Lys Glu Asp Asp Phe Arg Ala Pro Leu Tyr Lys Asn Val Asp Val
                85                  90                  95

Arg Gly Ile Gln Val Arg Met Lys Trp Cys Ala Thr Cys His Phe Tyr
            100                 105                 110

Arg Pro Pro Arg Cys Ser His Cys Ser Val Cys Asp Asn Cys Val Glu
        115                 120                 125

Asp Phe Asp His His Cys Pro Trp Val Asn Asn Cys Ile Gly Arg Arg
130                 135                 140

Asn Tyr Arg Tyr Phe Phe Leu Phe Leu Leu Ser Leu Ser Ala His Met
145                 150                 155                 160

Val Gly Val Val Ala Phe Gly Leu Val Tyr Val Leu Asn His Ala Glu
                165                 170                 175

Gly Leu Gly Ala Ala His Thr Thr Ile Thr Met Ala Val Met Cys Val
            180                 185                 190

Ala Gly Leu Phe Phe Ile Pro Val Ile Gly Leu Thr Gly Phe His Val
        195                 200                 205

Val Leu Val Thr Arg Gly Arg Thr Thr Asn Glu Gln Val Thr Gly Lys
210                 215                 220

Phe Arg Gly Gly Val Asn Pro Phe Thr Arg Gly Cys Cys Gly Asn Val
225                 230                 235                 240

Glu His Val Leu Cys Ser Pro Leu Ala Pro Arg Tyr Val Val Glu Pro
                245                 250                 255

Pro Arg Leu Pro Leu Ala Val Ser Leu Lys Pro Pro Phe Leu Arg Pro
            260                 265                 270

Glu Leu Leu Asp Arg Ala Ala Pro Leu Lys Val Lys Leu Ser Asp Asn
        275                 280                 285

Gly Leu Lys Ala Gly Leu Gly Arg Ser Lys Lys Gly Ser Leu Asp
290                 295                 300

Arg Leu Asp Glu Lys Pro Leu Asp Leu Gly Pro Pro Leu Pro Pro Lys
305                 310                 315                 320
```

```
Ile Glu Ala Gly Thr Phe Ser Ser Asp Leu Gln Thr Pro Arg Pro Gly
                325                 330                 335

Ser Ala Glu Ser Ala Leu Ser Val Gln Arg Thr Ser Pro Pro Thr Pro
                340                 345                 350

Ala Met Tyr Lys Phe Arg Pro Ala Phe Pro Thr Gly Pro Lys Val Pro
                355                 360                 365

Phe Cys Gly Pro Gly Glu Gln Val Pro Gly Pro Asp Ser Leu Thr Leu
                370                 375                 380

Gly Asp Asp Ser Ile Arg Ser Leu Asp Phe Val Ser Glu Pro Ser Leu
385                 390                 395                 400

Asp Leu Pro Asp Tyr Gly Pro Gly Leu His Ala Ala Tyr Pro Pro
                405                 410                 415

Ser Pro Pro Leu Ser Ala Ser Asp Ala Phe Ser Gly Ala Leu Arg Ser
                420                 425                 430

Leu Ser Leu Lys Ala Ser Ser Arg Arg Gly Gly Asp His Val Ala Leu
                435                 440                 445

Gln Pro Leu Arg Ser Glu Gly Gly Pro Pro Thr Pro His Arg Ser Ile
                450                 455                 460

Phe Ala Pro His Ala Leu Pro Asn Arg Asn Gly Ser Leu Ser Tyr Asp
465                 470                 475                 480

Ser Leu Leu Asn Pro Gly Ser Pro Gly Gly His Ala Cys Pro Ala His
                485                 490                 495

Pro Ala Val Gly Val Ala Gly Tyr His Ser Pro Tyr Leu His Pro Gly
                500                 505                 510

Ala Thr Gly Asp Pro Pro Arg Pro Leu Pro Arg Ser Phe Ser Pro Val
                515                 520                 525

Leu Gly Pro Arg Pro Arg Glu Pro Ser Pro Val Arg Tyr Asp Asn Leu
                530                 535                 540

Ser Arg Thr Ile Met Ala Ser Ile Gln Glu Arg Lys Asp Arg Glu Glu
545                 550                 555                 560

Arg Glu Arg Leu Leu Arg Ser Gln Ala Asp Ser Leu Phe Gly Asp Ser
                565                 570                 575

Gly Val Tyr Asp Ala Pro Ser Ser Tyr Ser Leu Gln Gln Ala Ser Val
                580                 585                 590

Leu Ser Glu Gly Pro Arg Gly Pro Ala Leu Arg Tyr Gly Ser Arg Asp
                595                 600                 605

Asp Leu Val Ala Gly Pro Gly Phe Gly Gly Ala Arg Asn Pro Ala Leu
610                 615                 620

Gln Thr Ser Leu Ser Ser Leu Ser Ser Val Ser Arg Ala Pro Arg
625                 630                 635                 640

Thr Ser Ser Ser Ser Leu Gln Ala Asp Gln Ala Ser Ser Asn Ala Pro
                645                 650                 655

Gly Pro Arg Pro Ser Ser Gly Ser His Arg Ser Pro Ala Arg Gln Gly
                660                 665                 670

Leu Pro Ser Pro Pro Gly Thr Pro His Ser Pro Ser Tyr Ala Gly Pro
                675                 680                 685

Lys Ala Val Ala Phe Ile His Thr Asp Leu Pro Glu Pro Pro Ser
                690                 695                 700

Leu Thr Val Gln Arg Asp His Pro Gln Leu Lys Thr Pro Pro Ser Lys
705                 710                 715                 720

Leu Asn Gly Gln Ser Pro Gly Leu Ala Arg Leu Gly Pro Ala Thr Gly
                725                 730                 735

Pro Pro Gly Pro Ser Ala Ser Pro Thr Arg His Thr Leu Val Lys Lys
```

```
        740               745               750
Val Ser Gly Val Gly Gly Thr Thr Tyr Glu Ile Ser Val
      755               760               765

<210> SEQ ID NO 23
<211> LENGTH: 3520
<212> TYPE: DNA
<213> ORGANISM: Human

<400> SEQUENCE: 23
ccgcgggtcc tgcgccgcgt ccagcccgcc cgcccgaccc cggcccgacc ccggccggcc      60
ctgcccgccc ggccccgggg agggatgcgg cggcgcggcg cccaggatgc cccgcagccc     120
cgggacgcgc ctcaaacccg ccaagtacat cccggtggcc acggccgccg cgctgctggt     180
cggctccagc accctcttct tcgtgttcac gtgcccgtgg ttgacacgag ctgtgtcccc     240
agctgttccc gtctacaatg gcatcatctt cctctttgtc ctggccaact tcagcatggc     300
cactttcatg gaccctggtg tttccccccg agcggatgag gatgaggaca aggaggacga     360
cttccgggct ccgctgtaca gaacgtggat gtgcgaggt atccaggtcc gcatgaagtg      420
gtgtgccacg tgccacttct accgcccgcc gcgctgctcc cactgcagcg tctgtgacaa     480
ctgtgtagag gactttgacc accactgccc ctgggtcaac aactgcatcg gcgtcgaaa      540 ctatcgctac ttcttcctgt tcctgctgtc actcagtgca cacatggtgg gcgtcgtggc     600
cttcggcctg gtctacgtgc tgaaccacgc tgaggggctg ggagccgcgc acaccaccat     660
caccatggct gtcatgtgtg tggccggcct cttcttcatc cctgtcattg gcctcactgg     720
cttccatgtg gtgctggtca ctcggggggcg caccaccaac gagcaggtga ctgggaagtt     780
ccgcgggggt gtgaaccctt tcacccgagg ctgctgtggg aatgtggagc acgtgctgtg     840 tagcccctg gcgccccggt acgtggtgga ccacccccgg ctgccgctcg cggtgagttt      900
gaagccgcct ttccttaggc ctgaactcct ggaccgagct gcaccgctca aggtcaagct     960
tagtgacaac gggctgaagg ctggcctggg ccgtagcaag tccaagggca gcctggaccg    1020
gctggatgag aagccactgg acttggggcc accactgccc ccaagatag aggctggcac     1080 gttcagcagt gacctgcaga ccccgcgccc aggcagtgct gagagtgccc tgtcggtgca    1140
gaggaccagc cccccgacac ctgccatgta caagtttagg ccggctttcc ccacgggtcc    1200
caaggtgccc ttctgtggac caggcgagca ggttccaggc cctgattccc tgaccctggg    1260
ggacgacagc atccgtagcc tggactttgt gtccgagccg agcctggacc tcctgactg     1320 tgggccaggg ggcctgcatg cagcctaccc gccatcccca ccgctcagcg cctctgatgc    1380
cttctcgggc gctttgcgct ccctgagcct caaggcctcg agccggcggg gcggggatca    1440
tgtggccctg cagcccctgc gctctgaggg ggggcccccc acgccccacc gtagcatttt    1500
tgccccccat gcactgccca accgcaacgg cagcctgtcc tatgacagcc tgctcaatcc    1560
tggctcgcct ggtggccacg cctgccctgc ccacccagca gttggcgtgg ccggataccca   1620 ctcaccctac ctgcatcctg ggcaacggg cgacccgcca cggccccta cccgcagctt     1680 cagccccgtg ctgggcccc gccccgggga ccctcgcct gtgcgctacg acaacctgtc     1740
caggaccatc atggcatcca tccaggagcg caaggacagg aggagcgtg agcgcctgct    1800 gcgctcccag gccgactcac tcttcggcga ctcaggcgtc tatgacgctc ccagctccta    1860
cagcctgcag caggccagtg tgctgtccga gggccccga ggtcccgcgc tgcgctatgg    1920
ctccagagac gaccttgtgg ctgggccgg cttcggtggc cccgcaacc tgccctgca     1980 gacgtcactg tcctcgctgt ccagctccgt gagccgtgca ccgcggacgt cgtcctcctc   2040
```

```
cctgcaggct gatcaggcca gcagcaacgc cccggggccc cggcccagca gtggctcaca    2100
caggtcacct gcacgccagg gcctgccctc ccgcccggc actccccact caccatccta     2160
cgcgggcccc aaagctgtcg ccttcatcca cacggacctc ccagagccac cgccctcgct    2220
gaccgtgcag agggaccacc ctcagctgaa gactccccca gtaagctta atgggcagtc     2280 cccgggcctg gccggctgg gacctgccac cggcccccca gggccctctg ccagccctac     2340
acggcacacg ctggttaaga aggtgtccgg cgtgggtggg accacctacg agatctcggt    2400
gtgaggactg actgccacac atccgccatg gtgccacggg gaccaggacc ccacagcgca    2460 cccccctcc ccaccaactt ctctgcccca gggacccgag gccaccccag cctggtgtgg     2520
acccatcggc gggagagagt gccacgcctc cacagcttgc cccaagcgct ctgcctgccc    2580
gtccactcat ctgcccatgg ggaagtcggc tcactgggac aagggccact gggctggtct    2640
gtgtctgggc ctgtcccatg gctggggcag tgagggggcc cagtcagcct ctttggggca    2700
ccctctctca gccaggcttg gcccactgcc atcacccagc accccagatc accgccaggc    2760
cagcccccaa tggtccccectt acggacaggt cccagagatg gacagaggca cccagggccc    2820
ccaccgtcct tctgacacag cctgtgggct cccggaccga gtgtccccg ccaggctact     2880 cctaactaac gcgttgcctt tcacggaccc cgctggaagc ttgtagcttg caaggctga    2940 tgcttctgcc ctggcctgct ctgggtggtg gtggataggt ggacagacgg ccagccagcc    3000
agctgtggcc gggggcccgg ctccatgtgt cccgtgtctg tgtgctgtgc tgccgcgccg    3060
tgtctgatgt gtcagtgctc cggccgccgc tgtccctttc atcaaagcct taacctttgc    3120
tttatgctct tgtgggaggc gacggggggg caggcgggag caggcacggg ggtgatgctg    3180
ccacaggggg ctggtgacac ccagagcccc ctccccagcc ctcaggccct ccctgccaaa    3240
ctggagaacc ccaccccaag gcatgccacg tccgcagccc cggcctggct gcggtgctcg    3300
cgccgtggga aagcacactg ggagggggtc agtgcttccc ttggtgtcag ggacctgaga    3360
gtaagcacat gacagcgtct gcttgcgttg tgtctgtttt atgtttttat atctacatct    3420
atatatctat aattttatta aaaaaagaa aagaaaaaa aaaaaaaaaa aaaaaaaaa       3480 aaaaaaaaaa aaaaaaaaaa aaaaaaaaa aaaaaaaaa                           3520
```

<210> SEQ ID NO 24
<211> LENGTH: 364
<212> TYPE: PRT
<213> ORGANISM: Human

<400> SEQUENCE: 24

```
Met Ser Val Met Val Arg Lys Lys Val Thr Arg Lys Trp Glu Lys
1               5                   10                  15

Leu Pro Gly Arg Asn Thr Phe Cys Cys Asp Gly Arg Val Met Met Ala
                20                  25                  30

Arg Gln Lys Gly Ile Phe Tyr Leu Thr Leu Phe Leu Ile Leu Gly Thr
            35                  40                  45

Cys Thr Leu Phe Phe Ala Phe Glu Cys Arg Tyr Leu Ala Val Gln Leu
        50                  55                  60

Ser Pro Ala Ile Pro Val Phe Ala Ala Met Leu Phe Leu Phe Ser Met
65                  70                  75                  80

Ala Thr Leu Leu Arg Thr Ser Phe Ser Asp Pro Gly Val Ile Pro Arg
                85                  90                  95

Ala Leu Pro Asp Glu Ala Phe Ile Glu Met Glu Ile Glu Ala Thr
            100                 105                 110
```

```
Asn Gly Ala Val Pro Gln Gly Gln Arg Pro Pro Arg Ile Lys Asn
        115                 120                 125
Phe Gln Ile Asn Asn Gln Ile Val Lys Leu Lys Tyr Cys Tyr Thr Cys
130                 135                 140
Lys Ile Phe Arg Pro Pro Arg Ala Ser His Cys Ser Ile Cys Asp Asn
145                 150                 155                 160
Cys Val Glu Arg Phe Asp His His Cys Pro Trp Val Gly Asn Cys Val
                165                 170                 175
Gly Lys Arg Asn Tyr Arg Tyr Phe Tyr Leu Phe Ile Leu Ser Leu Ser
                180                 185                 190
Leu Leu Thr Ile Tyr Val Phe Ala Phe Asn Ile Val Tyr Val Ala Leu
        195                 200                 205
Lys Ser Leu Lys Ile Gly Phe Leu Glu Thr Leu Lys Glu Thr Pro Gly
210                 215                 220
Thr Val Leu Glu Val Leu Ile Cys Phe Phe Thr Leu Trp Ser Val Val
225                 230                 235                 240
Gly Leu Thr Gly Phe His Thr Phe Leu Val Ala Leu Asn Gln Thr Thr
                245                 250                 255
Asn Glu Asp Ile Lys Gly Ser Trp Thr Gly Lys Asn Arg Val Gln Asn
                260                 265                 270
Pro Tyr Ser His Gly Asn Ile Val Lys Asn Cys Cys Glu Val Leu Cys
        275                 280                 285
Gly Pro Leu Pro Pro Ser Val Leu Asp Arg Arg Gly Ile Leu Pro Leu
        290                 295                 300
Glu Glu Ser Gly Ser Arg Pro Pro Ser Thr Gln Glu Thr Ser Ser Ser
305                 310                 315                 320
Leu Leu Pro Gln Ser Pro Ala Pro Thr Glu His Leu Asn Ser Asn Glu
                325                 330                 335
Met Pro Glu Asp Ser Ser Thr Pro Glu Glu Met Pro Pro Pro Glu Pro
                340                 345                 350
Pro Glu Pro Pro Gln Glu Ala Ala Glu Ala Glu Lys
        355                 360

<210> SEQ ID NO 25
<211> LENGTH: 2949
<212> TYPE: DNA
<213> ORGANISM: Human

<400> SEQUENCE: 25
tgaggagcgt tccatttggc cagtggtggg cggttgccac agctggttta gggccccgac    60
cactggggcc ccttgtcagg aggagacagc ctcccggccc ggggaggaca gtcgctgcc   120
acctttggct gccgacgtga ttccctggga cggtccgttt cctgccgtca gctgccggcc   180
gagttgggtc tccgtggttc aggccggctc ccccttcctg gtctcccttc tcccgctggg   240
ccggtttatc gggaggagat tgtcttccag ggctagcaat tggacttttg atgatgtttg   300
acccagcggc aggaatagca ggcaacgtga tttcaaagct gggctcagcc tctgtttctt   360
ctctcgtgta atcgcaaaac ccattttgga gcaggaattc caatcatgtc tgtgatggtg   420
gtgagaaaga aggtgacacg gaaatgggag aaactcccag gcaggaacac cttttgctgt   480
gatggccgcg tcatgatggc ccggcaaaag gcattttct acctgacccct tttcctcatc   540
ctggggacat gtacactctt cttcgccttt gagtgccgct acctggctgt tcagctgtct   600
cctgccatcc ctgtatttgc tgccatgctc ttcctttttct ccatggctac actgttgagg   660
accagcttca gtgaccctgg agtgattcct cgggcgctac cagatgaagc agctttcata   720
```

```
gaaatggaga tagaagctac caatggtgcg gtgccccagg gccagcgacc accgcctcgt    780
atcaagaatt tccagataaa caaccagatt gtgaaactga atactgtta cacatgcaag    840
atcttccggc ctccccgggc ctcccattgc agcatctgtg acaactgtgt ggagcgcttc    900
gaccatcact gccctgggt ggggaattgt gttggaaaga gaactaccg ctacttctac      960
ctcttcatcc tttctctctc cctcctcaca atctatgtct tcgccttcaa catcgtctat   1020
gtggccctca aatctttgaa aattggcttc ttggagacat tgaaagaaac tcctggaact   1080
gttctagaag tcctcatttg cttctttaca ctctggtccg tcgtgggact gactggattt   1140
catactttcc tcgtggctct caaccagaca accaatgaag acatcaaagg atcatggaca   1200
gggaagaatc gcgtccagaa tccctacagc catggcaata ttgtgaagaa ctgctgtgaa   1260
gtgctgtgtg gccccttgcc ccccagtgtg ctggatcgaa ggggtatttt gccactggag   1320
gaaagtggaa gtcgacctcc cagtactcaa gagaccagta gcagcctctt gccacagagc   1380
ccagccccca cagaacacct gaactcaaat gagatgccgg aggacagcag cactcccgaa   1440
gagatgccac ctccagagcc cccagagcca ccacaggagg cagctgaagc tgagaagtag   1500
cctatctatg gaagagactt tgtttgtgt ttaattaggg ctatgagaga tttcaggtga    1560
gaagttaaac ctgagacaga gagcaagtaa gctgtccctt ttaactgttt ttctttggtc   1620
tttagtcacc cagttgcaca ctggcatttt cttgctgcaa gctttttttaa atttctgaac  1680
tcaaggcagt ggcagaagat gtcagtcacc tctgataact ggaaaaatgg gtctcttggg   1740
ccctggcact ggttctccat ggcctcagcc acagggtccc cttggacccc ctctcttccc   1800
tccagatccc agccctcctg cttggggtca ctggtctcat tctggggcta aaagtttttg   1860
agactggctc aaatcctccc aagctgctgc acgtgctgag tccagaggca gtcacagaga   1920
cctctggcca ggggatccta actgggttct tggggtcttc aggactgaag aggagggaga   1980
gtggggtcag aagattctcc tggccaccaa gtgccagcat tgcccacaaa tcctttttagg  2040
aatgggacag gtaccttcca cttgttgtat ttattagtgt agcttctcct ttgtctccca   2100
tccactctga cacctaagcc ccactctttt cccattagat atatgtaagt agttgtagta   2160
gagataataa ttgacatttc tcgtagacta cccagaaact ttttttaatac ctgtgccatt  2220
ctcaataaga atttatgaga tgccagcggc atagcccttc acactctctg tctcatctct   2280
cctcctttct cattagcccc ttttaatttg ttttttcctttt tgactcctgc tcccattagg  2340
agcaggaatg gcagtaataa aagtctgcac tttggtcatt tcttttcctc agaggaagcc   2400
tgagtgctca cttaaacact atcccctcag actccctgtg tgaggcctgc agaggccctg    2460
aatgcacaaa tgggaaacca aggcacagag aggctctcct ctcctctcct ctccccgat    2520
gtaccctcaa aaaaaaaaa atgctaacca gttcttccat taagcctcgg ctgagtgagg     2580
gaaagcccag cactgctgcc ctctcgggta actcacccta aggcctcggc ccacctctgg    2640
ctatggtaac cacactgggg gcttcctcca agccccgctc ttccagcact tccaccggca    2700
gagtcccaga gccacttcac cctgggggtg ggctgtggcc cccagtcagc tctgctcagg    2760
acctgctcta tttcagggaa gaagatttat gtattatatg tggctatatt tcctagagca    2820
cctgtgtttt cctctttcta agccagggtc ctgtctggat gacttatgcg gtgggggagt    2880
gtaaaccaga acttttcatc tatttgaagg cgattaaact gtgtctaatg caaaaaaaaa    2940
aaaaaaaaa                                                          2949
```

<210> SEQ ID NO 26
<211> LENGTH: 412
<212> TYPE: PRT

<213> ORGANISM: Human

<400> SEQUENCE: 26

Met Asp Thr Arg Ser Gly Ser Gln Cys Ser Val Thr Pro Glu Ala Ile
1               5                   10                  15

Leu Asn Asn Glu Lys Leu Val Leu Pro Pro Arg Ile Ser Arg Val Asn
            20                  25                  30

Gly Trp Ser Leu Pro Leu His Tyr Phe Gln Val Val Thr Trp Ala Val
        35                  40                  45

Phe Val Gly Leu Ser Ser Ala Thr Phe Gly Ile Phe Ile Pro Phe Leu
    50                  55                  60

Pro His Ala Trp Lys Tyr Ile Ala Tyr Val Val Thr Gly Gly Ile Phe
65                  70                  75                  80

Ser Phe His Leu Val His Leu Ile Ala Ser Cys Ile Asp Pro Ala
                85                  90                  95

Asp Ser Asn Val Arg Leu Met Lys Asn Tyr Ser Gln Pro Met Pro Leu
            100                 105                 110

Phe Asp Arg Ser Lys His Ala His Val Ile Gln Asn Gln Phe Cys His
        115                 120                 125

Leu Cys Lys Val Thr Val Asn Lys Thr Lys His Cys Ile Ser Cys
130                 135                 140

Asn Lys Cys Val Ser Gly Phe Asp His His Cys Lys Trp Ile Asn Asn
145                 150                 155                 160

Cys Val Gly Ser Arg Asn Tyr Trp Phe Phe Phe Ser Thr Val Ala Ser
                165                 170                 175

Ala Thr Ala Gly Met Leu Cys Leu Ile Ala Ile Leu Leu Tyr Val Leu
            180                 185                 190

Val Gln Tyr Leu Val Asn Pro Gly Val Leu Arg Thr Asp Pro Arg Tyr
        195                 200                 205

Glu Asp Val Lys Asn Met Asn Thr Trp Leu Leu Phe Leu Pro Leu Phe
    210                 215                 220

Pro Val Gln Val Gln Thr Leu Ile Val Val Ile Gly Met Leu Val
225                 230                 235                 240

Leu Leu Leu Asp Phe Leu Gly Leu Val His Leu Gly Gln Leu Leu Ile
                245                 250                 255

Phe His Ile Tyr Leu Lys Ala Lys Lys Met Thr Thr Phe Glu Tyr Leu
            260                 265                 270

Ile Asn Asn Arg Lys Glu Glu Ser Ser Lys His Gln Ala Val Arg Lys
        275                 280                 285

Asp Pro Tyr Val Gln Met Asp Lys Gly Val Leu Gln Gln Gly Ala Gly
    290                 295                 300

Ala Leu Gly Ser Ser Ala Gln Gly Val Lys Ala Lys Ser Ser Leu Leu
305                 310                 315                 320

Ile His Lys His Leu Cys His Phe Cys Thr Ser Val Asn Gln Asp Gly
                325                 330                 335

Asp Ser Thr Ala Arg Glu Gly Asp Glu Asp Pro Cys Pro Ser Ala Leu
            340                 345                 350

Gly Ala Lys Ala Arg Asn Ser Arg Leu Ile Cys Arg Arg Leu Cys Gln
        355                 360                 365

Phe Ser Arg Val His Pro Asp Gly Gly Ser Met Ala Gln Glu Ala
    370                 375                 380

Asp Asp Ala Pro Ser Ile Ser Thr Leu Gly Leu Gln Gln Glu Thr Thr
385                 390                 395                 400

Glu Pro Met Lys Thr Asp Ser Ala Glu Ser Glu Asp

<210> SEQ ID NO 27
<211> LENGTH: 2623
<212> TYPE: DNA
<213> ORGANISM: Human

<400> SEQUENCE: 27

| | | | | | |
|---|---|---|---|---|---|
| gtgaacgggt | tgtgggacct | gtcgctgtgt | gggggctgtc | gagcactccc | cagaacgtaa | 60 |
| caaatcctca | ggggaactga | tgggcggtcg | cgcgggcact | gggtcctcca | caccctggag | 120 |
| agccgttttc | cgttgccact | cggctctggc | cggggtcaca | ttctgcagca | tgtctgttca | 180 |
| ttcccctggg | cggggccctg | caccgactcc | agcccagccc | ctgctccctc | tgcggggaac | 240 |
| gtggccccag | gcagtgctgg | gccattggct | gtcagtgctg | gtcctggcgg | ctgcattccc | 300 |
| agtccccttg | gtctctgtga | cagtgggcgg | ggccggccct | cccaggatct | gacggcgcag | 360 |
| gtcctcccct | tctgtgtcct | gcagatggac | cccgctccg | ggagccagtg | ttccgtcacc | 420 |
| ccagaagcca | tactcaataa | tgaaaagctg | gtcttgccgc | cccgcatctc | cagagtgaac | 480 |
| ggctggtcgt | taccccctgca | ctacttccag | gtggtgacct | gggctgtctt | cgtgggcctt | 540 |
| tcctcggcca | ccttcgggat | cttcattccc | ttcctgcctc | acgcgtggaa | atacattgcc | 600 |
| tacgtggtga | ccgggggggat | cttctcgttc | cacctcgtcg | tccacctgat | cgcgtcctgc | 660 |
| atcgacccgg | ccgactccaa | tgtcagactc | atgaagaact | attctcagcc | catgcccctc | 720 |
| ttcgacagat | caaaacatgc | acacgtgatc | cagaatcagt | tctgccacct | gtgcaaggtc | 780 |
| accgtgaaca | agaaaaccaa | acactgcatt | tcctgcaata | agtgtgtgtc | cggcttcgac | 840 |
| caccactgca | aatggatcaa | caactgcgtg | ggaagccgga | attattggtt | cttcttcagc | 900 |
| actgtggcct | cggccacagc | tggcatgctc | tgcctgatcg | ccatcctgct | gtatgtcctc | 960 |
| gtccagtacc | tcgtgaaccc | cggggtgctc | cgcacggacc | ccaggtatga | agatgtcaag | 1020 |
| aatatgaaca | cgtggctgct | gttcctcccc | ctgttcccgg | tgcaggtgca | gaccctgata | 1080 |
| gtcgtgatca | tcgggatgct | cgtgctcctg | ctggactttc | ttggcttggt | gcacctgggc | 1140 |
| cagctgctca | tcttccacat | ctacctgaag | gccaagaaga | tgaccacctt | tgagtatctc | 1200 |
| attaataacc | gcaaagaaga | gagttcaaaa | catcaagcag | tgaggaaaga | tccatacgtg | 1260 |
| caaatggaca | aaggagttct | ccagcaagga | gctggcgccc | tgggctcatc | tgcacaggga | 1320 |
| gtcaaagcca | gagctcccct | gctgattcac | aagcactat | gtcacttctg | cacttcagta | 1380 |
| aaccaggatg | gggattcgac | ggcacgggaa | ggggatgaag | acccgtgtcc | atctgcactt | 1440 |
| ggagccaagg | ccaggaactc | ccggctgatt | tgcaggcgcc | tgtgtcagtt | ctccactcgt | 1500 |
| gtacacccag | acgggggctc | gatggcacag | gaagcagatg | atgccccgag | tatatctaca | 1560 |
| cttgggctgc | aacaagaaac | aacagagccc | atgaaaactg | acagtgctga | aagtgaagac | 1620 |
| tgagattcag | gagctcaggt | gcccctgtga | tccaggtctt | ctaccctgaa | accccaccct | 1680 |
| ccatcaaggt | cctgcctgta | gagtctacct | tgcaaagcct | cctgctccta | cccatgctac | 1740 |
| aggccaggaa | ccagagccca | tcatctcaga | ggccctgga | tgtccttcga | aggaaccagg | 1800 |
| accctcagag | cccagcatcc | atctctgtca | tcatcttcat | cacacccaaa | gaagagccag | 1860 |
| ccttgcagga | gggtttacat | ctccaggaag | atgggctgcc | agcaactgca | gaggatgcag | 1920 |
| ccacctgctt | aactgtgctg | tccagccagc | cagccagctg | cagggcctct | tgctgcttaa | 1980 |
| gagctgatgg | gccgggcatg | ttggctcaca | cctgtgagca | cagtactggg | aaatgggagc | 2040 |
| acagtactag | gaaatgggag | cacagtactg | ggaaatggga | gcacagtact | gggaaatggg | 2100 |

-continued

```
ggctcacagc actgcaaaat gggagcacag tattgggaaa tgggagcaca gtactgggaa    2160
gtgggagcac agtactgaga agtgggagca cagtactgag aaatgggagt acactactga    2220
gaaatgggag cacagtactg ggaaatgggc atacagtact gggaaatggg catacagtac    2280
tgagaaatgg gagcacagta ctgggaaatg gagcacagt  actgggaaat gggagcccac    2340
agtactggga agggagtt  cacagtactc ggaaatggga gcatagtact gggaaatggg    2400
agcacagtac tggaaatgg gagcatagta ctgggaaacc ccagacctgg attctgagtt    2460
tttcagccta gcccagactt cttatcttag tagacaaaaa gagtcaatac cagagaacca    2520
gaggcatcct ctgtatttta atgaactctg cattttaatc tgtttagtag tcattttta    2580 aaagataatc agttttccaa atatatctat aagttactac gtg                      2623
```

<210> SEQ ID NO 28
<211> LENGTH: 267
<212> TYPE: PRT
<213> ORGANISM: Human

<400> SEQUENCE: 28

```
Met Ala Pro Trp Ala Leu Leu Ser Pro Gly Val Leu Val Arg Thr Gly
1               5                   10                  15

His Thr Val Leu Thr Trp Gly Ile Thr Leu Val Leu Phe Leu His Asp
                20                  25                  30

Thr Glu Leu Arg Gln Trp Glu Gln Gly Glu Leu Leu Leu Pro Leu
            35                  40                  45

Thr Phe Leu Leu Val Leu Gly Ser Leu Leu Leu Tyr Leu Ala Val
        50                  55                  60

Ser Leu Met Asp Pro Gly Tyr Val Asn Val Gln Pro Gln Pro Gln Glu
65                  70                  75                  80

Glu Leu Lys Glu Glu Gln Thr Ala Met Val Pro Pro Ala Ile Pro Leu
                85                  90                  95

Arg Arg Cys Arg Tyr Cys Leu Val Leu Gln Pro Leu Arg Ala Arg His
            100                 105                 110

Cys Arg Glu Cys Arg Arg Cys Val Arg Arg Tyr Asp His His Cys Pro
        115                 120                 125

Trp Met Glu Asn Cys Val Gly Glu Arg Asn His Pro Leu Phe Val Val
    130                 135                 140

Tyr Leu Ala Leu Gln Leu Val Val Leu Leu Trp Gly Leu Tyr Leu Ala
145                 150                 155                 160

Trp Ser Gly Leu Arg Phe Phe Gln Pro Trp Gly Leu Trp Leu Arg Ser
                165                 170                 175

Ser Gly Leu Leu Phe Ala Thr Phe Leu Leu Ser Leu Phe Ser Leu
            180                 185                 190

Val Ala Ser Leu Leu Leu Val Ser His Leu Tyr Leu Val Ala Ser Asn
        195                 200                 205

Thr Thr Thr Trp Glu Phe Ile Ser Ser His Arg Ile Ala Tyr Leu Arg
    210                 215                 220

Gln Arg Pro Ser Asn Pro Phe Asp Arg Gly Leu Thr Arg Asn Leu Ala
225                 230                 235                 240

His Phe Phe Cys Gly Trp Pro Ser Gly Ser Trp Glu Thr Leu Trp Ala
                245                 250                 255

Glu Glu Glu Glu Glu Gly Ser Ser Pro Ala Val
            260                 265
```

<210> SEQ ID NO 29
<211> LENGTH: 1184

<212> TYPE: DNA
<213> ORGANISM: Human

<400> SEQUENCE: 29

```
gggcgcttct tccgggtggg gccccgggcc gaggcgatgg cgccctgggc gctcctcagc      60
cctggggtcc tggtgcggac cgggcacacc gtgctgacct ggggaatcac gctggtgctc     120
ttcctgcacg ataccgagct gcggcaatgg gaggagcagg gggagctgct cctgcccctc     180
accttcctgc tcctggtgct gggctccctg ctgctctacc tcgctgtgtc actcatggac     240
cctggctacg tgaatgtgca gccccagcct caggaggagc tcaaagagga gcagacagcc     300
atggttcctc cagccatccc tcttcggcgc tgcagatact gcctggtgct gcagcccctg     360
agggctcggc actgccgtga gtgccgccgt tgcgtccgcc gctacgacca ccactgcccc     420
tggatggaga actgtgtggg agagcgcaac cacccactct ttgtggtcta cctggcgctg     480
cagctggtgg tgcttctgtg gggcctgtac ctggcatggt caggcctccg gttcttccag     540
ccctggggtc tgtggttgcg gtccagcggg ctcctgttcg ccaccttcct gctgctgtcc     600
ctcttctcgt tggtggccag cctgctcctc gtctcgcacc tctacctggt ggccagcaac     660
accaccacct gggaattcat ctcctcacac cgcatcgcct atctccgcca gcgccccagc     720
aaccccttcg accgaggcct gacccgcaac ctggcccact tcttctgtgg atggccctca     780
gggtcctggg agaccctctg ggctgaggag gaggaagagg gcagcagccc agctgtttag     840
ggttgctgga ggccgggcta ccgtcttgtg cctgaaaacc acggggcctg tcccagctg     900
gggtgagcgc tcagagggcc tggggccctc actcctgccc acgcctccca gaccccagaa     960
cggagcttca agtcagacag atccctgcct tggtgggcag ttctgccttc caaggaagaa    1020
ggggaagaaa aggacctgtg ggtggctcag gcccaagcag accccgggct ccaccccagc    1080
cccgcccagg ctgctgccag tgcacacttt tacaaattta atataaagca agtccagtct    1140
taaaaagaca aaaaaaaaaa aaaaaaaaaa aaaaaaaaaa aaaa                      1184
```

<210> SEQ ID NO 30
<211> LENGTH: 622
<212> TYPE: PRT
<213> ORGANISM: Human

<400> SEQUENCE: 30

```
Met Glu Gly Pro Gly Leu Gly Ser Gln Cys Arg Asn His Ser His Gly
1               5                   10                  15

Pro His Pro Pro Gly Phe Gly Arg Tyr Gly Ile Cys Ala His Glu Asn
            20                  25                  30

Lys Glu Leu Ala Asn Ala Arg Glu Ala Leu Pro Leu Ile Glu Asp Ser
        35                  40                  45

Ser Asn Cys Asp Ile Val Lys Ala Thr Gln Tyr Gly Ile Phe Glu Arg
    50                  55                  60

Cys Lys Glu Leu Val Glu Ala Gly Tyr Asp Val Arg Gln Pro Asp Lys
65                  70                  75                  80

Glu Asn Val Ser Leu Leu His Trp Ala Ala Ile Asn Asn Arg Leu Asp
                85                  90                  95

Leu Val Lys Phe Tyr Ile Ser Lys Gly Ala Val Val Asp Gln Leu Gly
            100                 105                 110

Gly Asp Leu Asn Ser Thr Pro Leu His Trp Ala Ile Arg Gln Gly His
        115                 120                 125

Leu Pro Met Val Ile Leu Leu Gln His Gly Ala Asp Pro Thr Leu
    130                 135                 140
```

-continued

Ile Asp Gly Glu Gly Phe Ser Ser Ile His Leu Ala Val Leu Phe Gln
145                 150                 155                 160

His Met Pro Ile Ile Ala Tyr Leu Ile Ser Lys Gly Gln Ser Val Asn
            165                 170                 175

Met Thr Asp Val Asn Gly Gln Thr Pro Leu Met Leu Ser Ala His Lys
        180                 185                 190

Val Ile Gly Pro Glu Pro Thr Gly Phe Leu Leu Lys Phe Asn Pro Ser
    195                 200                 205

Leu Asn Val Val Asp Lys Ile His Gln Asn Thr Pro Leu His Trp Ala
210                 215                 220

Val Ala Ala Gly Asn Val Asn Ala Val Asp Lys Leu Leu Glu Ala Gly
225                 230                 235                 240

Ser Ser Leu Asp Ile Gln Asn Val Lys Gly Glu Thr Pro Leu Asp Met
                245                 250                 255

Ala Leu Gln Asn Lys Asn Gln Leu Ile Ile His Met Leu Lys Thr Glu
            260                 265                 270

Ala Lys Met Arg Ala Asn Gln Lys Phe Arg Leu Trp Arg Trp Leu Gln
        275                 280                 285

Lys Cys Glu Leu Phe Leu Leu Leu Met Leu Ser Val Ile Thr Met Trp
    290                 295                 300

Ala Ile Gly Tyr Ile Leu Asp Phe Asn Ser Asp Ser Trp Leu Leu Lys
305                 310                 315                 320

Gly Cys Leu Leu Val Thr Leu Phe Phe Leu Thr Ser Leu Phe Pro Arg
                325                 330                 335

Phe Leu Val Gly Tyr Lys Asn Leu Val Tyr Leu Pro Thr Ala Phe Leu
            340                 345                 350

Leu Ser Ser Val Phe Trp Ile Phe Met Thr Trp Phe Ile Leu Phe Phe
        355                 360                 365

Pro Asp Leu Ala Gly Ala Pro Phe Tyr Phe Ser Phe Ile Phe Ser Ile
    370                 375                 380

Val Ala Phe Leu Tyr Phe Tyr Lys Thr Trp Ala Thr Asp Pro Gly
385                 390                 395                 400

Phe Thr Lys Ala Ser Glu Glu Lys Lys Val Asn Ile Ile Thr Leu
                405                 410                 415

Ala Glu Thr Gly Ser Leu Asp Phe Arg Thr Phe Cys Thr Ser Cys Leu
            420                 425                 430

Ile Arg Lys Pro Leu Arg Ser Leu His Cys His Val Cys Asn Cys Cys
        435                 440                 445

Val Ala Arg Tyr Asp Gln His Cys Leu Trp Thr Gly Arg Cys Ile Gly
    450                 455                 460

Phe Gly Asn His His Tyr Tyr Ile Phe Phe Leu Phe Phe Leu Ser Met
465                 470                 475                 480

Val Cys Gly Trp Ile Ile Tyr Gly Ser Phe Ile Tyr Leu Ser Ser His
                485                 490                 495

Cys Ala Thr Thr Phe Lys Glu Asp Gly Leu Trp Thr Tyr Leu Asn Gln
            500                 505                 510

Ile Val Ala Cys Ser Pro Trp Val Leu Tyr Ile Leu Met Leu Ala Thr
        515                 520                 525

Phe His Phe Ser Trp Ser Thr Phe Leu Leu Leu Asn Gln Leu Phe Gln
    530                 535                 540

Ile Ala Phe Leu Gly Leu Thr Ser His Glu Arg Ile Ser Leu Gln Lys
545                 550                 555                 560

Gln Ser Lys His Met Lys Gln Thr Leu Ser Leu Arg Lys Thr Pro Tyr
                565                 570                 575

```
Asn Leu Gly Phe Met Gln Asn Leu Ala Asp Phe Phe Gln Cys Gly Cys
            580                 585                 590

Phe Gly Leu Val Lys Pro Cys Val Val Asp Trp Thr Ser Gln Tyr Thr
        595                 600                 605

Met Val Phe His Pro Ala Arg Glu Lys Val Leu Arg Ser Val
    610                 615                 620

<210> SEQ ID NO 31
<211> LENGTH: 2448
<212> TYPE: DNA
<213> ORGANISM: Human

<400> SEQUENCE: 31
```

| | | | | |
|---|---|---|---|---|
| gggcgccagc | aggaagtggg | agaagaggcg | acccaaggcg | ggctggcggg | ctggcggcag | 60 |
| tcgctacttg | cctagtagcc | tcagccgctg | tgggctcctg | gggagatgga | ggggccgggg | 120 |
| ctgggctcgc | agtgcaggaa | tcacagccat | ggcccccacc | ctccaggatt | tggtcgatat | 180 |
| ggcatctgtg | cacatgaaaa | caaagaactt | gccaatgcaa | gagaagctct | tcctcttata | 240 |
| gaggactcta | gtaactgtga | cattgtcaaa | gctactcaat | acggaatttt | tgaacgatgt | 300 |
| aaagagttgg | tagaagcagg | atatgatgtc | aggcaaccag | ataaagaaaa | tgtgtcgctt | 360 |
| cttcattggg | ctgctattaa | caacagactg | gatcttgtaa | agtttttatat | ttcaaaaggt | 420 |
| gctgttgtag | atcagttggg | tggagattta | aattcaactc | ctcttcactg | ggccatccga | 480 |
| caaggacatt | tacctatggt | catattatta | ctccagcatg | gtgcagaccc | cactcttatt | 540 |
| gatggagagg | gattcagcag | catccacctg | gcagtattgt | ttcaacacat | gcctattata | 600 |
| gcatatctca | tctcaaaggg | acagagtgtg | aatatgacag | atgtaaatgg | gcagacacct | 660 |
| ctcatgttat | cagctcacaa | agtaattggg | ccagaaccaa | ctggatttct | tttaaagttt | 720 |
| aatccttctc | tcaatgtggt | tgataaaata | caccaaaaca | ctccacttca | ctgggcagtt | 780 |
| gcagcaggaa | atgttaatgc | agttgataag | cttttggaag | ctggttctag | cctggatatc | 840 |
| cagaatgtta | agggagaaac | acctcttgat | atggctctac | aaaacaaaaa | tcagctcatt | 900 |
| attcatatgc | taaaaacaga | agccaaaatg | agagccaacc | aaaagttcag | actttggagg | 960 |
| tggctgcaga | aatgcgagct | cttcctgctg | ctgatgcttt | ctgtgattac | catgtgggct | 1020 |
| attggataca | tattggactt | caattcagat | tcttggcttt | taaaggatg | tcttctagta | 1080 |
| acactgtttt | ttctgacatc | tttgtttcca | aggttcttgg | ttgggtataa | gaaccttgta | 1140 |
| tacttaccaa | cagcctttct | gctaagttct | gttttttgga | tatttatgac | ttggttcatc | 1200 |
| ttattttttc | ctgatttagc | aggagcccct | ttctatttca | gtttcatttt | cagcatagta | 1260 |
| gcctttctat | actttttcta | taagacttgg | gcaactgatc | caggcttcac | taaggcttct | 1320 |
| gaagaagaaa | agaaagtgaa | tatcatcacc | cttgcagaaa | ctggctctct | ggacttcaga | 1380 |
| acattttgta | catcatgtct | tataaggaag | ccattaaggt | cactccactg | ccatgtatgc | 1440 |
| aactgctgtg | tggctcgata | tgatcaacac | tgcctgtgga | ctggacggtg | cataggtttt | 1500 |
| ggcaaccatc | actattacat | attcttcttg | tttttccttt | ccatggtatg | tggctggatt | 1560 |
| atatatggat | ctttcatcta | tttgtccagt | cattgtgcca | caacattcaa | agaagatgga | 1620 |
| ttatggactt | acctcaatca | gattgtggcc | tgttcccctt | gggttttata | tatcttgatg | 1680 |
| ctagcaactt | tccatttctc | atggtcaaca | ttttattat | taaatcaact | cttcagatt | 1740 |
| gcctttctgg | gcctgacctc | ccatgagaga | atcagcctgc | agaagcagag | caagcatatg | 1800 |
| aaacagacgt | tgtccctcag | gaagacacca | tacaatcttg | gattcatgca | gaacctggca | 1860 |

```
gatttctttc agtgtggctg ctttggcttg gtgaagccct gtgtggtaga ttggacatca   1920
cagtacacca tggtctttca cccagccagg gagaaggttc ttcgctcagt atgaagaaaa   1980
gcaacccaaa actctcaatc tgatttgttt ttgtttatgt cgatgccctg tagtttgaaa   2040
gtgaagtaaa gatttagaat tcacctaagt ccaaaggaaa acacgtggtt tttaaagcca   2100
ttaggtaaaa aaagttctca ataaaggcat tacaattttt taggtttaga aagatggact   2160
tttctgataa atcttggcag acatctaaaa aaaaaaccat attttcaca agaaaatgca    2220 agttactttt tttggaaata atactcactg attatggata aaatggaata ttttcagata   2280
ctatattggc tgtttcaaaa tagtactatt ctttaaactt gtaattttg ctaagttatt    2340 tgtctttgtt gtatctataa atatgtaaaa aatatttaaa tagatgtacc tgttttgctt   2400
tcacacttaa taaaaattt ttttttgtag ttgaaaaaaa aaaaaaaa                 2448
```

<210> SEQ ID NO 32
<211> LENGTH: 473
<212> TYPE: PRT
<213> ORGANISM: Human

<400> SEQUENCE: 32

```
Met Pro Pro Gly Gly Gly Gly Pro Met Lys Asp Cys Glu Tyr Ser Gln
1               5                   10                  15

Ile Ser Thr His Ser Ser Ser Pro Met Glu Ser Pro His Lys Lys Lys
            20                  25                  30

Lys Ile Ala Ala Arg Arg Lys Trp Glu Val Phe Pro Gly Arg Asn Lys
        35                  40                  45

Phe Phe Cys Asn Gly Arg Ile Met Met Ala Arg Gln Thr Gly Val Phe
    50                  55                  60

Tyr Leu Thr Leu Val Leu Ile Leu Val Thr Ser Gly Leu Phe Phe Ala
65                  70                  75                  80

Phe Asp Cys Pro Tyr Leu Ala Val Lys Ile Thr Pro Ala Ile Pro Ala
                85                  90                  95

Val Ala Gly Ile Leu Phe Phe Val Met Gly Thr Leu Leu Arg Thr
            100                 105                 110

Ser Phe Ser Asp Pro Gly Val Leu Pro Arg Ala Thr Pro Asp Glu Ala
        115                 120                 125

Ala Asp Leu Glu Arg Gln Ile Asp Ile Ala Asn Gly Thr Ser Ser Gly
    130                 135                 140

Gly Tyr Arg Pro Pro Arg Thr Lys Glu Val Ile Ile Asn Gly Gln
145                 150                 155                 160

Thr Val Lys Leu Lys Tyr Cys Phe Thr Cys Lys Ile Phe Arg Pro Pro
                165                 170                 175

Arg Ala Ser His Cys Ser Leu Cys Asp Asn Cys Val Glu Arg Phe Asp
            180                 185                 190

His His Cys Pro Trp Val Gly Asn Cys Val Gly Lys Arg Asn Tyr Arg
        195                 200                 205

Phe Phe Tyr Met Phe Ile Leu Ser Leu Ser Phe Leu Thr Val Phe Ile
    210                 215                 220

Phe Ala Phe Val Ile Thr His Val Ile Leu Arg Ser Gln Gln Thr Gly
225                 230                 235                 240

Phe Leu Asn Ala Leu Lys Asp Ser Pro Ala Ser Val Leu Glu Ala Val
                245                 250                 255

Val Cys Phe Phe Ser Val Trp Ser Ile Val Gly Leu Ser Gly Phe His
            260                 265                 270

Thr Tyr Leu Ile Ser Ser Asn Gln Thr Thr Asn Glu Asp Ile Lys Gly
```

```
                    275                 280                 285
Ser Trp Ser Asn Lys Arg Gly Lys Glu Asn Tyr Asn Pro Tyr Ser Tyr
    290                 295                 300

Gly Asn Ile Phe Thr Asn Cys Cys Val Ala Leu Cys Gly Pro Ile Ser
305                 310                 315                 320

Pro Ser Leu Ile Asp Arg Arg Gly Tyr Ile Gln Pro Asp Thr Pro Gln
                325                 330                 335

Pro Ala Ala Pro Ser Asn Gly Ile Thr Met Tyr Gly Ala Thr Gln Ser
            340                 345                 350

Gln Ser Asp Met Ala Ala Thr Pro Leu Leu Gln Ser Glu Pro Ser
        355                 360                 365

Leu Thr Ser Asp Glu Leu His Leu Pro Gly Lys Pro Gly Leu Gly Thr
    370                 375                 380

Pro Cys Ala Ser Leu Thr Leu Gly Pro Pro Thr Pro Pro Ala Ser Met
385                 390                 395                 400

Pro Asn Leu Ala Glu Ala Thr Leu Ala Asp Val Met Pro Arg Lys Asp
                405                 410                 415

Glu His Met Gly His Gln Phe Leu Thr Pro Asp Glu Ala Pro Ser Pro
            420                 425                 430

Pro Arg Leu Leu Ala Ala Gly Ser Pro Leu Ala His Ser Arg Thr Met
        435                 440                 445

His Val Leu Gly Leu Ala Ser Gln Asp Ser Leu His Glu Asp Ser Val
    450                 455                 460

Arg Gly Leu Val Lys Leu Ser Ser Val
465                 470

<210> SEQ ID NO 33
<211> LENGTH: 2774
<212> TYPE: DNA
<213> ORGANISM: Human

<400> SEQUENCE: 33
gaaggagtgg acccaacctg gccgcgccgc agaagtggct cccgaggaag ccggcgccgg      60
ggccgccgcc tcgtgtcccc tcggggcgca gtgctcgggg gtcggcgggc cagagccgag     120
gcgcggccgg ggagccgggg gctgcggggc cgagcgggca gccgcgcgag ggggcgggcg     180
ctcggcgacc cggggggccgg ccgggctgag ccccgcgccc cggacgcggg ctggaagcg     240 acggaggagt gctgccgcgg gctgcggacc agcgccgtcc cctcacggag cggggattct     300
gctatgacag ttgggctccc cggagggtta acctgggtgt cctcggcaaa gttgtcgccg     360
agccgggagc ccgtgtaggg gccgcggcgc cgcggctcgg ggggcggccg ggcggccggc     420
ggcggtcgtg gctcggcggg gcccgcgcgg ccgggggggct cctgggggtg tgcgccccca     480
gccggctgcc ctcgtggatg cctcccggcg gcggcgggcc catgaaagac tgcgagtaca     540
gccagatcag cacccacagc tcctccccca tggagtcgcc ccacaagaag aagaaaatcg     600
cggcccggag gaaatgggag tgttcccgg  aagaaacaa gttcttctgt aacgggagga     660
tcatgatggc ccggcagacg ggcgtcttct acctgacgct cgtcctcatc ctggtcacta     720
gcggactctt cttcgccttc gactgtccgt acctggcggt gaaaatcacc cctgccatcc     780
ctgcagtcgc tggcatcctg ttcttctttg tgatggggac cctgctccgc accagcttca     840
gcgaccccgg agtcctccca cgagccacgc ctgatgaagc cgccgatctg aaaggcaaa     900 tagatatcgc aaacggcacc agttcagggg ggtaccgccc gcctcccaga accaaagaag     960
tcatcatcaa tggccagacc gtgaaactta aatactgttt cacctgcaag attttccggc    1020
```

```
cccctcgcgc ctcccattgc agcctttgtg ataactgcgt agaacggttt gatcaccact    1080
gtccctgggt aggcaactgt gtggggaaaa gaaactacag atttttttat atgtttattt    1140
tatctctgtc ttttctgaca gtctttatat ttgcattcgt tatcacccac gtcattcttc    1200
gttcacagca aacaggattc ctaaatgccc ttaaggacag tcctgcaagc gtcctggagg    1260
ctgtggtgtg cttcttctct gtctggtcca tcgttggcct ctcaggattc cacacctact    1320
tgatcagctc caaccagaca acaaatgagg acattaaagg atcctggtca aataaaagag    1380
gtaaagaaaa ttacaatccc tacagctacg gaaatatctt taccaactgc tgtgttgccc    1440
tgtgtgggcc catctcacca agcctgatcg acagaagagg gtacatccag cccgacacgc    1500
cgcagccagc agcaccctcc aatggcatca ccatgtacgg ggccacgcag tcacagagtg    1560
acatggctgc agccacgccc ctgctgcaga gcgagcccag cctcaccagc gacgagctgc    1620
acctgcccgg gaagcctggc ctgggcacgc cctgcgccag cctcacactg ggcccgccca    1680
caccgcccgc ctccatgccc aacctcgccg aggccacgct cgcggacgtg atgccccgga    1740
aagatgagca catgggccac cagttcctga cgcccgatga ggcgccctcg cccccaggc    1800
tactggcggc gggcagcccc ctggcgcaca gccgcaccat gcacgtgctg ggcctggcca    1860
gccaggactc cctgcatgag gactctgtgc gcggcctggt gaagctcagc tccgtgtgac    1920
ccacatggcc ccaggccggg ggacaccaga ggctcctcca tgggcagcag gagtgagcgg    1980
aggggtgtgt cccacagcga cttcccagc caatgccacg gtggagatga cagccccagg    2040
tctggggtac agagaccact taggatggca cagggtggct ggccccggat gctgagagct    2100
tggtttcatt tgaattttct tccccaacct gagtgctttg acaacaatgg aaatagagaa    2160
gtggctgctt tcttttggtg accctccagg ggtggaatcg gagtgtgtct gcccgccctt    2220
gtgacagaca cacggaaggc ttctgacgct tgtggccaga ctgcaattgc acttatgtgt    2280
tatgctacta atatttgaaa cagacctgcc attccatttg ttaattaaaa aaaaaaaaa    2340
tcctaaaggg aaaaaaccga ccaggtgtgg atctgcatgc cacgctgccg tctgtgttac    2400
agtggtgttg ctatttccaa ggaagtgctg ctttcttttt cttttttaa ttttgtgaat    2460
tttcaagtgc tgttttgttg gaagacagtg caacgaactg agactaatgg acagtgtcat    2520
cactcagctt actgggctga ggcgtctgtg gagaggtggc accggggctg cagagggcgg    2580
ctggggttcc gtcgtgtcgg gtgtcacttc accttctgtt tggccgctcg atgaggtctc    2640
gtgttgagat attgtgtgcc acaaccccca cagtcttcac ctccgtgtgt gatgaaactt    2700
cccgtggaca gccaataaaa tgacgtcctc tgttattttg gaaaaaaaaa aaaaaaaaa    2760
aaaaaaaaaa aaaa                                                    2774

<210> SEQ ID NO 34
<211> LENGTH: 337
<212> TYPE: PRT
<213> ORGANISM: Human

<400> SEQUENCE: 34

Met Arg Arg Gly Trp Lys Met Ala Leu Ser Gly Gly Leu Arg Cys Cys
1               5                   10                  15

Arg Arg Val Leu Ser Trp Val Pro Val Leu Ile Val Leu Val Val
            20                  25                  30

Leu Trp Ser Tyr Tyr Ala Tyr Val Phe Glu Leu Cys Leu Val Thr Val
        35                  40                  45

Leu Ser Pro Ala Glu Lys Val Ile Tyr Leu Ile Leu Tyr His Ala Ile
    50                  55                  60
```

-continued

```
Phe Val Phe Phe Thr Trp Thr Tyr Trp Lys Ser Ile Phe Thr Leu Pro
 65                  70                  75                  80

Gln Gln Pro Asn Gln Lys Phe His Leu Ser Tyr Thr Asp Lys Glu Arg
                 85                  90                  95

Tyr Glu Asn Glu Glu Arg Pro Glu Val Gln Lys Gln Met Leu Val Asp
            100                 105                 110

Met Ala Lys Lys Leu Pro Val Tyr Thr Arg Thr Gly Ser Gly Ala Val
        115                 120                 125

Arg Phe Cys Asp Arg Cys His Leu Ile Lys Pro Asp Arg Cys His His
130                 135                 140

Cys Ser Val Cys Ala Met Cys Val Leu Lys Met Asp His His Cys Pro
145                 150                 155                 160

Trp Val Asn Asn Cys Ile Gly Phe Ser Asn Tyr Lys Phe Phe Leu Gln
                165                 170                 175

Phe Leu Ala Tyr Ser Val Leu Tyr Cys Leu Tyr Ile Ala Thr Thr Val
            180                 185                 190

Phe Ser Tyr Phe Ile Lys Tyr Trp Arg Gly Glu Leu Pro Ser Val Arg
        195                 200                 205

Ser Lys Phe His Val Leu Phe Leu Phe Val Ala Cys Met Phe Phe
210                 215                 220

Val Ser Leu Val Ile Leu Phe Gly Tyr His Cys Trp Leu Val Ser Arg
225                 230                 235                 240

Asn Lys Thr Thr Leu Glu Ala Phe Cys Thr Pro Val Phe Thr Ser Gly
                245                 250                 255

Pro Glu Lys Asn Gly Phe Asn Leu Gly Phe Ile Lys Asn Ile Gln Gln
            260                 265                 270

Val Phe Gly Asp Lys Lys Lys Phe Trp Leu Ile Pro Ile Gly Ser Ser
        275                 280                 285

Pro Gly Asp Gly His Ser Phe Pro Met Arg Ser Met Asn Glu Ser Gln
        290                 295                 300

Asn Pro Leu Leu Ala Asn Glu Glu Thr Trp Glu Asp Asn Glu Asp Asp
305                 310                 315                 320

Asn Gln Asp Tyr Pro Glu Gly Ser Ser Ser Leu Ala Val Glu Thr Glu
                325                 330                 335

Thr
```

```
<210> SEQ ID NO 35
<211> LENGTH: 1782
<212> TYPE: DNA
<213> ORGANISM: Human

<400> SEQUENCE: 35
gatcttcgag ccaaagatgc ggcgaggctg aagatggct ctgtctgggg ggctgcggtg      60
ctgccgccgg gtactgtcct gggtgccagt gctcgttatt gtcctcgtcg tgctctggtc     120
ctactatgcc tacgtctttg aactctgcct ggtgactgtt ttgagcccag cagaaaaagt     180
tatttacctc atactctacc atgccatctt tgtgttcttt acctggacct actggaagtc     240
tatctttaca ctcccacagc agccaaacca gaagttccac ttgtcctaca cagacaagga     300
gcgctatgaa aatgaagaaa gacctgaggt ccagaagcag atgcttgttg atatggccaa     360
aaagctaccg gttacacaa gaactggaag tggagctgta cgattctgtg accgtgtca     420 tctgatcaag ccagaccgct gccaccactg ctctgtctgt gctatgtgtg tgttaaaaat     480
ggatcatcac tgcccttggg ttaataactg cattggattt ccaactaca aattcttcct     540 tcaattctta gcttactctg ttctctactg cctgtacatt gctacgacag tcttcagcta     600
```

```
tttcatcaaa tactggagag gggaattacc cagtgttcgc tctaagttcc atgtcctttt      660
tcttctcttt gtggcctgca tgttttttgt cagccttgtg attctctttg gttaccattg      720
ttggcttgtc agcagaaaca aaaccacctt agaggccttc tgcactccag tgtttacaag      780
tggcccagag aaaaatgggt tcaaccttgg cttcatcaag aatatccagc aggtgtttgg      840
agataagaag aagttctggt aataccttat tggttccagc cctggtgatg acactccttt      900
ccctatgagg tctatgaatg agtcacagaa cccactgcta gcaaatgaag aaacctggga      960
agacaacgag gatgacaacc aagattatcc agaaggctca tcatctcttg ctgtggaaac     1020
ggaaacatag cagttttcac atttcctgca tctctcagac aggactcacc atctctgcct     1080
cccatgaggc ttacagagtt caatgttgga aatcattgta atcttcaaaa taagtcaccg     1140
tgttggattg aaagcttcaa aatttgaaag aattccatca aatacttgct gtgtaaatgt     1200
ttctggactt tatgttattt aatttactga ctgaaatcca atttggaatt tggtagcagt     1260
taattcaagc caattttttt tgtttcttca tttcccctcc cccaatccat gaaagcctaa     1320
atgtaaaata tatcttttca ttcatcttat caggtaaaag gaaattcaga aaatttcctt     1380 agagtctttta attcccccac aaagattatt aatcacatat ataggggcctt tttggtgttg    1440 aagggaatca aactacattt gctgcttgtg tgcgtgtgca tttgtgaaca cgtacagcat     1500
atctatacaa aattctgcta tagtgtgaaa atcagggcta aaaacctgaa gcctttgttt     1560
aattatgctt ttcctctaaa tagcaactta aatatttgct agactttgaa tcatcgctat     1620
atcaagtatc taaaatttgg gagggtgaat cagtacactg tgaccaaggt cctcaaattg     1680
gaatttgaac aacaatgtaa aacctgttct gtcacaaatg ttcctgaaag caccacagct     1740
actcaagaag atcaaattca ggacataaac tttattgaac at                       1782
```

<210> SEQ ID NO 36
<211> LENGTH: 377
<212> TYPE: PRT
<213> ORGANISM: Human

<400> SEQUENCE: 36

```
Met Arg Gly Gln Arg Ser Leu Leu Leu Gly Pro Ala Arg Leu Cys Leu
1               5                   10                  15

Arg Leu Leu Leu Leu Gly Tyr Arg Arg Cys Pro Pro Leu Leu
            20                  25                  30

Arg Gly Leu Val Gln Arg Trp Arg Tyr Gly Lys Val Cys Leu Arg Ser
        35                  40                  45

Leu Leu Tyr Asn Ser Phe Gly Gly Ser Asp Thr Ala Val Asp Ala Ala
    50                  55                  60

Phe Glu Pro Val Tyr Trp Leu Val Asp Asn Val Ile Arg Trp Phe Gly
65                  70                  75                  80

Val Val Phe Val Val Leu Val Ile Val Leu Thr Gly Ser Ile Val Ala
                85                  90                  95

Ile Ala Tyr Leu Cys Val Leu Pro Leu Ile Leu Arg Thr Tyr Ser Val
            100                 105                 110

Pro Arg Leu Cys Trp His Phe Phe Tyr Ser His Trp Asn Leu Ile Leu
        115                 120                 125

Ile Val Phe His Tyr Tyr Gln Ala Ile Thr Thr Pro Pro Gly Tyr Pro
    130                 135                 140

Pro Gln Gly Arg Asn Asp Ile Ala Thr Val Ser Ile Cys Lys Lys Cys
145                 150                 155                 160

Ile Tyr Pro Lys Pro Ala Arg Thr His His Cys Ser Ile Cys Asn Arg
```

|     |     |     |     | 165 |     |     |     | 170 |     |     |     | 175 |     |
| --- | --- | --- | --- | --- | --- | --- | --- | --- | --- | --- | --- | --- | --- |
| Cys | Val | Leu | Lys | Met | Asp | His | His | Cys | Pro | Trp | Leu | Asn | Asn | Cys | Val |
|     |     |     | 180 |     |     |     |     | 185 |     |     |     |     | 190 |

Gly His Tyr Asn His Arg Tyr Phe Phe Ser Phe Cys Phe Met Thr
             195                         200                    205

Leu Gly Cys Val Tyr Cys Ser Tyr Gly Ser Trp Asp Leu Phe Arg Glu
     210                    215                    220

Ala Tyr Ala Ala Ile Glu Lys Met Lys Gln Leu Asp Lys Asn Lys Leu
225                  230                  235                  240

Gln Ala Val Ala Asn Gln Thr Tyr His Gln Thr Pro Pro Thr Phe
               245                    250                    255

Ser Phe Arg Glu Arg Met Thr His Lys Ser Leu Val Tyr Leu Trp Phe
     260                    265                    270

Leu Cys Ser Ser Val Ala Leu Ala Leu Gly Ala Leu Thr Val Trp His
         275                  280                  285

Ala Val Leu Ile Ser Arg Gly Glu Thr Ser Ile Glu Arg His Ile Asn
     290                    295                    300

Lys Lys Glu Arg Arg Leu Gln Ala Lys Gly Arg Val Phe Arg Asn
305                  310                  315                  320

Pro Tyr Asn Tyr Gly Cys Leu Asp Asn Trp Lys Val Phe Leu Gly Val
               325                    330                    335

Asp Thr Gly Arg His Trp Leu Thr Arg Val Leu Leu Pro Ser Ser His
         340                  345                  350

Leu Pro His Gly Asn Gly Met Ser Trp Glu Pro Pro Trp Val Thr
               355                    360                  365

Ala His Ser Ala Ser Val Met Ala Val
     370                    375

<210> SEQ ID NO 37
<211> LENGTH: 1816
<212> TYPE: DNA
<213> ORGANISM: Human

<400> SEQUENCE: 37

```
gtgtggttga ggatgggctg gcggcgggtc cgggtccgct gcctggcgct gcgggcggcg     60
ggccatggtg gtttggattg agccgggccc ggccggggcg ccgagtcgga gggggtggca    120
gtgagcggcg gcagaggcta cggggctcgg tttggctgac tggggagtcg gcaggcggca    180
ggaaccatgc gaggccagcg gagcctgctg ctgggcccgg ccgcctctg cctccgcctc    240 cttctgctgc tgggttacag gcgccgctgt ccacctctac tccggggtct agtacagcgc    300
tggcgctacg gcaaggtctg cctgcgctcc ctgctctaca actccttgg gggcagtgac    360 accgctgttg atgctgcctt tgagcctgtc tactggctgg tagacaacgt gatccgctgg    420
tttggagtgg tgttcgtggt cctggtgatc gtgctgacag gctccattgt agctatcgcc    480
tacctgtgtg tcctgcctct catcctccga acctactcag tgccacgact ctgctggcat    540
ttcttctata gccactggaa tctgatcctg attgtcttcc actactacca ggccatcacc    600
actccgcctg ggtacccacc ccagggcagg aatgatatcg ccaccgtctc catctgtaag    660
aagtgcattt accccaagcc agcccgaaca caccactgca gcatctgcaa caggtgtgtg    720
ctgaagatgg atcaccactg ccctggcta aacaattgtg tgggccacta taaccatcgg    780
tacttcttct ctttctgctt tttcatgact ctgggctgtg tctactgcag ctatggaagt    840
tgggaccttt tccgggaggc ttatgctgcc attgagaaaa tgaaacagct cgacaagaac    900
aaactacagg cggttgccaa ccagacttat caccagaccc caccacccac cttctccttt    960
```

```
cgagaaagga tgactcacaa gagtcttgtc tacctctggt tcctgtgcag ttctgtggca    1020
cttgccctgg gtgccctaac tgtatggcat gctgttctca tcagtcgagg tgagactagc    1080
atcgaaaggc acatcaacaa gaaggagaga cgtcggctac aggccaaggg cagagtattt    1140
aggaatcctt acaactacgg ctgcttggac aactggaagg tattcctggg tgtggataca    1200
ggaaggcact ggcttactcg ggtgctctta ccttctagtc acttgcccca tgggaatgga    1260
atgagctggg agcccctcc ctgggtgact gctcactcag cctctgtgat ggcagtgtga    1320
gctggactgt gtcagccacg actcgagcac tcattctgct ccctatgtta tttcaagggc    1380
ctccaagggc agcttttctc agaatccttg atcaaaaaga gccagtgggc ctgccttagg    1440
gtaccatgca ggacaattca aggaccagcc tttttaccac tgcagaagaa agacacaatg    1500
tggagaaatc ttaggactga catccctta ctcaggcaaa cagaagttcc aaccccagac    1560
taggggtcag gcagctagct acctaccttg cccagtgctg acccggacct cctccaggat    1620
acagcactgg agttggccac cacctcttct acttgctgtc tgaaaaaaca cctgactagt    1680
acagctgaga tcttggcttc tcaacagggc aaagatacca ggcctgctgc tgaggtcact    1740
gccacttctc acatgctgct taagggagca caaataaagg tattcgattt ttaaagataa    1800
aaaaaaaaaa aaaaaa                                                    1816

<210> SEQ ID NO 38
<211> LENGTH: 633
<212> TYPE: PRT
<213> ORGANISM: Human

<400> SEQUENCE: 38

Met Gln Arg Glu Glu Gly Phe Asn Thr Lys Met Ala Asp Gly Pro Asp
  1               5                  10                  15

Glu Tyr Asp Thr Glu Ala Gly Cys Val Pro Leu Leu His Pro Glu Glu
                 20                  25                  30

Ile Lys Pro Gln Ser His Phe Asn His Gly Tyr Gly Glu Pro Leu Gly
             35                  40                  45

Arg Lys Thr His Ile Asp Asp Tyr Ser Thr Trp Asp Ile Val Lys Ala
         50                  55                  60

Thr Gln Tyr Gly Ile Tyr Glu Arg Cys Arg Glu Leu Val Glu Ala Gly
 65                  70                  75                  80

Tyr Asp Val Arg Gln Pro Asp Lys Glu Asn Val Thr Leu Leu His Trp
                 85                  90                  95

Ala Ala Ile Asn Asn Arg Ile Asp Leu Val Lys Tyr Tyr Ile Ser Lys
            100                 105                 110

Gly Ala Ile Val Asp Gln Leu Gly Gly Asp Leu Asn Ser Thr Pro Leu
            115                 120                 125

His Trp Ala Thr Arg Gln Gly His Leu Ser Met Val Val Gln Leu Met
        130                 135                 140

Lys Tyr Gly Ala Asp Pro Ser Leu Ile Asp Gly Glu Gly Cys Ser Cys
145                 150                 155                 160

Ile His Leu Ala Ala Gln Phe Gly His Thr Ser Ile Val Val Ala Tyr
                165                 170                 175

Leu Ile Ala Lys Gly Gln Asp Val Asp Met Met Asp Gln Asn Gly Met
            180                 185                 190

Thr Pro Leu Met Trp Ala Ala Tyr Arg Thr His Ser Val Asp Pro Thr
        195                 200                 205

Arg Leu Leu Leu Thr Phe Asn Val Ser Val Asn Leu Gly Asp Lys Tyr
    210                 215                 220
```

```
His Lys Asn Thr Ala Leu His Trp Ala Val Leu Ala Gly Asn Thr Thr
225                 230                 235                 240

Val Ile Ser Leu Leu Leu Glu Ala Gly Ala Asn Val Asp Ala Gln Asn
            245                 250                 255

Ile Lys Gly Glu Ser Ala Leu Asp Leu Ala Lys Gln Arg Lys Asn Val
        260                 265                 270

Trp Met Ile Asn His Leu Gln Glu Ala Arg Gln Ala Lys Gly Tyr Asp
    275                 280                 285

Asn Pro Ser Phe Leu Arg Lys Leu Lys Ala Asp Lys Glu Phe Arg Gln
290                 295                 300

Lys Val Met Leu Gly Thr Pro Phe Leu Val Ile Trp Leu Val Gly Phe
305                 310                 315                 320

Ile Ala Asp Leu Asn Ile Asp Ser Trp Leu Ile Lys Gly Leu Met Tyr
                325                 330                 335

Gly Gly Val Trp Ala Thr Val Gln Phe Leu Ser Lys Ser Phe Phe Asp
            340                 345                 350

His Ser Met His Ser Ala Leu Pro Leu Gly Ile Tyr Leu Ala Thr Lys
        355                 360                 365

Phe Trp Met Tyr Val Thr Trp Phe Phe Trp Phe Asn Asp Leu Asn
    370                 375                 380

Phe Leu Phe Ile His Leu Pro Phe Leu Ala Asn Ser Val Ala Leu Phe
385                 390                 395                 400

Tyr Asn Phe Gly Lys Ser Trp Lys Ser Asp Pro Gly Ile Ile Lys Ala
                405                 410                 415

Thr Glu Glu Gln Lys Lys Lys Thr Ile Val Glu Leu Ala Glu Thr Gly
            420                 425                 430

Ser Leu Asp Leu Ser Ile Phe Cys Ser Thr Cys Leu Ile Arg Lys Pro
        435                 440                 445

Val Arg Ser Lys His Cys Gly Val Cys Asn Arg Cys Ile Ala Lys Phe
    450                 455                 460

Asp His His Cys Pro Trp Val Gly Asn Cys Val Gly Ala Gly Asn His
465                 470                 475                 480

Arg Tyr Phe Met Gly Tyr Leu Phe Phe Leu Leu Phe Met Ile Cys Trp
                485                 490                 495

Met Ile Tyr Gly Cys Ile Ser Tyr Trp Gly Leu His Cys Glu Thr Thr
            500                 505                 510

Tyr Thr Lys Asp Gly Phe Trp Thr Tyr Ile Thr Gln Ile Ala Thr Cys
        515                 520                 525

Ser Pro Trp Met Phe Trp Met Phe Leu Asn Ser Val Phe His Phe Met
    530                 535                 540

Trp Val Ala Val Leu Leu Met Cys Gln Met Tyr Gln Ile Ser Cys Leu
545                 550                 555                 560

Gly Ile Thr Thr Asn Glu Arg Met Asn Ala Arg Arg Tyr Lys His Phe
                565                 570                 575

Lys Val Thr Thr Thr Ser Ile Glu Ser Pro Phe Asn His Gly Cys Val
            580                 585                 590

Arg Asn Ile Ile Asp Phe Phe Glu Phe Arg Cys Cys Gly Leu Phe Arg
        595                 600                 605

Pro Val Ile Val Asp Trp Thr Arg Gln Tyr Thr Ile Glu Tyr Asp Gln
    610                 615                 620

Ile Ser Gly Ser Gly Tyr Gln Leu Val
625                 630
```

<210> SEQ ID NO 39
<211> LENGTH: 5272
<212> TYPE: DNA
<213> ORGANISM: Human

<400> SEQUENCE: 39

| | | | | | |
|---|---|---|---|---|---|
| ttgtatccat | gtttttccgg | gcgtccccg | gagggacagg | ttgcgggtga | ccttttcaag | 60 |
| tgtggaggaa | agggaagctg | cttttgtctt | caggaatgat | gcaggtctcg | actcaagcct | 120 |
| gacgggccca | aacctccctg | gagctggctg | acgactctgc | ccgagttcct | gaagagggt | 180 |
| cccgggggtc | ccggagcgga | agtgggagcg | cgtgggcgtg | ggcctcctcg | gctgcctggg | 240 |
| gctccagact | tgtgctgcgt | gcggctccgg | agctctgttc | tcgctcctga | gcagctgcta | 300 |
| ggtttcccaa | gcgactgtct | caaccgcccg | gccgcctccc | ccgggcagcc | agagcttcac | 360 |
| atctacctcc | agccgggacc | cgcccccgag | ccgcggggcc | cacgcccaga | gccctccgcc | 420 |
| gtccccagcg | cagtgcagca | gagcgcgatc | cagtctgggg | ccgggccgcg | cttccgcgca | 480 |
| cgcgcggaga | aacccgcgcc | ctccgagggg | ggaggggaca | gaggggggcgt | cacggggca | 540 |
| ggagaagaag | gaggaggagg | cccgcgtcgc | ctccggcggg | gctcgcgctc | gccccgcgct | 600 |
| cgccctccgc | ctcgcccgag | ccccgggagg | gtgaaacgct | ttctcccagc | atgcagcggg | 660 |
| aggagggatt | taacaccaag | atggcggacg | gcccggatga | gtacgatacc | gaagcgggct | 720 |
| gcgtgccct | tctccatcca | gaggaaatca | aaccccaaag | ccattttaac | catggatatg | 780 |
| gtgaacctct | tggacggaaa | actcatattg | atgattacag | cacatgggac | atagtcaagg | 840 |
| ctacacaata | tggaatatat | gaacgctgtc | gagaattggt | ggaagcaggt | tatgatgtac | 900 |
| ggcaaccgga | caaagaaaat | gttaccctcc | tccattgggc | tgccatcaat | aacagaatag | 960 |
| atttagtcaa | atactatatt | tcgaaaggtg | ctattgtgga | tcaacttgga | ggggacctga | 1020 |
| attcaactcc | attgcactgg | gccacaagac | aaggccatct | atccatggtt | gtgcaactaa | 1080 |
| tgaaatatgg | tgcagatcct | tcattaattg | atggagaagg | atgtagctgt | attcatctgg | 1140 |
| ctgctcagtt | cggacatacc | tcaattgttg | ttgcttatct | catagcaaaa | ggacaggatg | 1200 |
| tagatatgat | ggatcagaat | ggaatgacgc | ctttaatgtg | ggcagcatat | agaacacata | 1260 |
| gtgtggatcc | aactagattg | cttttaacat | tcaatgtttc | agttaacctt | ggtgacaagt | 1320 |
| atcacaaaaa | cactgctctg | cattgggcag | tgctagcagg | gaataccaca | gtcattagcc | 1380 |
| ttcttctgga | agctggagct | aatgttgatg | cccagaatat | caagggcgaa | tcagcgcttg | 1440 |
| atttggcaaa | acagagaaaa | aatgtgtgga | tgatcaacca | cttacaagag | gcaaggcaag | 1500 |
| caaaaggata | tgacaatccg | tccttcctta | gaaagctgaa | agctgataag | gaatttcggc | 1560 |
| agaaagtaat | gttaggaact | ccttttcctag | ttatttggct | ggttgggttt | atagcagacc | 1620 |
| taaatattga | ttcttggctc | attaaagggc | taatgtatgg | tggtgtttgg | gctacagtac | 1680 |
| agtttctttc | aaaatccttt | ttcgatcatt | caatgcatag | tgcattgccc | cttgggatat | 1740 |
| atttggcaac | caaattctgg | atgtatgtga | cgtggttctt | ctggtttggg | aatgatctca | 1800 |
| acttttatt | tatccatctt | ccattccttg | ccaatagtgt | tgcactttc | tacaattttg | 1860 |
| gaaaatcttg | gaaatcagat | ccagggatta | ttaaagcaac | agaagagcaa | agaaaaaga | 1920 |
| caatagttga | acttgcagag | acaggaagtc | tggacctcag | tatattctgc | agtacctgtt | 1980 |
| tgatacgaaa | accggtgagg | tccaaacatt | gtggtgtgtg | caaccgctgt | atagcaaaat | 2040 |
| ttgatcatca | ttgcccatgg | gtgggtaact | gtgtaggtgc | aggcaaccat | agatatttta | 2100 |
| tgggctacct | attcttcttg | cttttttatga | tctgctggat | gatttatggt | tgtatatctt | 2160 |
| actgggggact | ccactgtgag | accacttaca | ccaaggatgg | attttggaca | tacattactc | 2220 |

```
agattgccac gtgttcacct tggatgtttt ggatgttcct gaacagtgtt ttccacttca    2280
tgtgggtggc tgtattactc atgtgtcaga tgtaccagat atcatgttta ggtattacta    2340
caaatgaaag aatgaatgcc aggagataca agcactttaa agtcacaaca acgtctattg    2400
aaagcccatt caaccatgga tgtgtaagaa atattataga cttctttgaa tttcgatgct    2460
gtggcctctt tcgtcctgtt atcgtggact ggaccaggca gtatacaata gaatatgacc    2520
aaatatcagg atctgggtac cagctggtgt agcaacatct tatcctatga agcatattgc    2580
tgagtggtgc ctgaaaattg tgtctgtccg tgtctttctc acactcgaat ccacatcctt    2640
tgaacaagag catgctatgt gtagggctaa tggtgaattt tacagtcttc ttttcaacac    2700
ttttattaac aaaagtaaac atggacagaa cacactgcca tttctgggaa gagtaaagat    2760
gataaaaaat aattttaatg gttcttaatg tggaaattca caacatactc aacttttggg    2820
ttttgttctc acagtatttt tcacaaaaaa agggtaaact tattctattg acagacatgg    2880
tgtactgatc agaaatgttc agttttaact aaaactaaat ttatgttatt tggctaaatg    2940
ttatgatgca gtctagtacg agtattgcat ctaattccag gagcatcgtt ttaagttgat    3000
tgactagtta ttatgtacat ttcagaatgt acacataaat actgtgatga aaatcatgtg    3060
attgggatct actgtgatgt tgtcttcaaa ggcaggagaa aataatgttc acaataaaat    3120
gtgctaacaa tgttttgttt ctatcagctg ttgcaatgct gatatatttc tagttcagtg    3180
aaataatttg tagtaacctt actctgaggt tttacggtct gataatgaag cacttgcatg    3240
agtatagtaa gtcatgtttt tttgttcaaa tttaaaagcc ctgctaattg catgacacac    3300
cacatagaat gtatactagc agatactatc cagtgaagca taaattagaa tttaatttga    3360
tgttcaaaaa cagttccatt tttaagggtt aaggtggtat tttcaagaaa aggcagaaca    3420
aataatgcaa aattctcagt aatagtgata catggatata cttccttta aattctcagc    3480 tgcaaaataa ttgtagacaa aataatgcca tttaactaaa gatggagcat gatctgtgta    3540
catagcacat gtgaataaaa gaaaagctga cagtatattc tggtttcaat aaaatgacct    3600
atcagaaagt agaatttcat ccccaagagt atttcagttt atccaatatt gagtaagttc    3660
tgaaacagtt ttagaaaaaa ttttctttt gttaaatgtg atgcactgat caattttgt    3720 cacagcattt tcataccttc atggtggact actagtcact gcttccataa atattgttta    3780
cagggtgaga tttggtttat tcatcttaag tgctgtagca aactgtggtt cgagcaacct    3840
gtgggaaatc tgtgagaggg aatggggtgg gagatgtggg ggaatggtgg tcagactgat    3900
gacagatcct agaccaatgt aaagaatgtg tatctgtata taaataattt atcaaatagt    3960
tttctctttg tgtctgtgtt agtgttttta aagctgctca tttcattttg tccaaccaaa    4020
aagaaaaggg agataactaa tgagcttcta gtgatgttca aaattgctgt taataggcat    4080
tataccctgc aagttcactg catgtctgat gcttggtaaa actagtcttc cctgtaaaat    4140
gcagattaca ggtattaaag caatctagtg gtatacccgc cccttgcctt agtaagagga    4200
gcagtgaaat gtatatagtt gatgttcagt atttccaagt accatttta tatagtagct    4260 tatttgacca taagtcacac atcaaaaaaa gattacccct agtgtatgtg ttttaatatt    4320
agaaaattgg catatgtact ttattttga aagggaaga gatgggtgtg gggtggcaat    4380
agcattgtgc cattttgtca tagaatgtaa aaattggtta actttacaaa tgtcagctag    4440
ttttgactac taattggggg aaattttaga taatttttaa attcaaagtt atttataaaa    4500
tgctagaatt tgttttaatt ttttgtattt tgagccactt cacatgaaga ctcagttgca    4560
tttttatcga atacattttt atcaaccagt taaagactat ggtggttttt tcagagtttg    4620
```

-continued

```
gctaagaatg ttgttaccat cttctttgtt tgtggtacaa tattttcagt gcaaaagaga    4680
tgtcattcag ttaaaaagac aaacctctag atgtgtaatt acatggaaaa tactagcaat    4740
gtgaatgctt ttgtagtaac catcttgtag tacctgtgaa atctataact cagaaatggt    4800
cagatggtca ggagccagct atgcagcagt ataccatctg tttaattatt ttgtaggtcc    4860
tgtgtgtgga accaactata aacccagttc taaagttgtg tatgatggtg aacctttggg    4920
aatagttctt atcaacttaa ttggatactt ttagcaaata ggaacttaat tctcagcact    4980
gaacatgaat tacttccttg gagttttttt cattcatatt tttgttgttt ccaggaattt    5040
atttgatatt aatgggcgta aaacagcatc attgtactta agctatggat gttttttattt    5100 tatattttct ttatttataa ctgtgccaag tattattttg ctacttaccg tgttattctg    5160
tggaaagaaa aacctgtaaa gtgtttaata aattagccct ccttacataa attaaatgtc    5220
aaaattttgt aaaatattaa tcagaataaa tactgactct taaaaaaaaa aa            5272
```

<210> SEQ ID NO 40
<211> LENGTH: 388
<212> TYPE: PRT
<213> ORGANISM: Human

<400> SEQUENCE: 40

```
Met Lys Asp Cys Glu Tyr Gln Gln Ile Ser Pro Gly Ala Ala Pro Leu
1               5                   10                  15

Pro Ala Ser Pro Gly Ala Arg Arg Pro Gly Pro Ala Ala Ser Pro Thr
            20                  25                  30

Pro Gly Pro Gly Pro Ala Pro Pro Ala Pro Ala Pro Pro Arg Trp
        35                  40                  45

Ser Ser Ser Gly Ser Gly Ser Gly Ser Gly Ser Leu Gly Arg
    50                  55                  60

Arg Pro Arg Arg Lys Trp Glu Val Phe Pro Gly Arg Asn Arg Phe Tyr
65                  70                  75                  80

Cys Gly Gly Arg Leu Met Leu Ala Gly His Gly Gly Val Phe Ala Leu
                85                  90                  95

Thr Leu Leu Leu Ile Leu Thr Thr Thr Gly Leu Phe Phe Val Phe Asp
            100                 105                 110

Cys Pro Tyr Leu Ala Arg Lys Leu Thr Leu Ala Ile Pro Ile Ile Ala
        115                 120                 125

Ala Ile Leu Phe Phe Phe Val Met Ser Cys Leu Leu Gln Thr Ser Phe
    130                 135                 140

Thr Asp Pro Gly Ile Leu Pro Arg Ala Thr Val Cys Glu Ala Ala Ala
145                 150                 155                 160

Leu Glu Lys Gln Ile Asp Asn Thr Gly Ser Ser Thr Tyr Arg Pro Pro
                165                 170                 175

Pro Arg Thr Arg Glu Val Leu Ile Asn Gly Gln Met Val Lys Leu Lys
            180                 185                 190

Tyr Cys Phe Thr Cys Lys Met Phe Arg Pro Pro Arg Thr Ser His Cys
        195                 200                 205

Ser Val Cys Asp Asn Cys Val Glu Arg Phe Asp His His Cys Pro Trp
    210                 215                 220

Val Gly Asn Cys Val Gly Arg Arg Asn Tyr Arg Phe Phe Tyr Ala Phe
225                 230                 235                 240

Ile Leu Ser Leu Ser Phe Leu Thr Ala Phe Ile Phe Ala Cys Val Val
                245                 250                 255

Thr His Leu Thr Leu Arg Ala Gln Gly Ser Asn Phe Leu Ser Thr Leu
```

```
                      260                 265                 270
Lys Glu Thr Pro Ala Ser Val Leu Glu Leu Val Ile Cys Phe Phe Ser
              275                 280                 285

Ile Trp Ser Ile Leu Gly Leu Ser Gly Phe His Thr Tyr Leu Val Ala
          290                 295                 300

Ser Asn Leu Thr Thr Asn Glu Asp Ile Lys Gly Ser Trp Ser Lys
305                 310                 315                 320

Arg Gly Gly Glu Ala Ser Val Asn Pro Tyr Ser His Lys Ser Ile Ile
                  325                 330                 335

Thr Asn Cys Cys Ala Val Leu Cys Gly Pro Leu Pro Pro Ser Leu Ile
              340                 345                 350

Asp Arg Arg Gly Phe Val Gln Ser Asp Thr Val Leu Pro Ser Pro Ile
              355                 360                 365

Arg Ser Asp Glu Pro Ala Cys Arg Ala Lys Pro Asp Ala Ser Met Val
      370                 375                 380

Gly Gly His Pro
385

<210> SEQ ID NO 41
<211> LENGTH: 3163
<212> TYPE: DNA
<213> ORGANISM: Human

<400> SEQUENCE: 41
gcgcgcgccg ccgctgccac ctccgctgct cggcccggtc ccggagtggc ccggccggcc     60
cgcggggcgc ggagccgagg cccgcggctg gctgcatgaa ggactgcgag taccagcaga    120
tcagccccgg ggccgccccg ctgccccgcct ccccgggggc gcgccgtccc ggccccgccg    180
cgtccccgac tccgggcccc gggcccgcgc cgcccgccgc ccccgccccg ccgcgctgga    240
gcagcagcgg cagcggcagc ggcagcggga gcgggagcct cggccgccgc ccacggcgca    300
agtgggaggt gttcccgggt cgcaatcgct tctactgcgg cggccgcctc atgctggccg    360
gccacggcgg cgtcttcgcg ctcacgctgc tgctcatcct caccaccacc ggcctcttct    420
tcgtctttga ctgtccctac ctggctcgca agctgacccc tgccatcccc atcatcgctg    480
ccatcctctt cttcttcgtc atgagctgcc tgctgcagac aagcttcacc gaccctggga    540
tcctgccccg ggccactgtc tgtgaagcag ccgccctgga aaacagatc gacaacacag    600 gcagttctac ataccggcca ccccctcgga cccgggaggt gctgatcaac gggcagatgg    660
tgaagctgaa gtactgcttc acctgcaaga tgttccggcc accccgaacc tcacactgca    720
gtgtctgcga caactgtgtg aacgatttg accatcactg ccccctgggtg ggcaactgtg    780 tggggagacg gaactatcgc ttcttctacg cgtttattct ctccctctca ttcctgacgg    840
ccttcatctt cgcctgtgtg gtcacccacc tgacgttgcg cgctcaggga agcaacttcc    900
tctccactct gaaggagaca ccagcaagcg tgctggagtt ggtgatctgc ttcttctcca    960
tctggtccat tctgggcctc tcagggtttc acacgtacct cgtcgcctcc aacctgacta   1020
ctaatgaaga catcaaaggc tcgtggtcca gcaagagggg cggtgaggcc tctgtcaacc   1080
cctacagcca taaaagtatt atcaccaact gctgtgctgt gctctgtggc ccctacctc   1140 ccagcctaat tgaccggagg ggatttgtgc agtccgacac cgtgttgccc tcacccatca   1200
gaagcgatga gccagcctgc agagccaagc ctgatgccag catggtagga ggccacccct   1260
gaccacggct cagtacttgc cacctgctgg cctgtctgac cctccgcact cacctgccgg   1320
gaccctccct attccatcca agggaagcag aactgccaaa gactcaagtc ttttcatatt   1380
```

-continued

```
tatttcccat cctgcgtggc tttccctgaa ctgttccgtg gctgtgccct ctgctcccca    1440
aacccaggtt cccacagcct tgggccctag gtacccagc tgatcagtgc caggagagac    1500
cagagcctct ggaggctacc caggggacca caccaagtcc ttgcctgtgc cgggcgagcc    1560
ctgtgtgagt gaggctgtga actgagcgtg aggcctccca ggtgggggaa ctgcttgggc    1620
cttgctgagc cagggtcctc agggtgaagc aggactgagg agtggccagc tctggatagc    1680
tggctgtgga gaggaagcct ccatgggctg ctttggtctg tgggctcctt cattcccttg    1740
gtgataattt cccttcttc tgtgggattt ttggtggggt ttccccccct tttttatgga    1800
gttggccaat aggattgagt tggggctcca gtagagaagg cagggttggt ggtgggtggg    1860
ggcagcctgt atcagacaaa ggtaaatcag ccagccaggc acccacagcc tcagctcctg    1920
tgcagttcct gggcagcaca gtggaagtgg gagcctggtc cttcccctgc ccatggagag    1980
ctctttaagg gatcccagcc tgccctcca cttctctccc aagccaggtc ccggcatggg    2040
tgggttatgc tcatgctggc aatacttgaa acgggtttat taatgctggg tattttgcac    2100
aattttatag acctctttc tacatagtct tttttaaatg gaaggagaaa atgtcagcca    2160
cattactgtc tgtgtagtgc caggtgaagg gttatcagaa ggctggttgg tttaataag    2220 tttattccaa gagaccttct ggctggaatg agtgagagtg tgtgtgcatg tgtgtgtgtg    2280
ttcatgtgtg ccctgtatga atgtggctgg ctcccatatc ccctgggctg ccccctgccc    2340 catcccttt gagtatcaga agcactctga gccaagggga caggggcac gtgcactggt    2400 cacgagaaaa ccctgggctc ccactggggc tcagcccagc ctcctatctt tccttcttct    2460
atggacttca gacagccagt gtctggggac tctgccactc tacccccagc cctacccacc    2520 agccccagg tgaggcttcc agctgggacc tgcccagaca ggctgagcct gggcgtggtg    2580
ggtggggtga tggctctggg gagcggctgc catcctacaa gccacacccc ctcctctgag    2640
ctctgaatat gggacccagt gccaggagct ggaagacaag gtgtttctgc caaacgggga    2700
cctccatcca gagaaaagga agaaggtgca gggtgggcca agaggcaagt gaaggttggc    2760
ctgagtctgg gccggaaact cagaggatgt ttctcctctg ctgggagctg tagttttctta    2820 tcaaaataga tattgttcca ccatcccct ccttggccct tcaagtgggc tgaagccctt    2880
ggaaagtgac ataggaagtc cccagatctt gcccttctca ctccagaggc tagtggtcac    2940
agacagctgg gaatggcagc cacagagggt ccctctggg agaaacagct tcacccagc    3000 ctcagggccc tgggccatca ctgcagtggc cctgggaggt gaggaagaag ctggctagag    3060 gaggggctc ccacctacct tttattaag ccagtattct ttgttcctgc ttgtaataaa    3120
acttcagttt ataagaaaaa aaaaagaaa aaaaaaaaaa aaa                      3163
```

<210> SEQ ID NO 42
<211> LENGTH: 282
<212> TYPE: PRT
<213> ORGANISM: Human

<400> SEQUENCE: 42

```
Met Thr Leu Leu Thr Asp Ala Thr Pro Leu Val Lys Glu Pro His Pro
1               5                   10                  15

Leu Pro Leu Val Pro Arg Pro Trp Phe Leu Pro Ser Leu Phe Ala Ala
                20                  25                  30

Phe Asn Val Val Leu Leu Val Phe Ser Gly Leu Phe Ala Phe
                35                  40                  45

Pro Cys Arg Trp Leu Ala Gln Asn Gly Glu Trp Ala Phe Pro Val Ile
    50                  55                  60
```

```
Thr Gly Ser Leu Phe Val Leu Thr Phe Phe Ser Leu Val Ser Leu Asn
 65                  70                  75                  80

Phe Ser Asp Pro Gly Ile Leu His Gln Gly Ser Ala Glu Gln Gly Pro
                 85                  90                  95

Leu Thr Val His Val Val Trp Val Asn His Gly Ala Phe Arg Leu Gln
            100                 105                 110

Trp Cys Pro Lys Cys Cys Phe His Arg Pro Pro Arg Thr Tyr His Cys
        115                 120                 125

Pro Trp Cys Asn Ile Cys Val Glu Asp Phe Asp His His Cys Lys Trp
    130                 135                 140

Val Asn Asn Cys Ile Gly His Arg Asn Phe Arg Phe Phe Met Leu Leu
145                 150                 155                 160

Val Leu Ser Leu Cys Leu Tyr Ser Gly Ala Met Leu Val Thr Cys Leu
                165                 170                 175

Ile Phe Leu Val Arg Thr Thr His Leu Pro Phe Ser Thr Asp Lys Ala
            180                 185                 190

Ile Ala Ile Val Val Ala Val Ser Ala Ala Gly Leu Leu Val Pro Leu
        195                 200                 205

Ser Leu Leu Leu Leu Ile Gln Ala Leu Ser Val Ser Ser Ala Asp Arg
    210                 215                 220

Thr Tyr Lys Gly Lys Cys Arg His Leu Gln Gly Tyr Asn Pro Phe Asp
225                 230                 235                 240

Gln Gly Cys Ala Ser Asn Trp Tyr Leu Thr Ile Cys Ala Pro Leu Gly
                245                 250                 255

Pro Lys Ala Ala Ala Ser Trp Met Arg Leu Ala Ser Ala Ser Cys Arg
            260                 265                 270

Ala Lys Pro Trp Ala Val Cys Phe Pro Ser
        275                 280

<210> SEQ ID NO 43
<211> LENGTH: 1315
<212> TYPE: DNA
<213> ORGANISM: Human

<400> SEQUENCE: 43
ctttcaccct gggctgcggc tctgaggctg ccgtggccat ggagctctgg aagctgggct     60 ggggaggaa gcctggtggc tctgacctcc cctggaggcg aaggaggccc agccatgaca    120
ctcttaacgg atgccacgcc gctggtgaag gagcccatc ccctgcctct ggtcccacgt    180
ccctggttcc tccctagcct ctttgctgcc ttcaatgtgg tgctgctggt cttttttcagt   240 ggcctcttct tcgcattccc ttgcaggtgg ctggctcaga acggggagtg ggcctttcct    300
gttatcacag gctccctctt tgtccttacc ttcttcagtc ttgtttcact caacttctca    360
gaccctggca tcttacatca aggctccgct gagcagggcc ccttgacggt gcacgtggtg    420
tgggtgaacc acggggcctt ccgcctgcaa tggtgtccaa agtgctgctt ccaccgcccg    480
ccccggactt accactgccc ctggtgcaac atctgtgtgg aggactttga ccaccactgc    540
aagtgggtca taactgcat cggtcaccgc aacttccgct tcttcatgct gcttgtcctg    600
tccctgtgcc tctactcggg cgccatgctg gtcacctgtc tcatcttcct ggtgcgcaca    660
acccacctgc cttctccac cgacaaggcc atcgccatcg tggtggccgt gtccgccgcg    720
ggcctcctgg tgccgctgtc cctcctgctg ctgatccagg cactgtccgt gagctcggcc    780
gaccgcacct acaagggcaa gtgcagacac cttcagggat acaacccctt cgaccagggc    840
tgtgccagca actggtattt aacaatttgt gcaccactgg gacccaaggc tgctgcatcc    900
```

-continued

```
tggatgaggc tggcctcagc ttcctgcaga gctaagccct gggccgtgtg cttcccaagc    960
tgaggcgggc aggggagccg gaccaggag  acggtggcc  cctgcatctg gcctgctgct   1020
ccccagttcc acacgggccc agtgctgccc ctgctgctgc aggagccccc aggcgaggtt   1080
cggccttcct ctcgcccctg tgcacccgga gatgcccaca gcaccagcac ctgagctcac   1140
ctccgaaccc gcctcctgaa cccgcctcct gaacctgcct ccttacctcc cacttcctga   1200
gccctgagtg gaagcttttc tgtgccttgc cctttgccca ctcccctggt gggactgcca   1260
agaccctcaa tgcccattaa atactcttgc ctgcctctca aaaaaaaaaa aaaaa         1315
```

<210> SEQ ID NO 44
<211> LENGTH: 354
<212> TYPE: PRT
<213> ORGANISM: Human

<400> SEQUENCE: 44

```
Met Ala Pro Trp Thr Leu Trp Arg Cys Cys Gln Arg Val Val Gly Trp
1               5                   10                  15

Val Pro Val Leu Phe Ile Thr Phe Val Val Trp Ser Tyr Tyr Ala
            20                  25                  30

Tyr Val Glu Leu Cys Val Phe Thr Ile Phe Gly Asn Glu Glu Asn
        35                  40                  45

Gly Lys Thr Val Val Tyr Leu Val Ala Phe His Leu Phe Phe Val Met
    50                  55                  60

Phe Val Trp Ser Tyr Trp Met Thr Ile Phe Thr Ser Pro Ala Ser Pro
65                  70                  75                  80

Ser Lys Glu Phe Tyr Leu Ser Asn Ser Glu Lys Glu Arg Tyr Glu Lys
                85                  90                  95

Glu Phe Ser Gln Glu Arg Gln Gln Glu Ile Leu Arg Arg Ala Ala Arg
            100                 105                 110

Ala Leu Pro Ile Tyr Thr Thr Ser Ala Ser Lys Thr Ile Arg Tyr Cys
        115                 120                 125

Glu Lys Cys Gln Leu Ile Lys Pro Asp Arg Ala His His Cys Ser Ala
    130                 135                 140

Cys Asp Ser Cys Ile Leu Lys Met Asp His His Cys Pro Trp Val Asn
145                 150                 155                 160

Asn Cys Val Gly Phe Ser Asn Tyr Lys Phe Phe Leu Leu Phe Leu Leu
                165                 170                 175

Tyr Ser Leu Leu Tyr Cys Leu Phe Val Ala Ala Thr Val Leu Glu Tyr
            180                 185                 190

Phe Ile Lys Phe Trp Thr Asn Glu Leu Thr Asp Thr Arg Ala Lys Phe
        195                 200                 205

His Val Leu Phe Leu Phe Phe Val Ser Ala Met Phe Phe Ile Ser Val
    210                 215                 220

Leu Ser Leu Phe Ser Tyr His Cys Trp Leu Val Gly Lys Asn Arg Thr
225                 230                 235                 240

Thr Ile Glu Ser Phe Arg Ala Pro Thr Phe Ser Tyr Gly Pro Asp Gly
                245                 250                 255

Asn Gly Phe Ser Leu Gly Cys Ser Lys Asn Trp Arg Gln Val Phe Gly
            260                 265                 270

Asp Glu Lys Lys Tyr Trp Leu Leu Pro Ile Phe Ser Ser Leu Gly Asp
        275                 280                 285

Gly Cys Ser Phe Pro Thr Arg Leu Val Gly Met Asp Pro Glu Gln Ala
    290                 295                 300

Ser Val Thr Asn Gln Asn Glu Tyr Ala Arg Ser Gly Ser Asn Gln Pro
```

```
                305                 310                 315                 320
Phe Pro Ile Lys Pro Leu Ser Glu Ser Lys Asn Arg Leu Leu Asp Ser
                325                 330                 335
Glu Ser Gln Trp Leu Glu Asn Gly Ala Glu Glu Gly Ile Val Lys Ser
            340                 345                 350
Gly Val

<210> SEQ ID NO 45
<211> LENGTH: 1514
<212> TYPE: DNA
<213> ORGANISM: Human

<400> SEQUENCE: 45
cggaggcggg ggagctggac cagcagccgc ctggagcgtc cgagtcaccg tcgccggggc      60
tcccgcgctc cccagaacgg tgggacgcgg ggctcggcag ccgccagcgg aacatggcgc     120
cctggacgct gtggcgctgc tgccagcgcg tcgtgggctg ggtgccggtg ctcttcatca     180
ccttcgtggt cgtctggtcc tactacgcgt acgtggtgga gctctgcgtg tttactattt     240
ttggaaatga agaaaatgga aagaccgttg tttaccttgt ggctttccat ctgttctttg     300
ttatgtttgt atggtcctat ggatgacaa ttttcacatc tcccgcttcc ccctccaaag      360
agttctactt gtccaattct gaaaaggaac gttatgaaaa agaattcagc caagaaagac     420
aacaagaaat tttgagaaga gcagcaagag ctttacctat ctataccaca tcagcttcaa     480
aaactatcag atattgtgaa aaatgtcagc tgattaaacc tgatcgggcg catcactgct     540
cagcctgtga ctcatgtatt cttaagatgg atcatcactg tccttgggtg aataactgtg     600
tgggattttc taattacaaa ttcttcctgc tgtttttatt gtattcccta ttatattgcc     660
ttttcgtggc tgcaacagtt ttagagtact ttataaaatt ttggacgaat gaactgacag     720
atacacgtgc aaaattccac gtactttttc ttttctttgt gtctgcaatg ttcttcatca     780
gcgtcctctc acttttcagc taccactgct ggctagttga aaaaaataga acaacaatag     840
aatcattccg cgcacccacg ttttcatacg gacctgatgg aaatggtttc tctcttggat     900
gcagtaaaaa ttggagacaa gtctttggtg atgaaaagaa atattggcta cttccaatat     960
tttcaagctt gggtgatggt tgcagttttc caactcgcct tgtggggatg gatccagaac    1020
aagcttctgt tacaaaccag aatgagtatg ccagaagtgg ctcaaatcaa ccttttccta    1080
tcaaaccact tagtgaatca aaaaaccgct tgttggacag tgaatctcag tggctggaga    1140
atggagctga agaaggcatc gtcaaatcag gtgtatgaaa acattataga ctggtatttt    1200
caattttcat ttgcaagaaa atgatcagtg gaatgaaata actgaagtat aacagaagat    1260 atattttta aaacggaaag cctttgtaca gttcctggga ttcacagaag cactactcca     1320
gagcagaatg atgcccttaat cttaagtgtc catttgtgca gcattgactt agagctacaa    1380
aagtgactta atgttattct ggaaataata cttacctgtt atgagttgct ataatatgag     1440
ctgtcatcac attttaaaaa aaaaaaaaaa aaaaaaaaaa aaaaaaaaaa aaaaaaaaaa    1500
aaaaaaaaaa aaaa                                                      1514

<210> SEQ ID NO 46
<211> LENGTH: 3267
<212> TYPE: DNA
<213> ORGANISM: Human

<400> SEQUENCE: 46
ttccgtcgcg gctcccggga gctaagcgag acggcgacgg cggcagtcgt ccctccccac      60
```

-continued

```
gcgggcgcgc gggcatgcgg acacccactc ggccggtcca ggccctcagg ctcccggaag    120
cggaagggga gagcggcccg gcctgggcgg cggcgccgga ggaggcggag gtggcgcggc    180
aggaggaggg gaaagagctg ctggtggtcg ggagagcggc ggcagcgaga ggcgagccag    240
cggcgacgaa tgaagaactt tttcacttac tgcaggattt tcagcttcag caagcaggtt    300
ctcatggaga actgttattg aagagagatc catttggtgg gatataatta aaaaaaatga    360
atcaaaagaa aatctctaaa tgcagattcc agaaaaatta cagcacatct cagtgaattt    420
gcaagtggat catccttcct tgtgggttag caggcagtta taagattgca aaatgggtct    480
ccggattcac tttgttgttg acccacatgg ttggtgctgc atgggtttga ttgtctttgt    540
ttggttatac aatattgttt taattcccaa aattgtcctc tttcctcact atgaagaagg    600
acatattcca ggcatattaa taataatatt ctatggcatt tccatattct gtctggttgc    660
cttagtgagg gcctccataa ctgatccagg aagactccct gagaacccca agatcccaca    720
tggagaaagg gagttctggg aattatgtaa caagtgtaat ttgatgagac caaagcgttc    780
ccatcactgc agccgctgcg gccactgtgt gaggagaatg gatcatcact gtccatggat    840
taacaattgt gttggtgaag ataatcattg gctctttctg cagttgtgtt tctacactga    900
acttcttact tgctacgcac tgatgttttc tttctgccac tattactatt ttcttccact    960
aaaaaagcgt aatttggacc tctttgtttt tagacatgaa ttggccataa tgagactagc    1020
agcctttatg ggcattacta tgttagttgg aataactgga ctcttttaca ctcaactaat    1080
tggcatcatc acagatacaa catctattga aaagatgtca aactgttgtg aagatatatc    1140
gaggccccga aagccatggc agcagacctt ctcagaagtt tttggcactc gttggaagat    1200
cctgtggttc attcctttca ggcagaggca accactgcga gttccctacc actttgccaa    1260
tcatgtctaa acagatggat ggtgggcaca gatgggtcct ccatgctggc aatgcgttac    1320
aggttttatg ataatagaac tatgacagtc ttcaagtcaa ttaaaatcca cccaccaatc    1380
ttaggcatca taatgtgccc caggctttat tttaatagtg atcttgatcc tgttgtggga    1440
ctaatacaag atctatattt aagttttaaa gcatgtttac tttcaaatta gctttccaca    1500
gggatttctt gaaatgcttt tgttattaaa ctcaaaaggc agtgattagg atgaaataat    1560
tgtacataat ttattttagt actgacagtg ttacagattc taatttatgg taaatttcag    1620
atgtttattt aaaattttca cttttaaaca gtaaccaaat ctaaatttaa ttattcaggt    1680
tttacaaaag ttgatacacc ttcttatagt ataggtaaat tttcttttc aaatccaatt    1740 taaaataacc tttcctttta aatgtgctgc aacgttttta aaaatgcagc agcataggag    1800
tgaacaacag caacacaaaa cgggcattgg tttcttagga gtggcttgct tacgttttct    1860
tcttttttct tcaccaaaac caacatgaaa gtaccactga agtaaaacac caactaccta    1920
ccttactata aaggaaatgt taaaattttt ttcacaataa tttttcaat tttcactatt    1980 actgttgtaa ttattgattg tgattaaaat atttgctccc aggagaactc ctgaccagtg    2040
ggcatgtatt cctattttat cctaagattt taatgagcaa aaggggaga gaatttgcaa    2100 taacttcaca attccttttt ctagtgcagt tatattagaa tgcatatgtt tttaaaatgc    2160
tagtataact agatagtata taatgtacag tataaagagg aatattgtgc ttttgaaaag    2220
agtatacttt ttactttat ttatgtacta gtagatgtaa aatttcgcat tgaaggttta    2280
tatatattgg ccaactcata tagaaatttt atttatagga agctactact aaaaaaagtc    2340
actaactttg tgtacctata atccctaaat taaaattaaa ttttaattgg ctggctgtaa    2400
tttgcattga gagacctttt actagtagct agtgttagga agtgaaccta aaataagaaa    2460
```

-continued

| | |
|---|---|
| atataatgat ctgtgtttat cattagcctt gtacaaatgt aaattactaa tagtgatgtt | 2520 |
| cttttgcaag gcatagaaca tttgtatgaa aagacattta gtatgctttg aaaaaaactc | 2580 |
| agcttttagt ttttttccat tagaatactg caaaacccat atatctttt aaaaaattta | 2640 |
| tgtactcaca gtctttccct tgaagagaag attgaaaaag tctactgttc ataaaccatg | 2700 |
| ctaacatttt ccttttagct agttttgaaa gtaaggaaca atacctggga aataataaaa | 2760 |
| cagaaggtta ccattgtcag ccagttggct atactgtggt tagttctttc agaaattgta | 2820 |
| aatatcttgt agcatattct gaaataatag agtaagttct tctcagagat gttaatatca | 2880 |
| tgttttcat gttctaatta gaatacttta ttacttacaa actcagaaat acgaacagaa | 2940 |
| atacagcaga cgaacatatt tattggtact gaaaagagat gtagtaaatt aaatagaaga | 3000 |
| aatatattta taaagcttag tgaaacacaa aattagaatg ttcatgtcag gcacaagggt | 3060 |
| ttggattttg tgcaagctaa tttggccaca tttggcctgg tgacagaact gttcataagg | 3120 |
| aagtaatata tagataaggt aggtagatat cagttgaatg cctatatttg tatacattcc | 3180 |
| tttcaaataa agaccttgag aaaacaaaaa aaaaaaaaa aaaaaaaaaa aaaaaaaaa | 3240 |
| aaaaaaaaaa acaaaaaaaa aaaaaa | 3267 |

<210> SEQ ID NO 47
<211> LENGTH: 3267
<212> TYPE: DNA
<213> ORGANISM: Human

<400> SEQUENCE: 47

| | |
|---|---|
| ttccgtcgcg gctcccggga gctaagcgag acggcgacgg cggcagtcgt ccctccccac | 60 |
| gcgggcgcgc gggcatgcgg acacccactc ggccggtcca ggccctcagg ctcccggaag | 120 |
| cggaagggga gagcggcccg gcctgggcgg cggcgccgga ggaggcggag gtggcgcggc | 180 |
| aggaggaggg gaaagagctg ctggtggtcg ggagagcggc ggcagcgaga ggcgagccag | 240 |
| cggcgacgaa tgaagaactt tttcacttac tgcaggattt tcagcttcag caagcaggtt | 300 |
| ctcatggaga actgttattg aagagagatc catttggtgg gatataatta aaaaaaatga | 360 |
| atcaaaagaa aatctctaaa tgcagattcc agaaaaatta cagcacatct cagtgaattt | 420 |
| gcaagtggat catccttcct tgtgggttag caggcagtta taagattgca aaatgggtct | 480 |
| ccggattcac tttgttgttg acccacatgg ttggtgctgc atgggtttga ttgtctttgt | 540 |
| ttggttatac aatattgttt taattcccaa aattgtcctc tttcctcact atgaagaagg | 600 |
| acatattcca ggcatattaa taataatatt ctatggcatt ccatattct gtctggttgc | 660 |
| cttagtgagg gcctccataa ctgatccagg aagactccct gagaaccca agatcccaca | 720 |
| tggagaaagg gagttctggg aattatgtaa caagtgtaat ttgatgagac caaagcgttc | 780 |
| ccatcactgc agccgctgcg gccactgtgt gaggagaatg gatcatcact gtccatggat | 840 |
| taacaattgt gttggtgaag ataatcattg gctctttctg cagttgtgtt tctacactga | 900 |
| acttcttact tgctacgcac tgatgttttc tttctgccac tattactatt ttcttccact | 960 |
| aaaaaagcgt aatttggacc tctttgtttt tagacatgaa ttggccataa tgagactagc | 1020 |
| agcctttatg ggcattacta tgttagttgg aataactgga ctcttttaca ctcaactaat | 1080 |
| tggcatcatc acagatacaa catctattga aaagatgtca aactgttgtg aagatatatc | 1140 |
| gaggccccga aagccatggc agcagacctt ctcagaagtt tttggcactc gttggaagat | 1200 |
| cctgtggttc attcctttca ggcagaggca accactgcga gttccctacc actttgccaa | 1260 |
| tcatgtctaa acagatggat ggtgggcaca gatgggtcct ccatgctggc aatgcgttac | 1320 |

```
aggttttatg ataatagaac tatgacagtc ttcaagtcaa ttaaaatcca cccaccaatc    1380
ttaggcatca taatgtgccc caggctttat tttaatagtg atcttgatcc tgttgtggga    1440
ctaatacaag atctatattt aagttttaaa gcatgtttac tttcaaatta gctttccaca    1500
gggatttctt gaaatgcttt tgttattaaa ctcaaaaggc agtgattagg atgaaataat    1560
tgtacataat ttattttagt actgacagtg ttacagattc taatttatgg taaatttcag    1620
atgtttattt aaaattttca cttttaaaca gtaaccaaat ctaaatttaa ttattcaggt    1680
tttacaaaag ttgatacacc ttcttatagt ataggtaaat tttcttttc aaatccaatt    1740 taaaataacc tttccttta aatgtgctgc aacgttttta aaaatgcagc agcataggag    1800
tgaacaacag caacacaaaa cgggcattgg tttcttagga gtggcttgct tacgttttct    1860
tcttttttct tcaccaaaac caacatgaaa gtaccactga agtaaaacac caactaccta    1920
ccttactata aaggaaatgt taaaattttt ttcacaataa ttttttcaat tttcactatt    1980
actgttgtaa ttattgattg tgattaaaat atttgctccc aggagaactc ctgaccagtg    2040
ggcatgtatt cctattttat cctaagattt taatgagcaa aaggggaga gaatttgcaa    2100 taacttcaca attacctttt ctagtgcagt tatattagaa tgcatatgtt tttaaaatgc    2160
tagtataact agatagtata taatgtacag tataaagagg aatattgtgc ttttgaaaag    2220
agtatacttt ttacttttat ttatgtacta gtagatgtaa aatttcgcat tgaaggttta    2280
tatatattgg ccaactcata tagaaatttt atttatagga agctactact aaaaaaagtc    2340
actaactttg tgtacctata atccctaaat taaaattaaa ttttaattgg ctggctgtaa    2400
tttgcattga gagaccttt actagtagct agtgttagga agtgaaccta aaataagaaa    2460
atataatgat ctgtgtttat cattagcctt gtacaaatgt aaattactaa tagtgatgtt    2520
cttttgcaag gcatagaaca tttgtatgaa aagacattta gtatgctttg aaaaaaactc    2580 agctttagt ttttttccat tagaatactg caaaacccat atatcttttt aaaaaattta    2640
tgtactcaca gtctttccct tgaagagaag attgaaaaag tctactgttc ataaaccatg    2700
ctaacatttt cctttagct agttttgaaa gtaaggaaca atacctggga aataataaaa    2760
cagaaggtta ccattgtcag ccagttggct atactgtggt tagttctttc agaaattgta    2820
aatatcttgt agcatattct gaaataatag agtaagttct tctcagagat gttaatatca    2880
tgtttttcat gttctaatta gaatacttta ttacttacaa actcagaaat acgaacagaa    2940
atacagcaga cgaacatatt tattggtact gaaagagat gtagtaaatt aaatagaaga    3000
aatatattta taaagcttag tgaaacacaa aattagaatg ttcatgtcag gcacaagggt    3060
ttggattttg tgcaagctaa tttggccaca tttggcctgg tgacagaact gttcataagg    3120
aagtaatata tagataaggt aggtagatat cagttgaatg ccttatattg tatacattcc    3180
tttcaaataa agaccttgag aaaacaaaaa aaaaaaaaa aaaaaaaaa aaaaaaaaa    3240 aaaaaaaaaa acaaaaaaaa aaaaaaa                                       3267
```

<210> SEQ ID NO 48
<211> LENGTH: 160
<212> TYPE: PRT
<213> ORGANISM: Human

<400> SEQUENCE: 48

Met Leu Ala Leu Arg Leu Leu Asn Val Val Ala Pro Ala Tyr Phe Leu
1               5                   10                  15

Cys Ile Ser Leu Val Thr Phe Val Leu Gln Leu Phe Leu Phe Leu Pro
            20                  25                  30

```
Ser Met Arg Glu Asp Pro Ala Ala Ala Arg Leu Phe Ser Pro Ala Leu
     35                  40                  45
Leu His Gly Ala Leu Phe Leu Phe Leu Ser Ala Asn Ala Leu Gly Asn
 50                  55                  60
Tyr Val Leu Val Ile Gln Asn Ser Pro Asp Asp Leu Gly Ala Cys Gln
 65                  70                  75                  80
Gly Ala Ser Ala Arg Lys Thr Pro Cys Pro Ser Pro Ser Thr His Phe
                 85                  90                  95
Cys Arg Val Cys Ala Arg Val Thr Leu Arg His Asp His His Cys Phe
                100                 105                 110
Phe Thr Gly Asn Cys Ile Gly Ser Arg Asn Met Arg Asn Phe Val Leu
            115                 120                 125
Phe Cys Leu Tyr Thr Ser Leu Ala Gln Glu Leu Thr Arg Gly Leu Arg
        130                 135                 140
Lys Glu Val Ala Ala Gly Pro Ala Gly Pro His Val Gln Cys Arg Lys
145                 150                 155                 160

<210> SEQ ID NO 49
<211> LENGTH: 3097
<212> TYPE: DNA
<213> ORGANISM: Human

<400> SEQUENCE: 49
ccttactcgc tggcgcccaa gtgggaagcc agcagctgcc cgctccctcc tccccacatc         60
cccgctactt gcccagttcc cgaagcgaag cgcaggctgc gagccagccg ggccgagccc        120
acaactttgc agcctcgggc agggcgagag ccggcgtccg gggctcctct tgtcggcgac        180
cagagctcgg aatgtaatcg aggatgctgg ccctgcggct gctcaacgtg gtggcccccg        240
cctacttctt gtgcatctcc ctggtgacct tcgtgctgca gtcttcctc ttcctgccca         300 gcatgcgcga ggaccccgcg gccgcccggc tcttctcgcc cgccctgctc acggggcgc         360 tcttcctatt cctctcggcc aacgccctgg gcaattacgt ccttgtcatc cagaactccc        420
cagacgacct gggggcctgc caggggggcct cggccaggaa gactccatgc ccctcaccta       480
gcacccactt ctgccgagtg tgcgccagag tcaccctgag gcacgaccat cactgtttct        540
tcaccggcaa ctgcatcggg agcaggaaca tgcgcaactt cgtcctgttc tgcctctaca        600 cctcctggc gcaagaactt acaagaggtc ttcggaaaga ggtggctgct gggcctgctg         660
gtccccatgt tcaatgtcgg aagtgagagc tccaagcagc aggataagta gtagacactc        720
ccgtcattta tctctctgtc tctgtcttga ctcctcctga gcataaaacc atggcagcct        780
tgtctccacc catgactcac tacaaccttg tgctggtaag gtcctagcat cttcccctca        840
ccttccaccc atgagaacag cgtgagctgg tggatcatga caaggaggaa aaatgtcccc        900
ccaggcattt ctaggctcct cacgagccag ccaggtggct gctagctgtt aggctgcctc        960
tgctttcttt ccgtcccctt gggatccctg ctttcccct cttcctggct catccattct        1020
ccaccgtgtc tcattcatca ctgctgtctg ctagagccct tcctctcagc ccccatgttg       1080
ggagagggga gtggattctt gctgctggta tgagactccc tgggacctag aggctggcaa       1140
atgtttaaaa tcaccacgtg taagaggcag ccaagtcagc tctgccaact gctagggag        1200 ttgggaaaga gtgggtgtgt gtccgcatcc cctctgtagg aaaagaact tagtagcttg        1260 ctgctccctc accaccccc accaggttca agaccctttt tctgggagac agcaatcaat        1320
ggcctgcttt ccaaatgt tattcccgt ccgccctgcc ccatctggcc ggcccagccc          1380
agtccaggac ctggctggat gcttcctgtc cctggaactc ttccagcctt tctacttgat       1440
```

-continued

```
ctccagcccc caggtctttg ccagatgatg ggaaggcaag gaagaaggga cagggaaaga    1500
taattactga taaatgaagg ggatattcga ctgtataacc atatggaagt gtgtgtgtgt    1560
gtgtgtgtgt gtgtgtgtgt gtgtgtgtga gagagagaga gagagagaga gagagatggg    1620
tggtggtgag aagtgttgtt agaaacatat aggaataatg cctaggggaa agggagaagt    1680
gagagggaca attgggttca tttatgccct atacaaaggg cattccagca gctgaaactc    1740
ttcaatgttt gaatggctgc ctgtgaaggt agtgagtgcc ccatcactgg aggtattcca    1800
gcagagtcta ggcagtcgtc tgccaggcat gctgtggaag ggatttctgt acagggtcat    1860
tctaggtgag cttacacatt ccttccaacc ccaaggttct gatgtcctgg ttgtgattgc    1920
tggacccaga ggcaagatct gcagagatgc ctgtgagata tttgctttcc tagaggggag    1980
tgtgggcatg ggaggggtct gaaaatcagg acccaaccca gccactgaag agagagtctc    2040
tgcagagaca gggctacctg ggtggttgag gggactgaca tttgaggaca gggagatgga    2100
gcagtgtcat tgtcagtggc agggcatggg gggcagtggt gagctaaggc tgaggagtgg    2160
agatgaccag aatataaggg tgcaattccc agaccatccc tgcgcatctg actgactccg    2220
gtggaggcac tgctgtgtgt tttctgaaac ctagaggacc agacccctcc tgactgggtc    2280
ccaaagccaa tatgacatcc atgcaggcag cagtgctgaa tccatgccct gcaatgtcca    2340 accccccaact gcagtgaccc gctgatagct gcgcaacagc ctgggttctt gagcagagat    2400
tgggaggact ttactgtggt tctgccttca caccccctag agagctaatg tagtattggc    2460
tccacctgct cacatttctc cctcccatac tcattccttc actcatccat cctacgtata    2520
tttattgagt gccaactacg ttcccagcct cttccaggca ctggcaatgc agtgatgaac    2580
aggatgacaa gattcatgcc atcaggggca ccttgtcact gccgtctgtg cactgattca    2640
cactccctgc aaaatggtca ctctgccatc ttggtggttg gtggggcagg tcatttggaa    2700
ataaagaatg tgatagagat ggctgaagag gggaagccta ggctgcctca atggaggagt    2760 cgctggggc atttcaccc acaattctgg ccatacttaa gcaatgggag ggagagggag    2820
gaggggaaga tctgggcaat tttgccttg actctttcct ggctccagag ctcaagctta    2880
gaagccagcc ctgctatttc cagcctcctg aaggctcagc acggtgaggc ctgacatcct    2940
ggggaagggc aacagggaga cctacaggat gttggctgct cgcagactgg tcaatggggg    3000
atgacggtgg ggaggttgcc agatgtgaga cttgagtagc attttgtacac atggccctgt    3060 attgtccttg aagaacatca ataaaatata tggtttt                            3097
```

<210> SEQ ID NO 50
<211> LENGTH: 409
<212> TYPE: PRT
<213> ORGANISM: Human

<400> SEQUENCE: 50

```
Met Thr Gln Lys Gly Ser Met Lys Pro Val Lys Lys Lys Thr Glu
1               5                   10                  15

Glu Pro Glu Leu Glu Pro Leu Cys Cys Cys Glu Tyr Ile Asp Arg Asn
            20                  25                  30

Gly Glu Lys Asn His Val Ala Thr Cys Leu Cys Asp Cys Gln Asp Leu
        35                  40                  45

Asp Glu Gly Cys Asp Arg Trp Ile Thr Cys Lys Ser Leu Gln Pro Glu
    50                  55                  60

Thr Cys Glu Arg Ile Met Asp Thr Ile Ser Asp Arg Leu Arg Ile Pro
65                  70                  75                  80

Trp Leu Arg Gly Ala Lys Lys Val Asn Ile Ser Ile Ile Pro Pro Leu
```

```
                      85                  90                  95
Val Leu Leu Pro Val Phe Leu His Val Ala Ser Trp His Phe Leu Leu
                100                 105                 110

Gly Val Val Leu Thr Ser Leu Pro Val Leu Ala Leu Trp Tyr Tyr
            115                 120                 125

Tyr Leu Thr His Arg Arg Lys Glu Gln Thr Leu Phe Phe Leu Ser Leu
        130                 135                 140

Gly Leu Phe Ser Leu Gly Tyr Met Tyr Tyr Val Phe Leu Gln Glu Val
145                 150                 155                 160

Val Pro Lys Gly Arg Val Gly Pro Val Gln Leu Ala Val Leu Thr Cys
                165                 170                 175

Gly Leu Phe Leu Ile Leu Leu Ala Leu His Arg Ala Lys Lys Asn Pro
                180                 185                 190

Gly Tyr Leu Ser Asn Pro Ala Ser Gly Asp Arg Ser Leu Ser Ser Ser
            195                 200                 205

Gln Leu Glu Cys Leu Ser Arg Lys Gly Gln Lys Thr Lys Gly Phe
        210                 215                 220

Pro Gly Ala Asp Met Ser Gly Ser Leu Asn Asn Arg Thr Thr Lys Asp
225                 230                 235                 240

Asp Pro Lys Gly Ser Ser Lys Met Pro Ala Gly Ser Pro Thr Lys Ala
                245                 250                 255

Lys Glu Asp Trp Cys Ala Lys Cys Gln Leu Val Arg Pro Ala Arg Ala
                260                 265                 270

Trp His Cys Arg Ile Cys Gly Ile Cys Val Arg Arg Met Asp His His
            275                 280                 285

Cys Val Trp Ile Asn Ser Cys Val Gly Glu Ser Asn His Gln Ala Phe
        290                 295                 300

Ile Leu Ala Leu Leu Ile Phe Leu Leu Thr Ser Val Tyr Gly Ile Thr
305                 310                 315                 320

Leu Thr Leu Asp Thr Ile Cys Arg Asp Arg Ser Val Phe Thr Ala Leu
                325                 330                 335

Phe Tyr Cys Pro Gly Val Tyr Ala Asn Tyr Ser Ser Ala Leu Ser Phe
                340                 345                 350

Thr Cys Val Trp Tyr Ser Val Ile Ile Thr Ala Gly Met Ala Tyr Ile
            355                 360                 365

Phe Leu Ile Gln Leu Ile Asn Ile Ser Tyr Asn Val Thr Glu Arg Glu
        370                 375                 380

Val Gln Gln Ala Leu Arg Gln Lys Thr Gly Arg Arg Leu Leu Cys Gly
385                 390                 395                 400

Leu Ile Val Asp Thr Gly Leu Leu Gly
                405

<210> SEQ ID NO 51
<211> LENGTH: 3789
<212> TYPE: DNA
<213> ORGANISM: Human

<400> SEQUENCE: 51
ggggtacccg gaagcgcgcg tggacctggc gcaccgagcc gggcgggcgg aggggcggtt      60
gggacggcgc ggggaggcgg gcgcgccgcc cgggccgcgg cgggctgtgg tcacaggtgg     120
gcggctgcgg cgagggagcg gccgagcgga gcccgggtcc cggagactcc tgccgtcacg     180
cccggggctc cgcgtagcag agatcgggag acgcgtctgt gcctccgggg aagccgaccc     240
atctcccctc cgcctctttg gctgcagttg cacctccggc cagagggcag gtgcaaatca     300
```

```
tgacacagaa gggcagtatg aagcctgtga agaaaaagaa aaccgaagaa cctgaattgg    360
agccccgtgt ctgctgcgag tacatagatc ggaatgggga aaagaaccac gtggctactt    420
gtttgtgtga ttgtcaagat ctggatgaag ggtgtgatcg atggattaca tgtaaatctt    480
tacagccaga gacttgtgaa agaatcatgg atacaatttc tgatcgcctc cgaattcctt    540
ggcttagggg agccaaaaaa gtgaacatca gcatcatccc tccgcttgtc ctgctgcctg    600
tcttccttca tgtggcttcc tggcatttcc tcctgggggt ggtggttttg acctcccttc    660
ctgtgctggc actgtggtac tactacctca ctcacagaag gaaagaacag accctgtttt    720
tcctgagcct tggactgttc tctctgggct acatgtacta tgtgttcctg caggaagtgg    780
tccccaaagg gcgtgtgggt cccgttcagc tggcggttct acctgcgggg ttatttctga    840
tactcttagc cttgcacaga gccaagaaga atccaggcta cctcagcaat ccagcaagcg    900
gtgacagatc tctaagcagc agccagctgg agtgcctgag cagaaagggg caggagaaga    960
ccaaagggtt ccctggggca gacatgtcgg gcagtctcaa caatcgcaca acaaaggatg    1020
accccaaggg ctcttccaag atgccagctg gaagcccac caaagcgaag gaggactggt    1080
gtgccaagtg ccagctggtg cgaccagccc gggcatggca ctgccggata tgtggcatct    1140
gtgtgaggag aatggatcat cattgtgtct ggataaatag ctgcgttgga gaatcaaatc    1200
atcaagcatt tatacttgcc cttttgatct tcttgctcac ctcggtgtat gggatcacac    1260
tgaccttgga caccatttgt agagacagaa gtgtcttcac agctcttttc tattgtcctg    1320
gagtttatgc aaattacagc tcggctctgt ccttcacctg cgtgtggtac tctgtgatca    1380
tcacagcagg catggcctac atcttcctga tccagctgat caacatcagc tacaatgtga    1440
ctgagcggga agtccagcag gccctccgac agaagactgg gcgccggctc ctctgcgggc    1500
tcatcgtgga cacagggtta cttggatgag ccaactccgc ttccttccca tggataggaa    1560
gggactctgt gtattattca ggtttattgg cacgaagata cttgttttaa gttccttgag    1620
aacccatgat ggacagttga cagaatgctt aaacctgtca aaagatgagt gatcttgtgt    1680
gggaaaagcc ttcccaggcg tctgtaccga aaggagcagc aaacaagggg ctaatccatg    1740
agcagtgttc tgtaggctct gtgacatctt tggtttatag gattttggag ccttttatga    1800
tctggaacta tttgagggt ttcattatag gccttggttc tctccagggg ccagatgagt    1860
ttattgtgga atctttgaaa ggacaaggcc tctgtgaatg aatcagtccc agggaagcat    1920
ttggtggtgg cggcagtgga ggattgcccg gtgaacctat aaatcagcag tctcttgggc    1980
agaggagcaa gccccctcgaa catgatttca aacaagcagg tcctcttctc tcatctcacg    2040
tccttagtct ctgttaatga acatactgga tgtggagttt aataaattac ctactatcat    2100
ctggccactt agattattat cacaccactg tggactgttc ctgggggggag aagaacagac    2160 cgatttgaaa gattcaaggg agaaagatta aggatcagga ttgcatgaaa gaagaaaatc    2220
cttcaatatt taaaatgttt cttacaatac ccacggagca ctttatggt tccagccgag    2280 cgttcctgaa atgaactgac cattaacagc gcctctttga taggttaccc tgatgctgct    2340
aaagtaaagc cttaagtgtg ttttggac aacgtgctgc ttattccacc tcagccacat    2400
atgtgtttgt gtttaggata ttgtaaatct ttgctaagta gtgttttcct tggtgaatga    2460
agtcattgtt gtcttcaagt gtaccatctg cctagcaaaa aattgctaca aactttctct    2520
tatgcaatag tccttggtac ttctaatatt tttagcaaga gacaattttc tgtactagaa    2580
tcttccactg ccagaaaaca cagtgccagt aaggttctac ataccactga ccatctgctt    2640
aatagacatg tatttccttt gagtaggaca ttagcttttg attataaagc tcaactagta    2700
```

-continued

```
taagcaaaaa tataacatct agaagcacag ttttagccag gatgtttaaa aattacagtt    2760
ttgtgagact taagggtctt tttaacctag gtaagtttat atgacctaac ttaattgtag    2820
ccatattctg gtaccttcca ttttgaaaag tagaggttgc ttaagcaagc aatggataat    2880
aagagacttt tcctgaggca cctgtttgga atctggtttt ctcagcggca gcttgacatg    2940
tgcacccttt tgtattaaac actgcaaggg tgatgcaggg gagcaggaaa gccatcctaa    3000
actcactact gagtacgatt cagtatgttc ctgtggatgt ctgctgtgac taatataaat    3060
ttcttgcaga atcagctaca cttaattatg ttgctgatag acaagcatcc acgcttcagc    3120
tggcactaag tgttttcatt gtaggatcag cagcaggtta aagactgaac ggttagtgaa    3180
gacaaatgtc ttaagaggct gcgatgtcta ggttgggctt gtgacttctt agtggcctag    3240
ccttcttgat ggcaccttga aagtgaactt ctagaaatct acatttaaaa ggcaaagctt    3300
taaaagcaga gctagtctat tctagttact gatgcaacta aaattctgta tttcttaaga    3360
tggagccact gacgagatgt cacagtatag agcctgcagt ctcaactcat tgtgatccta    3420
atggtctggg tgattggatg gtttgagttg ttagggattt tgagtttttc attttattgc    3480
atatctgggt tggatgttag actaaaggaa acccaggaat atttacctgg tgttacattt    3540
aatatttaat gtaactggtc tagcaacatt aagggggatt tctgaagcca actccggagg    3600
ctgtgggctg cacattttgc actgttttta tatacttgta ttcatatcct cttatcacct    3660
cagactcaga cacaaggcct tttacatgga aattttacaa attacttcca tttatgtaaa    3720
ataacgtcct gtgaccaagt tgtttaaatg gaaaataaag tgctttcttt aaggaaaaaa    3780
aaaaaaaaa                                                           3789
```

<210> SEQ ID NO 52
<211> LENGTH: 284
<212> TYPE: PRT
<213> ORGANISM: Human

<400> SEQUENCE: 52

```
Met Gly Gln Pro Trp Ala Ala Gly Ser Thr Asp Gly Ala Pro Ala Gln
1               5                   10                  15

Leu Pro Leu Val Leu Thr Ala Leu Trp Ala Ala Ala Val Gly Leu Glu
                20                  25                  30

Leu Ala Tyr Val Leu Val Leu Gly Pro Gly Pro Pro Leu Gly Pro
            35                  40                  45

Leu Ala Arg Ala Leu Gln Leu Ala Leu Ala Ala Phe Gln Leu Leu Asn
    50                  55                  60

Leu Leu Gly Asn Val Gly Leu Phe Leu Arg Ser Asp Pro Ser Ile Arg
65                  70                  75                  80

Gly Val Met Leu Ala Gly Arg Gly Leu Gly Gln Gly Trp Ala Tyr Cys
                85                  90                  95

Tyr Gln Cys Gln Ser Gln Val Pro Pro Arg Ser Gly His Cys Ser Ala
            100                 105                 110

Cys Arg Val Cys Ile Leu Arg Arg Asp His His Cys Arg Leu Leu Gly
        115                 120                 125

Arg Cys Val Gly Phe Gly Asn Tyr Arg Pro Phe Leu Cys Leu Leu Leu
    130                 135                 140

His Ala Ala Gly Val Leu Leu His Val Ser Val Leu Leu Gly Pro Ala
145                 150                 155                 160

Leu Ser Ala Leu Leu Arg Ala His Thr Pro Leu His Met Ala Ala Leu
                165                 170                 175

Leu Leu Leu Pro Trp Leu Met Leu Leu Thr Gly Arg Val Ser Leu Ala
```

```
                    180              185              190
Gln Phe Ala Leu Ala Phe Val Thr Asp Thr Cys Val Ala Gly Ala Leu
            195                  200                  205

Leu Cys Gly Ala Gly Leu Leu Phe His Gly Met Leu Leu Leu Arg Gly
        210                  215                  220

Gln Thr Thr Trp Glu Trp Ala Arg Gly Gln His Ser Tyr Asp Leu Gly
225                  230                  235                  240

Pro Cys His Asn Leu Gln Ala Ala Leu Gly Pro Arg Trp Ala Leu Val
                245                  250                  255

Trp Leu Trp Pro Phe Leu Ala Ser Pro Leu Pro Gly Asp Gly Ile Thr
            260                  265                  270

Phe Gln Thr Thr Ala Asp Val Gly His Thr Ala Ser
        275                  280

<210> SEQ ID NO 53
<211> LENGTH: 1319
<212> TYPE: DNA
<213> ORGANISM: Human

<400> SEQUENCE: 53
gattccgagc gcctccactg ctggtccgtt ggccagatca actcgccgcg tgggccggcc      60
gttccctgag agtctgagcg ctcgccgcac ccccttccga gcttctattg ccgtagcag     120 acgtccgtct gccgctatct ccgccccaat acggaagcgg cctagtcctc cggctccgac    180
agctgggtgt ccaggccatg gggcagccct ggcggctgg gagcacggac ggggcgcccg     240
cgcagctgcc tctcgtgctc accgcgctgt gggccgcggc cgtgggcctg agctggcctt    300
acgtgctggt gctcggtccc gggccgccgc cgctgggacc cctggcccgg ccttgcagc     360 tggcgctggc cgccttccag ctgctcaacc tgctgggcaa cgtggggctc ttcctgcgct    420
cggatcccag catccgtggc gtgatgctgg ccggccgcgg tctgggccag gctgggctt     480 actgctacca atgccaaagc caggtgccgc cacgcagcgg acactgctct gcctgccgcg    540
tctgcatcct gcgtcgggac caccactgcc gcctgctggg ccgctgcgtg gcttcggca    600 actaccggcc cttcctgtgc ctgctgcttc atgccgccgg cgtcctgctc acgtctctg     660 tgctgctggg ccctgcactg tcggccctgc tgcgagccca cacgcccctc cacatggctg    720
ccctcctcct gcttccctgg ctcatgttgc tcacaggcag agtgtctctg cacagtttg    780 ccttggcctt cgtgacggac acgtgcgtgg cgggtgcgct gctgtgcggg gctgggctgc    840
tcttccatgg gatgctgctg ctgcggggcc agaccacatg ggagtgggct cggggccagc    900
actcctatga cctgggtccc tgccacaacc tgcaggcagc cctggggccc cgctgggccc    960
tcgtctggct ctggcccttc ctggcctccc cattgcctgg ggatgggatc accttccaga   1020
ccacagcaga tgtgggacac acagcctcct gactccagga agagccagag ctgtgcaggg   1080 aggaagggt gagaggggg cccccacacc tagactcagt aaggaagtcg ggttggacct     1140
taacatctgc attggacaac tccacccctt ccttggcctt gccctgccc gcctacactc   1200 ctacgtgtcc agggcttggg ccgtgactta ggcagaggag tgcagaggag ggtctggcag   1260
gggctgctca ggccgcctag ctgccccttt gccaggttaa taaagcactg acttgttaa    1319

<210> SEQ ID NO 54
<211> LENGTH: 19
<212> TYPE: RNA
<213> ORGANISM: Artificial Sequence
<220> FEATURE:
<223> OTHER INFORMATION: synthetic
```

-continued

```
<400> SEQUENCE: 54
gacagaugcc aacuuauaa                                               19

<210> SEQ ID NO 55
<211> LENGTH: 19
<212> TYPE: RNA
<213> ORGANISM: Artificial Sequence
<220> FEATURE:
<223> OTHER INFORMATION: synthetic

<400> SEQUENCE: 55
ccaaggaucu ucccaucua                                               19

<210> SEQ ID NO 56
<211> LENGTH: 19
<212> TYPE: RNA
<213> ORGANISM: Artificial Sequence
<220> FEATURE:
<223> OTHER INFORMATION: synthetic

<400> SEQUENCE: 56
acaaauggcc uaccugaua                                               19

<210> SEQ ID NO 57
<211> LENGTH: 19
<212> TYPE: RNA
<213> ORGANISM: Artificial Sequence
<220> FEATURE:
<223> OTHER INFORMATION: synthetic

<400> SEQUENCE: 57
ggcaacagau uuacaguau                                               19

<210> SEQ ID NO 58
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 58

Asp His His Cys
1
```